US012618101B2

(12) United States Patent
Sabeti et al.

(10) Patent No.: US 12,618,101 B2
(45) Date of Patent: May 5, 2026

(54) SHERLOCK ASSAYS FOR TICK-BORNE DISEASES

(71) Applicants: THE BROAD INSTITUTE, INC., Cambridge, MA (US); PRESIDENT AND FELLOWS OF HARVARD COLLEGE, Cambridge, MA (US); THE GENERAL HOSPITAL CORPORATION, Boston, MA (US)

(72) Inventors: Pardis Sabeti, Cambridge, MA (US); Jacob Lemieux, Boston, MA (US); Anne Piantadosi, Boston, MA (US); Erica Normandin, Cambridge, MA (US); Gordon Adams, Cambridge, MA (US); Eric Rosenberg, Boston, MA (US)

(73) Assignees: The Broad Institute, Inc., Cambridge, MA (US); President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 967 days.

(21) Appl. No.: 17/439,357

(22) PCT Filed: Mar. 13, 2020

(86) PCT No.: PCT/US2020/022776
§ 371 (c)(1),
(2) Date: Sep. 14, 2021

(87) PCT Pub. No.: WO2020/186223
PCT Pub. Date: Sep. 17, 2020

(65) Prior Publication Data
US 2022/0220546 A1 Jul. 14, 2022

Related U.S. Application Data

(60) Provisional application No. 62/860,225, filed on Jun. 11, 2019, provisional application No. 62/818,739, filed on Mar. 14, 2019.

(51) Int. Cl.
*C12Q 1/6844* (2018.01)
*B01L 3/00* (2006.01)
*C12Q 1/689* (2018.01)

(52) U.S. Cl.
CPC .......... *C12Q 1/6844* (2013.01); *B01L 3/5023* (2013.01); *C12Q 1/689* (2013.01); *B01L 2300/069* (2013.01); *B01L 2300/0825* (2013.01)

(58) Field of Classification Search
None
See application file for complete search history.

(56) References Cited

U.S. PATENT DOCUMENTS

| | | | |
|---|---|---|---|
| 2005/0069931 A1 | 3/2005 | Allis et al. | |
| 2013/0190196 A1 | 7/2013 | Onderdonk et al. | |
| 2015/0232881 A1* | 8/2015 | Glucksmann .......... | C12N 15/63 |
| | | | 435/468 |
| 2017/0211142 A1 | 7/2017 | Smargon et al. | |
| 2018/0298445 A1 | 10/2018 | Abudayyeh et al. | |
| 2018/0305773 A1 | 10/2018 | Abudayyeh et al. | |
| 2018/0340219 A1 | 11/2018 | Abudayyeh et al. | |

FOREIGN PATENT DOCUMENTS

| | | |
|---|---|---|
| WO | 2011/109762 A1 | 9/2011 |
| WO | 2014/093622 A8 | 12/2014 |
| WO | 2016/035044 A1 | 3/2016 |
| WO | 2016/172598 A1 | 10/2016 |
| WO | 2017/040316 A1 | 3/2017 |
| WO | 2017/070605 A1 | 4/2017 |
| WO | 2017/219027 A1 | 12/2017 |
| WO | 2018/035250 A1 | 2/2018 |
| WO | 2018/170333 A1 | 9/2018 |
| WO | 2018170340 A1 | 9/2018 |
| WO | 2019/005866 A1 | 1/2019 |
| WO | 2019/071051 A1 | 4/2019 |
| WO | 2019/126577 A2 | 6/2019 |
| WO | 2020/186101 A1 | 9/2020 |

OTHER PUBLICATIONS

Gootenberg et al. Multiplexed and portable nucleic acid detection platform with Cas13, Cas12a, and Csm6. Science. Apr. 27, 2018; 360(6387):439-444. doi: 10.1126/science.aaq0179. Epub Feb. 15, 2018. PMID: 29449508; PMCID: PMC5961727; supplementary material included (Year: 2018).*
Lemieux et al. A global map of genetic diversity in Babesia microti reveals strong population structure and identifies variants associated with clinical relapse. Nat Microbiol. Jun. 13, 2016;1(7):16079. PMID: 27572973; PMCID: PMC556307; cited as NPL # 6 in IDS filed Sep. 2014 (Year: 2016).*

(Continued)

*Primary Examiner* — Aaron A Priest
*Assistant Examiner* — Tian Yu
(74) *Attorney, Agent, or Firm* — F. Brent Nix, Esq.; Johnson, Marcou, Isaacs & Nix, LLC; Ming Zhang

(57) ABSTRACT

Provided herein is a nucleic acid detection system comprising a detection CRISPR system having an effector protein and one or more guide RNAs each designed to bind to corresponding target molecules that are diagnostic for a tick-borne disease state; and an RNA-based masking construct. In some embodiments, the detection system of may comprise i) two or more CRISPR systems, each CRISPR system comprising an effector protein and a guide RNA designed to bind to a corresponding target molecule that is diagnostic for a tick-borne disease state; and ii) a set of detection constructs, each detection construct comprising a cutting motif sequence that is preferentially cut by one of the activated CRISPR effector proteins. Exemplary tick-borne detectable microbes include *Babesia microti, Anaplasma phagocytophilum,* and *Borrelia miyamotoi.*

24 Claims, 14 Drawing Sheets

Specification includes a Sequence Listing.

(56)         References Cited

OTHER PUBLICATIONS

Liu et al. The Molecular Architecture for RNA-Guided RNA Cleavage by Cas13a. Cell. Aug. 10, 2017;170(4):714-726.e10. doi: 10.1016/j.cell.2017.06.050. Epub Jul. 27, 2017. PMID: 28757251. (Year: 2017).*

Couturie et al. Leptotrichia bacteremia in patients receiving high-dose chemotherapy. J Clin Microbiol. Apr. 2012;50(4):1228-32. doi: 10.1128/JCM.05926-11. Epub Jan. 11, 2012. PMID: 22205794; PMCID: PMC3318514. (Year: 2012).*

Gootenberg et al. Multiplexed and portable nucleic acid detection platform with Cas13, Cas12a, and Csm6. Science. Apr. 27, 2018; 360(6387):439-444. doi: 10.1126/science.aaq0179. Epub Feb. 15, 2018. PMID: 29449508; PMCID: PMC5961727; cited as NPL # 4 in IDS filed Sep. 14, 2021 (Year: 2018).*

Zusi, K. (Feb. 15, 2018). Sherlock team advances its CRISPR-based diagnostic tool. @broadinstitute. https://www.broadinstitute.org/news/sherlock-team-advances-its-crispr-based-diagnostic-tool (Year: 2018).*

Walper et al. Detecting Biothreat Agents: From Current Diagnostics to Developing Sensor Technologies. ACS Sens. Oct. 26, 2018;3(10):1894-2024. doi: 10.1021/acssensors.8b00420. Epub Sep. 11, 2018. PMID: 30080029 (Year: 2018).*

Lemieux et al. A global map of genetic diversity in Babesia microti reveals strong population structure and identifies variants associated with clinical relapse. Nat Microbiol. Jun. 13, 2016;1(7):16079; cited as NPL # 6 in IDS filed Sep. 14, 2021 (Year: 2016).*

International Search Report and Written Opinion issued by the European Patent Office, as International Searching Authority for PCT/US2020/022776 on Jun. 15, 2020.

Akter, et al., "Potential of Cell-free DNA as a Screening Marker for Parasite Infections in Dog", Genomics, vol. 111, No. 4, pp. 906-912, Accepted Online: May 31, 2018.

Aman, et al., "Nucleic Acid Detection Using CRISPR/Cas Biosensing Technologies", https://dx.doi.org/10.1021/acssynbio.9b00507, pp. 1-8, Published Mar. 11, 2020.

Gootenberg, et al., "Multiplexed and Portable Nucleic Acid Detection Platform with Cas13, Cas12A, and Csm6", Science, vol. 360, No. 6387, pp. 1-14, Published: Apr. 27, 2018.

Gootenberg, et al., "Nucleic Acid Detection With CRISPR-Cas13a/C2c2", Science, vol. 356, No. 6336, pp. 1-12, Published: Apr. 28, 2017.

Lemieux, et al., "A Global Map of Genetic Diversity in Babesia Microti Reveals Strong Population Structure and Identifies Variants associated with Clinical Relapse", Nature Microbiology, vol. 1, No. 7, pp. 1-18, Published: Jun. 13, 2016.

Li, et al., "CRISPR-Cas12a-assisted Nucleic Acid Detection", Cell Discovery, vol. 4, No. 1, pp. 1-4, Published: Apr. 24, 2018.

Metsky, et al., "Capturing Sequence Diversity in Metagenomes with Comprehensive and Scalable Probe Design", Nature Biotechnology, vol. 37, No. 2, pp. 1-16, Published: Feb. 2019.

Pyzocha, et al., "Diverse Class 2 CRISPR-Cas Effector Proteins for Genome Engineering Applications", ACS Chemical Biology, vol. 13, No. 2, pp. 1-21, Published Feb. 16, 2018.

Sajid, et al., "Designs, Formats and Applications of Lateral Flow Assay: A literature Review", Journal of Saudi Chemical Society, vol. 19, Issue 6, pp. 689-705, Available Online: Sep. 16, 2014.

Zhao, et al., "Signal amplification of glucosamine-6-phosphate based on ribozyme glmS", Biosens Bioelectron, vol. 16, pp. 337-342, 2014.

Dirks et al., "Triggered amplification by hybridization chain reaction", PNAS, vol. 101, pp. 15275-15728, 2004.

Lu, et al., "Ultra-sensitive colorimetric assay system based on the hybridization chain reaction-triggered enzyme cascade amplification", ACS Appl Mater Interfaces, vol. 9, No. 1, pp. 167-175, 2017.

Wang, et al., "An enzyme-free colorimetric assay using hybridization chain reaction amplification and split aptamers", Analyst, The Royal Society of Chemistry, 20 pages, 2013.

Song, et al., "Non-covalent fluorescent labeling of hairpin DNA probe coupled with hybridization chain reaction for sensitive DNA detection", Applied Spectroscopy, vol. 70, No. 4, pp. 686-694, 2016.

Sajid et al., "Designs, formats and applications of lateral flow assay: A literature review", J Saudi Chem Soc, vol. 19, No. 6, pp. 689-705, 2015.

Jia, et al., "CARD 2017: expansion and model-centric curation of the Comprehensive Antibiotic Resistance Database", Nucleic Acids Research, vol. 45, pp. D566-573, 2017.

Pfeifer et al., "A single mutation in poliovirus RNA-dependent RNA polymerase confers resistance to mutagenic nucleotide analogs via increased fidelity", PNAS, vol. 100, No. 12, pp. 7289-7294, 2003.

Pfeiffer et al., "Ribavirin Resistance in Hepatitis C Virus Replicon-Containing Cell Lines Conferred by Changes in the Cell Line or Mutations in the Replicon RNA", Virol., vol. 79, No. 4, pp. 2346-2355, 2005.

Diehl, et al., "Ebola Virus Glycoprotein with Increased Infectivity Dominated the 2013-2016 Epidemic", Cell, vol. 167, No. 4, pp. 1088-1098, 2016.

Andersen, et al., "Clinical Sequencing Uncovers Origins and Evolution of Lassa Virus", Cell, vol. 162, No. 4, pp. 738-750, Aug. 13, 2015.

Holdenrieder, et al., "Nucleosomes in Serum of Patients With Benign and Malignant Diseases", Int J Cancer, vol. 95, pp. 114-120, 2001.

Williams, et al., "Detection of Nucleosome Particles in Serum and Plasma from Patients with Systemic Lupus Erythematosus Using Monoclonal Antibody 4H7", J Rheumatol, vol. 28, pp. 81-94, 2001.

Holford, NH, "Clinical Pharmacokinetics and Pharmacodynamics of Warfarin Understanding the Dose-Effect Relationship", Clinical Pharmacokinetics, Springer International Publishing, vol. 11, No. 6, pp. 483-504, Dec. 1986.

Litin et al., "Current concepts in anticoagulant therapy", Mayo Clin. Proc., vol. 70, No. 3, pp. 266-272, 1995.

Rusdiana, et al., "Responsiveness to low-dose warfarin associated with genetic variants of VKORC1, CYP2C9, CYP2C19, and CYP4F2 in an Indonesian population", Eur J Clin Pharmacol, vol. 69, No. 3, pp. 395-405, Mar. 2013.

Zusi, K., "Sherlock team advances its CRISPR-based diagnostic tool", retrieved from https://www.broadinstitute.org/news/sherlock-team-advances-its-crispr-based-diagnostic-tool, Published: Feb. 15, 2018, 4 pages.

Walper, et al., "Detecting Biothreat Agents: From Current Diagnostics to Developing Sensor Technologies", ACS Sensors, vol. 3, No. 10, pp. 1894-2024, Oct. 26, 2018.

Smargon, et al., "Cas13b is a Type VI-B CRISPR-associated RNA-Guided RNase differentially regulated by accessory proteins Csx27 and Csx28", Molecular Cell, vol. 65, pp. 618-630, 2017.

Schluger, et al., "Application of DNA Amplification to Pneumocystosis: Presence of Serum Pneumocystis carinii DNA During Human and Experimentally Induced Pneumocystis carinii Pneumonia", J. Exp. Med., vol. 176, pp. 1327-1333, 1992.

Bigby, et al., "The Usefulness of Induced Sputum in the Diagnosis of Pneumocystis carinii Pneumonia in Patients with the Acquired Immunodeficiency Syndrome", Am. Rev. Respir. Dis., vol. 133, pp. 515-518, 1986.

Gire, et al., "Genomic surveillance elucidates Ebola virus origin and transmission during the 2014 outbreak", Science, vol. 345, pp. 1369-1372, 2014.

Phillippy, et al., "Efficient oligonucleotide probe selection for pan-genomic tiling arrays", BMC Bioinformatics, vol. 10, 11 pages, 2009.

Hou, et al., "Microfluidic Devices for Blood Fractionation", Micromachines, vol. 2, pp. 319-343, 2011.

Bhagat, et al., "Dean Flow Fractionation (DFF) Isolation of Circulating Tumor Cells (CTCs) from Blood", 15th International Conference on Miniaturized Systems for Chemistry and Life Sciences, Seattle, WA, Oct. 2-6, 2011, 3 pages.

Nakamura, et al., "Codon usage tabulated from the international DNA sequence databases: status for the year 2000", Nucl. Acids Res., vol. 28, pp. 292, 2000.

(56) References Cited

OTHER PUBLICATIONS

Broad Institute, "Questions and answers about CRISPR", @broadinstitute, Dec. 17, 2014, retrieved from www.broadinstitute. org/what-broad/areas-focus/project-spotlight/questions-and-answers-about-crispr, 3 pages.

Branda, et al., "Performance of United States Serologic Assays in the Diagnosis of Lyme Borreliosis Acquired in Europe", Clin Infect Dis, vol. 57, No. 3, pp. 333-340, 2013.

Makhani, et al., "A Twist on Lyme: the Challenge of Diagnosing European Lyme Neuroborreliosis", J Clin Microbiol, vol. 49, No. 1, pp. 455-457, 2011.

Vannier, et al., "Human Babesiosis", NEJM, vol. 366, No. 25, pp. 2397-2407, 2012.

Ebel, "Update on Powassan Virus: Emergence of a North American Tick-Borne Flavivirus", Annu Rev Entomol, vol. 55, pp. 95-110, 2010.

Kosoy, et al., "Novel Thogotovirus Associated with Febrile Illness and Death, United States, 2014", Emerg Infect Dis, vol. 21, No. 5, pp. 760-764, 2015.

Mcmullan, et al., "A New Phlebovirus Associated with Severe Febrile Illness in Missouri", NEJM, vol. 367, No. 9, pp. 834-841, 2012.

Krause, et al., "Human Borrelia miyamotoi Infection in the United States", NEJM, 368(3), pp. 291-293, 2013.

Gugliotta, et al., "Meningoencephalitis from Borrelia miyamotoi in an Immunocompromised Patient", NEJM, vol. 368, No. 3, pp. 240-245, 2013.

Pritt, et al., "Identification of a novel pathogenic *Borrelia* species causing Lyme borreliosis with unusually high spirochaetaemia: a descriptive study", Lancet Infect Dis, 16(5), pp. 556-564, 2016.

Pritt, et al., "Emergence of a New Pathogenic *Ehrlichia* Species, Wisconsin and Minnesota, 2009", NEJM, vol. 365, No. 5, pp. 422-429, 2011.

Abudayyeh, et al., "C2c2 is a single-component programmable RNA-guided RNA-targeting CRISPR effector", Science, 353(6299), 23 pages, 2016.

Shmakov, et al., "Discovery and Functional Characterization of Diverse Class 2 CRISPR-Cas Systems", Molecular Cell, 60, pp. 385-397, 2015.

East-Seletsky, et al., "Two distinct RNase activities of CRISPR-C2c2 enable guide-RNA processing and RNA detection", Nature, 538(7624) pp. 270-273, 2016.

Hale, et al., "Target RNA capture and cleavage by the Cmr type III-B CRISPR-Cas effector complex", Genes Dev, vol. 28, pp. 2432-2443, 2014.

Hale, et al., "RNA-Guided RNA Cleavage by a CRISPR RNA-Cas Protein Complex", Cell, vol. 139, pp. 945-956, 2009.

Peng, et al., "An archaeal CRISPR type III-B system exhibiting distinctive RNA targeting features and mediating dual RNA and DNA interference", Nucleic acids research, vol. 43, pp. 406-417, 2015.

Samai, et al., "Co-transcriptional DNA and RNA Cleavage during Type III CRISPR-Cas Immunity", Cell, vol. 151, pp. 1164-1174, 2015.

Greer, "Model Structure for the Inflammatory Protein C5a", Science, vol. 228, pp. 1055-1060, 1985.

Blundell, et al., "Knowledge-based protein modelling and design", Eur J Biochem, vol. 172, pp. 513-520, 1988.

Dey et al., "Toward a 'structural BLAST': using structural relationships to infer function", Protein Sci, vol. 22, No. 4, pp. 359-366, Apr. 2013.

Makarova et al., "Annotation and Classification of CRISPR-Cas Systems", Methods Mol Biol, vol. 1311, pp. 47-75, 2015.

Lewis et al., "Building the Class 2 CRISPR-Cas Arsenal", Mol Cell, vol. 65, No. 3, pp. 377-379, Feb. 2, 2017.

Kazlauskiene, et al., "A cyclic oligonucleotide signaling pathway in type III CRISPR-Cas systems", Science, 357, pp. 605-609, 2017.

Niewoehner, et al., "Type III CRISPR-Cas systems generate cyclic oligoadenylate second messengers to activate Csm6 RNases ", bioRxiv, 36 pages, 2017.

Niewoehner et al., "Structural basis for the endoribonuclease activity of the type III-A CRISPR-associated protein Csm6", RNA, vol. 22, pp. 318-329, 2016.

Carr et al., "Genome engineering", Nature Biotechnology, vol. 27, No. 12, pp. 1151-1162, 2009.

Hendel et al., "Chemically modified guide RNAs enhance CRISPR-Cas genome editing in human primary cells", Nat Biotechnol, vol. 33, No. 9, pp. 985-989, 2015.

Allerson, et al., "Fully 2'-Modified Oligonucleotide Duplexes with Improved in Vitro Potency and Stability Compared to Unmodified Small Interfering RNA", J. Med. Chem., vol. 48, pp. 901-904, 2005.

Bramsen, et al., "Development of therapeutic-grade small interfering RNAs by chemical engineering", Front. Genet., vol. 3, 22 pages, 2012.

Deng, et al., "CASFISH: CRISPR/Cas9-mediated in situ labeling of genomic loci in fixed cells", PNAS, vol. 112, pp. 11870-11875, 2015.

Sharma, et al., "Antisense oligonucleotides: modifications and clinical trials", MedChemComm, vol. 5, pp. 1454-1471, 2014.

Li, et al., "Engineering CRISPR-Cpf1 crRNAs and mRNAs to maximize genome editing efficiency", Nature Biomedical Engineering, vol. 1, 21 pages, 2017.

Lee, et al., "Synthetically modified guide RNA and donor DNA are a versatile platform for CRISPR-Cas9 engineering", eLife, vol. 6, pp. e25312, 17 pages, 2017.

Pearson, et al., "On the primer selection problem in polymerase chain reaction experiments", Discrete Applied Mathematics, 71, pp. 231-246, 1996.

Jabado, et al., "Greene SCPrimer: a rapid comprehensive tool for designing degenerate primers from multiple sequence alignments", Nucleic Acids Res, vol. 34, No. 22, pp. 6605-6611, 2006.

Jabado, et al., "Comprehensive viral oligonucleotide probe design using conserved protein regions", Nucleic Acids Res, vol. 36, No. 1, 10 pages, 2008.

Duitama, et al., "PrimerHunter: a primer design tool for PCR-based virus subtype identification", Nucleic Acids Res, vol. 37, No. 8, pp. 2483-2492, 2009.

\* cited by examiner

Wild Type (278L)        Relapse (278P)

Cytochrome B with
atovaquone

50S Ribosome with        Relapse Associated
azithromycin        Variant Sites

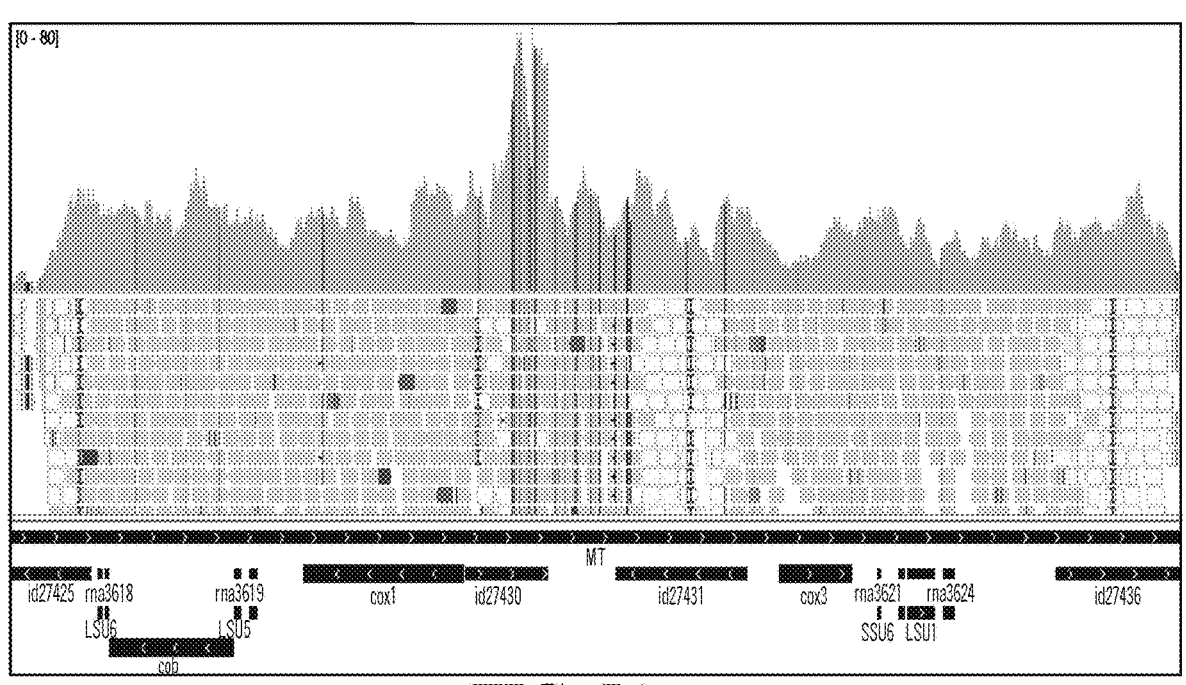
FIG. 5A
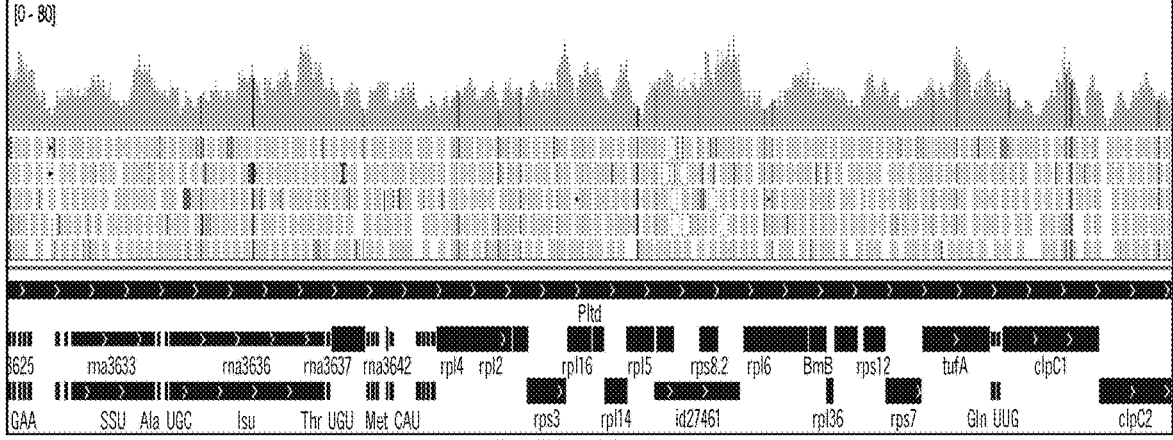
FIG. 5B
FIG. 5C

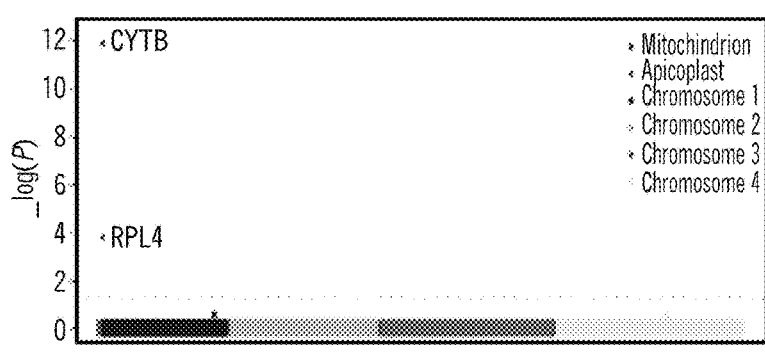
FIG. 7A
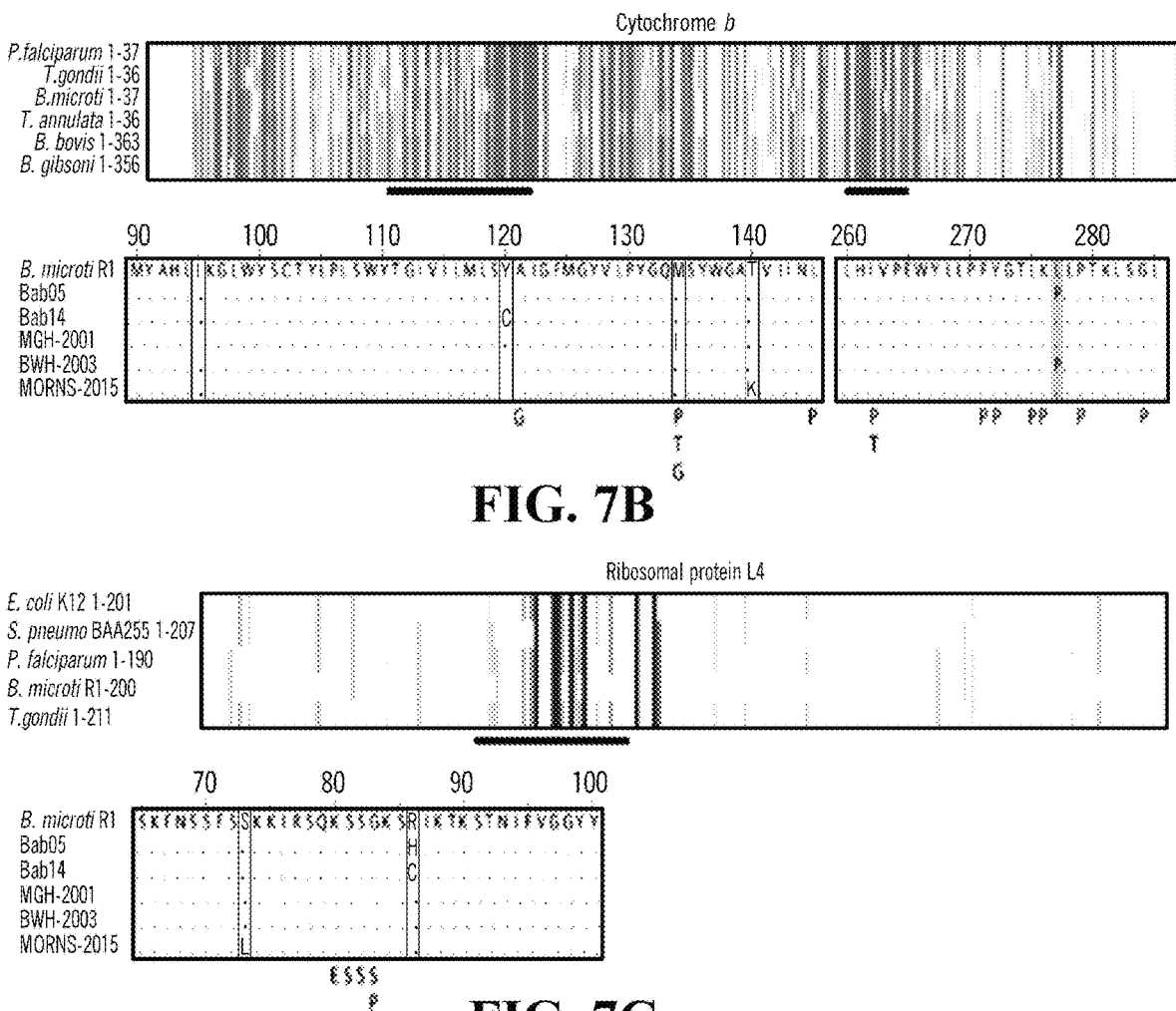
FIG. 7B
FIG. 7C

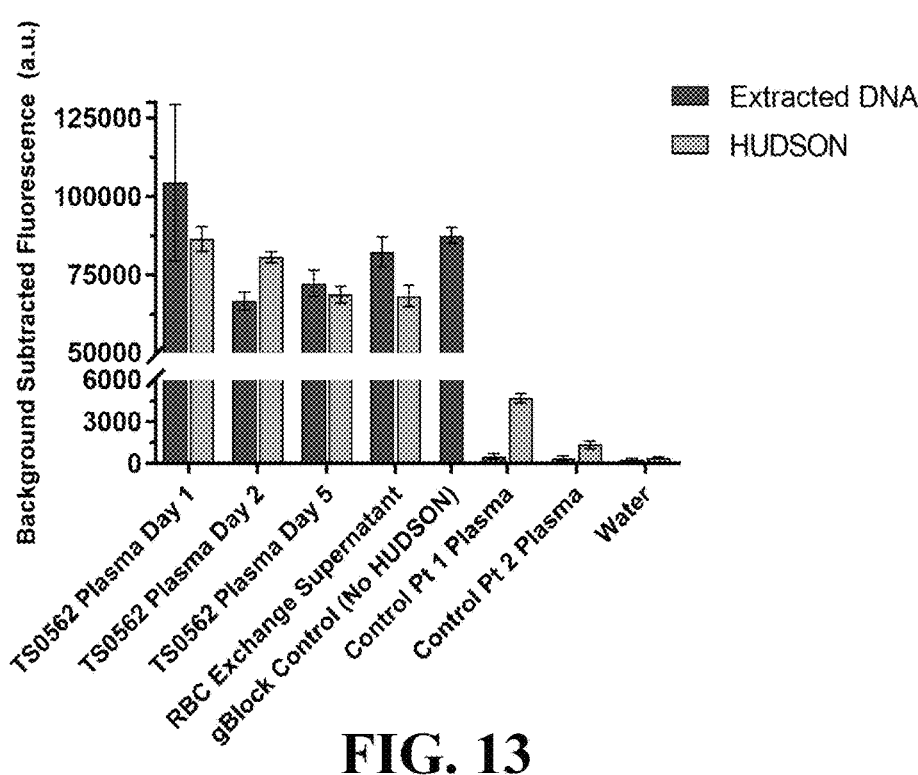
FIG. 13
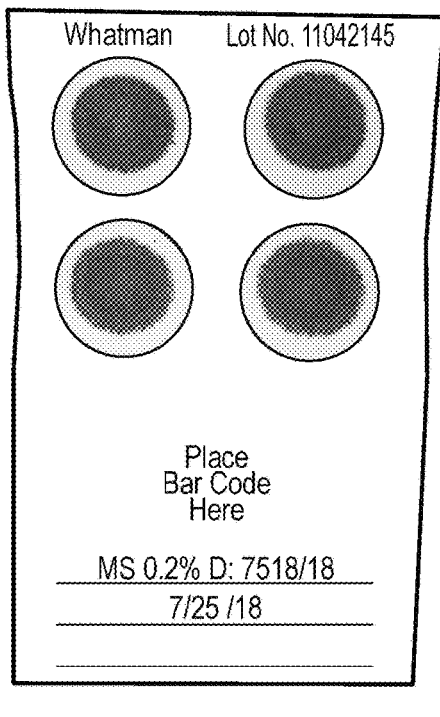
FIG. 14A
FIG. 14B

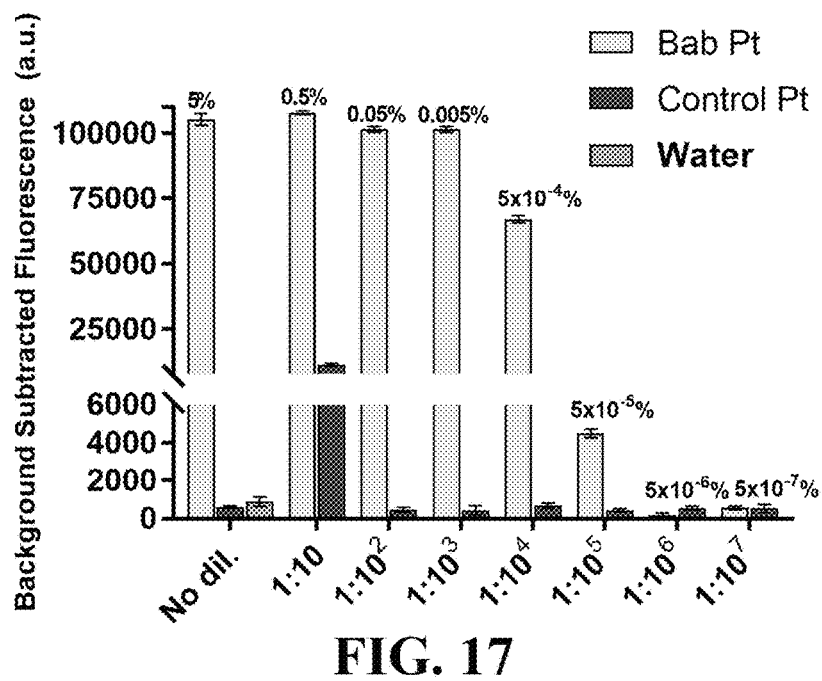
FIG. 17
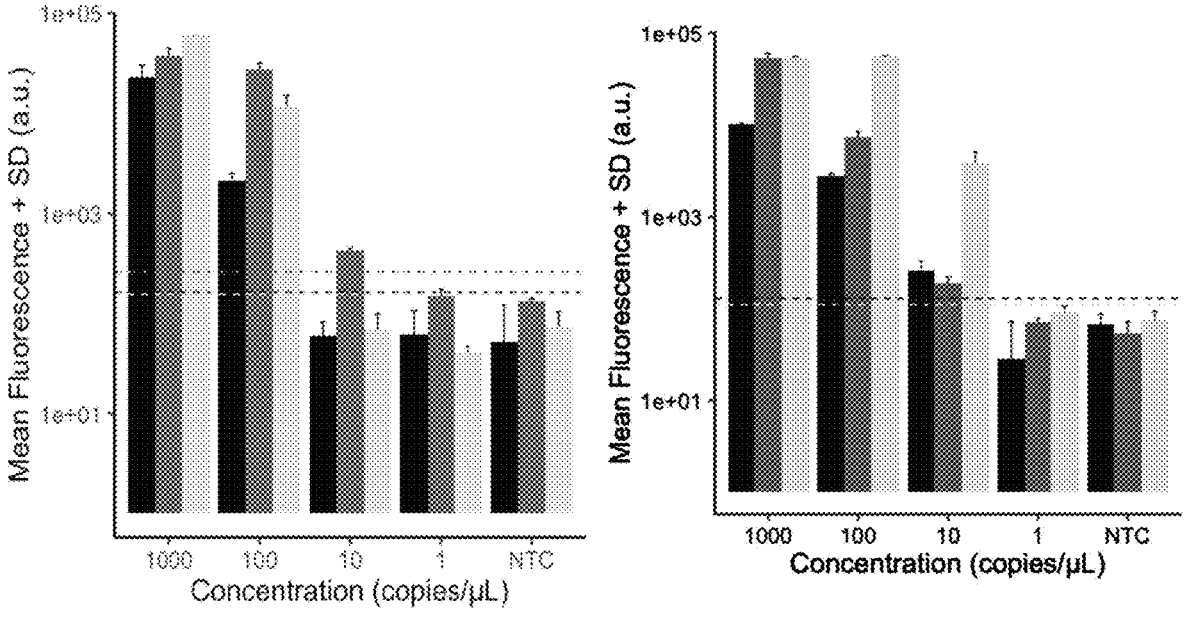
FIG. 18A                          FIG. 18B

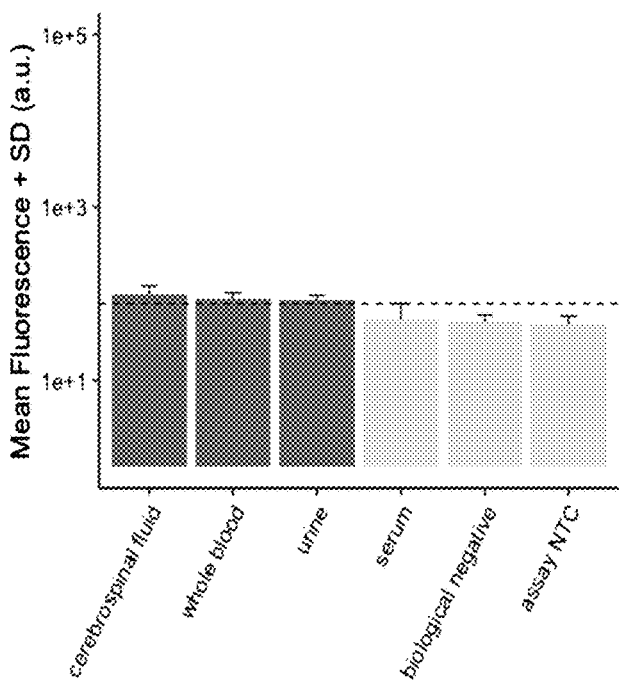
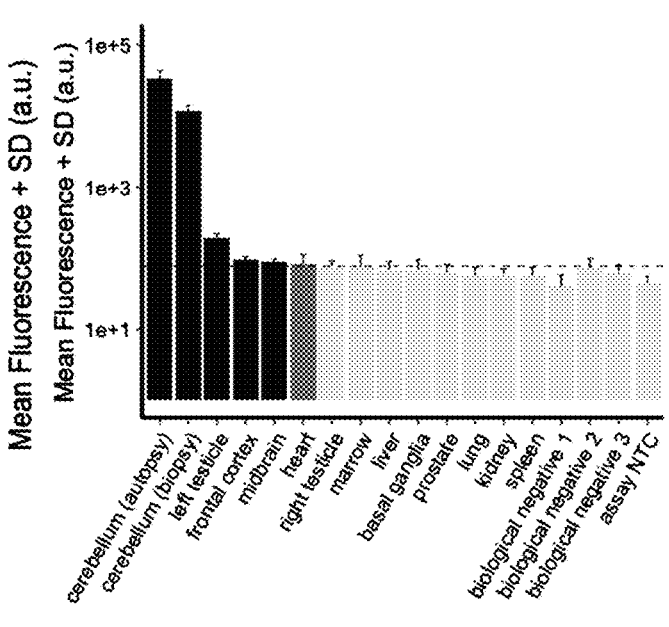
| Sample | SYBR qPCR POWV Copies/ul | POWV reads in low-depth sequencing (~1M reads/sample) |
|---|---|---|
| cerebellum (biopsy) | 4,736 | 648 |
| cerebellum (autopsy) | 21,148 | 3087 |
| right testicle | 1 | 10 |
| left testicle | 99 | 187 |
| lung | - | - |
| heart | - | - |
| liver | - | - |
| spleen | - | - |
| postate | - | - |
| kidney | - | - |
| marrow | - | - |
| midbrain | 14 | 2 |
| frontal cortex | 15 | 6 |
| basal ganglia | - | - |
| WaterCtl 071818 | - | - |
| WaterCtl 010719 | - | - |
| WaterCtl 010919 | - | - |
FIG. 19

FIG. 22C        FIG. 22D

```
                    SEQUENCE LISTING

<160> NUMBER OF SEQ ID NOS: 36

<210> SEQ ID NO 1
<211> LENGTH: 55
<212> TYPE: PRT
<213> ORGANISM: Babesia microti

<400> SEQUENCE: 1

Met Tyr Ala His Leu Ile Lys Gly Leu Trp Tyr Ser Cys Thr Tyr Leu
1               5                   10                  15

Pro Leu Ser Trp Tyr Thr Gly Ile Val Ile Leu Met Leu Ser Tyr Ala
            20                  25                  30
```

```
Ile Gly Phe Met Gly Tyr Val Leu Pro Tyr Gly Gln Ser Tyr Trp Gly
        35                  40                  45

Ala Thr Val Ile Ile Asn Leu
    50                  55

<210> SEQ ID NO 2
<211> LENGTH: 26
<212> TYPE: PRT
<213> ORGANISM: Babesia microti

<400> SEQUENCE: 2

Leu His Ile Val Pro Glu Trp Tyr Leu Leu Pro Phe Tyr Gly Thr Leu
1               5                   10                  15

Lys Leu Leu Pro Thr Lys Leu Ser Gly Leu
            20                  25

<210> SEQ ID NO 3
<211> LENGTH: 36
<212> TYPE: PRT
<213> ORGANISM: Babesia microti

<400> SEQUENCE: 3

Ser Lys Phe Asn Ser Ser Phe Ser Ser Lys Lys Ile Arg Ser Gln Lys
1               5                   10                  15

Ser Ser Gly Lys Ser Arg Ile Lys Thr Lys Ser Thr Asn Ile Phe Val
            20                  25                  30

Gly Gly Tyr Tyr
        35

<210> SEQ ID NO 4
<211> LENGTH: 48
<212> TYPE: PRT
<213> ORGANISM: Borrelia bavariensis

<400> SEQUENCE: 4

Met Tyr Val Ser Leu Ile Ala Asn Thr Ile Asp Phe Asp Lys Ile Asn
1               5                   10                  15

Tyr Ile Asn Ser Lys Met Leu Leu Asp Leu Ile Arg Asn Val Glu Leu
            20                  25                  30

Leu Val Leu Glu Phe Ala Lys Tyr Ser Asp Phe Lys Leu Gly Lys Ile
        35                  40                  45

<210> SEQ ID NO 5
<211> LENGTH: 87
<212> TYPE: PRT
<213> ORGANISM: Brucella abortis
<220> FEATURE:
<221> NAME/KEY: MISC_FEATURE
<222> LOCATION: (1)..(87)
<223> OTHER INFORMATION: X may represent any amino acid or may indicate
      a residue not present

<400> SEQUENCE: 5

Ser Pro Asp Met Ala Ile Leu Asn Leu Ser Val Leu Arg Gln Ala Lys
1               5                   10                  15

Thr Ala Arg Glu Ala Met Thr Ala Asn Asn Glu Ala Met Thr Lys Val
            20                  25                  30

Xaa Xaa Xaa Xaa Xaa Xaa Xaa Xaa Leu Asp Ala Met Lys Lys Ala Gly
        35                  40                  45

Ile Xaa Xaa Xaa Xaa Xaa Xaa Glu Asp Arg Asp Leu Gln Thr Gly Gly
    50                  55                  60
```

-continued

```
Ile Asp Ile Gln Pro Ile Tyr Val Tyr Pro Asp Asp Lys Asn Asn Leu
65                  70                  75                  80

Lys Glu Pro Thr Ile Thr Gly
                85
```

```
<210> SEQ ID NO 6
<211> LENGTH: 63
<212> TYPE: DNA
<213> ORGANISM: Babesia mictori
<220> FEATURE:
<221> NAME/KEY: misc_feature
<222> LOCATION: (1)..(63)
<223> OTHER INFORMATION: Sequence represents Babesia mictori cytB
      Consensus Sequence

<400> SEQUENCE: 6
ctrcgctatt ggcttcatgg gatatgtatt accatatggc caaatkagct actggggagc      60 tam                                                                    63
```

```
<210> SEQ ID NO 7
<211> LENGTH: 63
<212> TYPE: DNA
<213> ORGANISM: Babesia mictori
<220> FEATURE:
<221> NAME/KEY: misc_feature
<222> LOCATION: (1)..(63)
<223> OTHER INFORMATION: Sequence represents R1-2005

<400> SEQUENCE: 7
ctacgctatt ggcttcatgg gatatgtatt accatatggc caaatgagct actggggagc      60
tac                                                                    63
```

```
<210> SEQ ID NO 8
<211> LENGTH: 63
<212> TYPE: DNA
<213> ORGANISM: Babesia mictori
<220> FEATURE:
<221> NAME/KEY: misc_feature
<222> LOCATION: (1)..(63)
<223> OTHER INFORMATION: Sequence represents Gray-1971

<400> SEQUENCE: 8
ctacgctatt ggcttcatgg gatatgtatt accatatggc caaatgagct actggggagc      60
tac                                                                    63
```

```
<210> SEQ ID NO 9
<211> LENGTH: 63
<212> TYPE: DNA
<213> ORGANISM: Babesia mictori
<220> FEATURE:
<221> NAME/KEY: misc_feature
<222> LOCATION: (1)..(63)
<223> OTHER INFORMATION: Sequence represents Bab05-2014

<400> SEQUENCE: 9
ctacgctatt ggcttcatgg gatatgtatt accatatggc caaatgagct actggggagc      60
tac                                                                    63
```

```
<210> SEQ ID NO 10
<211> LENGTH: 63
<212> TYPE: DNA
<213> ORGANISM: Babesia mictori
<220> FEATURE:
<221> NAME/KEY: misc_feature
<222> LOCATION: (1)..(63)
```

-continued

```
<223> OTHER INFORMATION: Sequence represents Bab14-2015

<400> SEQUENCE: 10
ctgcgctatt ggcttcatgg gatatgtatt accatatggc caaatgagct actggggagc      60
tac                                                                     63

<210> SEQ ID NO 11
<211> LENGTH: 63
<212> TYPE: DNA
<213> ORGANISM: Babesia mictori
<220> FEATURE:
<221> NAME/KEY: misc_feature
<222> LOCATION: (1)..(63)
<223> OTHER INFORMATION: Sequence represents MGH-2001

<400> SEQUENCE: 11
ctacgctatt ggcttcatgg gatatgtatt accatatggc caaattagct actggggagc      60
tac                                                                     63

<210> SEQ ID NO 12
<211> LENGTH: 63
<212> TYPE: DNA
<213> ORGANISM: Babesia mictori
<220> FEATURE:
<221> NAME/KEY: misc_feature
<222> LOCATION: (1)..(63)
<223> OTHER INFORMATION: Sequence represents BWH-2003

<400> SEQUENCE: 12
ctacgctatt ggcttcatgg gatatgtatt accatatggc caaatgagct actggggagc      60
tac                                                                     63

<210> SEQ ID NO 13
<211> LENGTH: 63
<212> TYPE: DNA
<213> ORGANISM: Babesia mictori
<220> FEATURE:
<221> NAME/KEY: misc_feature
<222> LOCATION: (1)..(63)
<223> OTHER INFORMATION: Sequence represents MORNS-2015

<400> SEQUENCE: 13
ctacgctatt ggcttcatgg gatatgtatt accatatggc caaatgagct actggggagc      60
taa                                                                     63

<210> SEQ ID NO 14

<400> SEQUENCE: 14

000

<210> SEQ ID NO 15
<211> LENGTH: 70
<212> TYPE: DNA
<213> ORGANISM: Babesia mictori
<220> FEATURE:
<221> NAME/KEY: misc_feature
<222> LOCATION: (1)..(70)
<223> OTHER INFORMATION: Sequence represents Babesia mictori rpI4
      Consensus Sequence

<400> SEQUENCE: 15
aagtaaattt aatagttctt ttagttyaaa aaaaattaga tctcaaaaat cttcaggaaa      60 atcayrtata                                                              70
```

```
<210> SEQ ID NO 16
<211> LENGTH: 29
<212> TYPE: DNA
<213> ORGANISM: Babesia mictori
<220> FEATURE:
<221> NAME/KEY: misc_feature
<222> LOCATION: (1)..(29)
<223> OTHER INFORMATION: Sequence represents Bab.rpI4.R86C

<400> SEQUENCE: 16
atctcaaaaa tcttcaggaa aatcatgta                                      29

<210> SEQ ID NO 17
<211> LENGTH: 70
<212> TYPE: DNA
<213> ORGANISM: Babesia mictori
<220> FEATURE:
<221> NAME/KEY: misc_feature
<222> LOCATION: (1)..(70)
<223> OTHER INFORMATION: Sequence represents rpI4_RI

<400> SEQUENCE: 17
aagtaaattt aatagttctt ttagttcaaa aaaaattaga tctcaaaaat cttcaggaaa    60
atcacgtata                                                          70

<210> SEQ ID NO 18
<211> LENGTH: 70
<212> TYPE: DNA
<213> ORGANISM: Babesia mictori
<220> FEATURE:
<221> NAME/KEY: misc_feature
<222> LOCATION: (1)..(70)
<223> OTHER INFORMATION: Sequence represents rpI4_Bab05

<400> SEQUENCE: 18
aagtaaattt aatagttctt ttagttcaaa aaaaattaga tctcaaaaat cttcaggaaa    60
atcacatata                                                          70

<210> SEQ ID NO 19
<211> LENGTH: 70
<212> TYPE: DNA
<213> ORGANISM: Babesia mictori
<220> FEATURE:
<221> NAME/KEY: misc_feature
<222> LOCATION: (1)..(70)
<223> OTHER INFORMATION: Sequence represents rpI4_MORNS2...

<400> SEQUENCE: 19
aagtaaattt aatagttctt ttagtttaaa aaaaattaga tctcaaaaat cttcaggaaa    60
atcacatata                                                          70

<210> SEQ ID NO 20
<211> LENGTH: 46
<212> TYPE: DNA
<213> ORGANISM: Anaplasma phagocytphilum
<220> FEATURE:
<221> NAME/KEY: misc_feature
<222> LOCATION: (1)..(46)
<223> OTHER INFORMATION: Sequence represents16S guide Consensus Sequence

<400> SEQUENCE: 20
cactagaaat ggtgggtaat actgtataat ccctgcgggg gaaaga                   46

<210> SEQ ID NO 21
```

-continued

```
<211> LENGTH: 33
<212> TYPE: DNA
<213> ORGANISM: Anaplasma phagocytphillum
<220> FEATURE:
<221> NAME/KEY: misc_feature
<222> LOCATION: (1)..(33)
<223> OTHER INFORMATION: Sequence represents Anaplasma phagocytphilum
      metalloprotease guide Consensus Sequence

<400> SEQUENCE: 21
tccttctgcc gtatcgcatc accagwaygc ttt                                    33

<210> SEQ ID NO 22
<211> LENGTH: 33
<212> TYPE: DNA
<213> ORGANISM: Anaplasma phagocytphilum
<220> FEATURE:
<221> NAME/KEY: misc_feature
<222> LOCATION: (1)..(33)
<223> OTHER INFORMATION: Sequence represents Equi gBlock

<400> SEQUENCE: 22
tccttctgcc gtatcgcatc accagaacgc ttt                                    33

<210> SEQ ID NO 23
<211> LENGTH: 28
<212> TYPE: DNA
<213> ORGANISM: Anaplasma phagocytphilum
<220> FEATURE:
<221> NAME/KEY: misc_feature
<222> LOCATION: (1)..(28)
<223> OTHER INFORMATION: Sequence represents Equi Guide

<400> SEQUENCE: 23
cttctgccgt atcgcatcac cagtacgc                                          28

<210> SEQ ID NO 24
<211> LENGTH: 33
<212> TYPE: DNA
<213> ORGANISM: Anaplasma phagosytphilum
<220> FEATURE:
<221> NAME/KEY: misc_feature
<222> LOCATION: (1)..(33)
<223> OTHER INFORMATION: Sequence represents WT gBlock

<400> SEQUENCE: 24
tccttctgcc gtatcgcatc accagaatgc ttt                                    33

<210> SEQ ID NO 25
<211> LENGTH: 28
<212> TYPE: DNA
<213> ORGANISM: Anaplasma phagocytphilum
<220> FEATURE:
<221> NAME/KEY: misc_feature
<222> LOCATION: (1)..(28)
<223> OTHER INFORMATION: Sequence represents WT Guide

<400> SEQUENCE: 25
cttctgccgt atcgcatcac cagtatgc                                          28

<210> SEQ ID NO 26
<211> LENGTH: 48
<212> TYPE: DNA
<213> ORGANISM: Borrelia miyamotoi
<220> FEATURE:
<221> NAME/KEY: misc_feature
<222> LOCATION: (1)..(48)
<223> OTHER INFORMATION: Sequence represents Borrelia miyamotoi gIpQ
      guide
```

-continued

```
<400> SEQUENCE: 26
ccacaaatgt tgcacaatta tttcccaatc gagctagaga aaacggam                    48

<210> SEQ ID NO 27
<211> LENGTH: 48
<212> TYPE: DNA
<213> ORGANISM: Borrelia miyamotoi
<220> FEATURE:
<221> NAME/KEY: misc_feature
<222> LOCATION: (1)..(48)
<223> OTHER INFORMATION: Sequence represents Borrelia miyamotoi gIpQ
      guide

<400> SEQUENCE: 27
ccacaaatgt tgcacaatta tttcccaatc gagctagaga aaacggam                    48

<210> SEQ ID NO 28
<211> LENGTH: 48
<212> TYPE: DNA
<213> ORGANISM: Borrelia miyamotoi
<220> FEATURE:
<221> NAME/KEY: misc_feature
<222> LOCATION: (1)..(48)
<223> OTHER INFORMATION: Sequence represents Borrelia miyamotoi gIpQ
      guide

<400> SEQUENCE: 28
ccacaaatgt tgcacaatta tttcccaatc gagctagaga aaacggac                    48

<210> SEQ ID NO 29
<211> LENGTH: 51
<212> TYPE: DNA
<213> ORGANISM: Borrelia miyamotoi
<220> FEATURE:
<221> NAME/KEY: misc_feature
<222> LOCATION: (1)..(51)
<223> OTHER INFORMATION: Sequence represents Borrelia miyamotoi flab
      guide

<400> SEQUENCE: 29
tctgatgatg ctgctggtat gggtgttgct ggtaagctta attcacaaat t               51

<210> SEQ ID NO 30
<211> LENGTH: 57
<212> TYPE: RNA
<213> ORGANISM: Artificial Sequence
<220> FEATURE:
<223> OTHER INFORMATION: Synthetic

<400> SEQUENCE: 30
ucuagaaaua uggauuacuu gguagaacag caaucuacuc gaccugcagg caugcaa          57

<210> SEQ ID NO 31
<211> LENGTH: 64
<212> TYPE: RNA
<213> ORGANISM: Artificial Sequence
<220> FEATURE:
<223> OTHER INFORMATION: Synthetic

<400> SEQUENCE: 31
gauuuagacu accccaaaaa cgaaggggac uaaaacuaga uugcuguucu accaaguaau       60
ccau                                                                    64

<210> SEQ ID NO 32
<211> LENGTH: 25
```

-continued

```
<212> TYPE: RNA
<213> ORGANISM: Artificial Sequence
<220> FEATURE:
<223> OTHER INFORMATION: Synthetic

<400> SEQUENCE: 32
gggaacaaag cugaaguacu uaccc                                        25

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
gggtagggcg ggttggga                                               18

<210> SEQ ID NO 34
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Biotin tag /5Biosyg/
<220> FEATURE:
<221> NAME/KEY: misc_feature
<222> LOCATION: (12)..(12)
<223> OTHER INFORMATION: Iowa black quencher /3IAbRQSp/

<400> SEQUENCE: 34
ucucguacgu uc                                                     12

<210> SEQ ID NO 35
<211> LENGTH: 24
<212> TYPE: RNA
<213> ORGANISM: Artificial Sequence
<220> FEATURE:
<223> OTHER INFORMATION: Sythetic
<220> FEATURE:
<221> NAME/KEY: misc_feature
<222> LOCATION: (1)..(1)
<223> OTHER INFORMATION: Biotin Tag /5Biosg/
<220> FEATURE:
<221> NAME/KEY: misc_feature
<222> LOCATION: (24)..(24)
<223> OTHER INFORMATION: Iowa black quencher /3IAbRQSp/

<400> SEQUENCE: 35
ucucguacgu ucucucguac guuc                                        24

<210> SEQ ID NO 36
<211> LENGTH: 10
<212> TYPE: PRT
<213> ORGANISM: Unknown
<220> FEATURE:
<223> OTHER INFORMATION: Organism not provided
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
```

-continued

```
<400> SEQUENCE: 36

Asp Asn Xaa Ser Thr Xaa Xaa Xaa Arg Lys
1               5                   10
```

SHERLOCK ASSAYS FOR TICK-BORNE DISEASES

CROSS-REFERENCE TO RELATED APPLICATIONS

This application is the U.S. National Stage of International Application No. PCT/US2020/022776, filed Mar. 13, 2020, which claims the benefit of U.S. Provisional Application No. 62/818,739 filed Mar. 14, 2019 and U.S. Provisional Application 62/860,225 filed Jun. 11, 2019. The entire contents of the above-identified applications are hereby fully incorporated herein by reference.

STATEMENT REGARDING FEDERALLY SPONSORED RESEARCH

This invention was made with government support under Grant No. D18AC00006 awarded by the Department of Defense. The government has certain rights in the invention.

REFERENCE TO AN ELECTRONIC SEQUENCE LISTING

The contents of the electronic sequence listing (BROD-4100US_ST25.txt"; Size is 11,919 bytes and it was created on Nov. 5, 2024) is herein incorporated by reference in its entirety.

TECHNICAL FIELD

The subject matter disclosed herein is generally directed to rapid diagnostics related to the use of CRISPR effector systems.

BACKGROUND

Tick-borne diseases (TBD) such as Lyme disease (LD), babesiosis, and anaplasmosis have emerged over the past 40 years as a major threat to public health. *Borrelia burgdorferi*, the causative pathogen for LD, and co-infections are increasing in prevalence and expanding their geographic range. Poorly performing diagnostic assays have hampered our ability to detect and understand these pathogens. This is particularly true for LD, for which diagnostic tests are insensitive in acute infection and unreliable for LD-causing organisms outside of the United States (Branda et al. *Clin Infect Dis* 57 (3): 333-340 (2013); Makhani et al. *J Clin Microbiol* 49 (1): 455-457 (2011)).

The tick that transmits LD in the US, *Ixodes scapularis*, also transmits several other important tick-borne infections. *Babesia microti* and *Anaplasma phagocytophilum* infections can lead to shock and respiratory failure (Vannier et al. *NEJM* 366 (25): 2397-2407 (2012)). Powassan virus (POWV) infection can result in an often-fatal encephalitis (Ebel *Annu Rev Entomol* 55:95-110 (2010)). New tick-borne pathogens continue to be discovered or recognized, including Bourbon virus (Kosoy et al. *Emerg Infect Dis* 21 (5): 760-764 (2015)), Heartland virus (McMullan et al. *NEJM* 367 (9): 834-841 (2012)), *Borrelia miyamotoi* (Krause et al. nejm.org/doi/full/10.1056/NEJMc1215469 (2013); Gugliotta et al. *NEJM* 368 (3): 240-245 (2013)), *Borrelia mayonii* (Pritt et al. *Lancet Infect Dis* sciencedirect.com/science/article/pii/S1473309915004648 (2016)), and the *Ehrlichia muris*-like agent (Pritt et al. *NEJM* 365 (5): 422-429 (2011)). These infections can cause severe disease, but currently only limited information is understood about their pathogenesis.

Powassan virus, an emerging tick-borne flavivirus causes severe encephalitis and is transmitted by *Ixodes scapularis* ticks, with little known about strains that cause human infection.

Two major problems need to be addressed in the field of TBD. The first problem is insensitive diagnostics. Current serological testing for LD is unreliable, performs poorly in early infection, does not consistently distinguish between acute and prior infection or between strains, and cannot be used with confidence in immunocompromised individuals. More sensitive diagnostics are needed; these should be cheap, field deployable, and multiplexed, since tick-borne pathogens are frequently encountered as co-infections.

The second major problem is a lack of sequence- and strain-specific diagnostics and an incomplete understanding of the role of pathogen genetics in influencing clinical disease. Sequence-based diagnostics that identify the infective strain are needed. This is crucial in elucidating the pathogenic basis of heterogeneity in clinical manifestations of tick-borne disease. It would be useful to know why some patients experience severe central nervous system (CNS) disease or Lyme arthritis, and some experience only erythema migraines, whereas others have no rash at all. These patterns may be mediated by pathogen genes.

There is a critical need for rapid, sensitive, sequence-specific, point-of-care (POC) diagnostics to guide treatment of TBD.

SUMMARY

In certain example embodiments, the invention provides a nucleic acid detection system comprising a detection CRISPR system having an effector protein and one or more guide RNAs each designed to bind to corresponding target molecules that are diagnostic for a tick-borne disease state; and an RNA-based masking construct.

In some embodiments, the detection system may comprise i) two or more CRISPR systems, each CRISPR system comprising an effector protein and a guide RNA designed to bind to a corresponding target molecule that is diagnostic for a tick-borne disease state; and ii) a set of detection constructs, each detection construct comprising a cutting motif sequence that is preferentially cut by one of the activated CRISPR effector proteins.

In some embodiments, guide RNAs may be designed to bind to *Babesia microti, A. phagocytophilum*, and/or *Borrelia miyamotoi*. In some embodiments, the guide RNAs may be designed to bind to the cytB region of *Babesia microti*, the 16S rRNA gene of *A. phagocytophilum*, and/or the cytB gene of *B. miyamotoi*. In some embodiments, the guide RNAs may be designed to detect variants of *Babesia microti*. In some embodiments, the guide RNA may be designed to bind to *B. microti* atovaquone-binding region of cytB. In some embodiments, the guide RNAs wherein the guide RNAs comprise 95% sequence identity to 28 continuous nucleotides of one of SEQ ID NOs: 6-29.

In some embodiments, guide RNAs may be designed to bind to a flavivirus. The flavivirus can be Powassan virus (POWV). In embodiments, the guide RNA is designed to bind to the NS5 gene of POWV.

In some embodiments, the detection system may further comprise nucleic acid amplification reagents.

In some embodiments, the target molecule may be target DNA. In some embodiments, the target molecule comprises a SNP.

In some embodiments, the guide RNA may be designed to bind to *B. microti* comprising a SNP cytB M134I.

In another aspect, the invention provides a lateral flow device comprising the nucleic acid detection system described above.

In some embodiments, the CRISPR system may be freeze-dried on the lateral flow strip.

In some embodiments, the lateral flow device comprises a substrate comprising a first end, wherein the first end comprises a sample loading portion and a first region loaded with a detectable ligand, the nucleic acid detection system, a first capture region comprising a first binding agent, and a second capture region comprising a second binding agent.

In some embodiments, the sample loading portion comprises a receiving input for a blood stick.

In some embodiments, the sample loading portion further comprises one or more amplification reagents to amplify the one or more target molecules. The reagents may optionally comprise reagents for nucleic acid sequence-based amplification (NASBA), recombinase polymerase amplification (RPA), loop-mediated isothermal amplification (LAMP), strand displacement amplification (SDA), helicase-dependent amplification (HDA), nicking enzyme amplification reaction (NEAR), PCR, multiple displacement amplification (MDA), rolling circle amplification (RCA), ligase chain reaction (LCR), or ramification amplification method (RAM).

In some embodiments, the RNA construct may comprise a first molecule on a first end and a second molecule on a second end. The first molecule may be FITC and the second molecule may be biotin, or vice versa.

In some embodiments, the first capture region may comprise a first binding agent that specifically binds the first molecule of the reporter construct. In some embodiments, the first binding agent may be an antibody that is fixed or otherwise immobilized to the first capture region.

In some embodiments, the second capture region may comprise a second binding agent that specifically binds the second molecule of the reporter construct, or the detectable ligand. In some embodiments, the second binding agent may be an antibody or an antibody-binding protein that is fixed or otherwise immobilized to the second capture region.

In another aspect, the invention provides a method for detecting target nucleic acids in a sample, comprising distributing a sample or set of samples into one or more individual discrete volumes, the individual discrete volumes comprising the nucleic acid detection system of any of the previous claims.

In some embodiments, the sample may be blood, RBC supernatant, plasma, cerebrospinal fluid.

In some embodiments, the method may further comprise the steps of i) incubating the sample at 37-50° C. for 5-20 minutes; ii) incubating the sample at 64-95° C. for 5 minutes; iii) performing RT-RPA; iv) performing T7 transcription; and v) detecting the target nucleic acids.

In some embodiments, the method may comprise treating the sample with heat, optionally at 99° C. for 10 minutes.

In some embodiments, the target nucleic acid may be from a sample of cell free DNA. In some embodiments, the target nucleic acid may be DNA and the method may further comprise the step of extracting DNA from cells in the sample.

In some embodiments, the sample may be collected on a Whatman FTA card. In some embodiments, the method may further comprise eluting the sample from the FTA card.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 5A-5C—Coverage of (5A) B. microti mitochondrion, (5B) B. microti apicoplast, and (5C) B. microti chromosome 1 from a patient sample.

FIGS. 7A-7C-shows clinically relevant variants in the *B. microti* genome used as a basis for crRNA guides with SNP detection capabilities, Lemieux et al., 2016. FIG. 7A Genome wide P values for increased rate of non-synonymous variants among relapsing cases; FIG. 7B cytB mutations identified in relapsing cases of human *B. microti* babesiosis are shown in a multiple sequence alignment with the *B. microti* reference. Highlighting ranges from purple to yellow, indicated greater to less conservation based on amino acid identity and physicochemical properties. Mutations associated with atovaquone resistance in other Apicomplexa (P *Plasmodium* spp., T *Toxoplasma gondii*, G *Babesia gibsoni*) are also indicated (SEQ ID NOS: 1 and 2). FIG. 7C Variants in RPL4 associated with relapse in *B. microti* are shown as in 7B. Also shown are variants associated with azithromycin resistance in *P. falciparum* (P) *S. pneumoniae*(s) and *E. coli* (E) (SEQ ID NO: 3).

FIG. 13—Testing for Cell Free *B. microti* DNA Plasma, not whole blood or red blood cell fraction—Applicants have access to different patient samples, which is the best? Based on results of Akter et al. 2018 paper "Potential of cell-free DNA as a screening marker for parasite infections in dog." Genomics. doi: 10.1016/j.ygeno.2018.05.020 showing cell free DNA in dogs, hypothesized that there was *babesia* free DNA in the plasma, and extracellular bab. Cool result, nobody tests for *babesia* in plasma or serum (serology is not a good test).

FIGS. 14A-14B—Simplifying Sample Collection and Processing. (14A) Whatman FT card collection; (14B) Sample evaluation from FTA Card, FTA Eluate versus control.

FIG. 17—Limit of Detection with diluted patient samples, extracted DNA.

FIG. 18A—Development of a SHERLOCK assay targeting the POWV NS5 gene. FIG. 18A—RNA template bar plot shows fluorescent output (y-axis) using synthetic IVT RNA input across a range of concentrations (x-axis). Each bar represents the mean (and SD) of 3 technical replicates in a single experiment; the assay was repeated in three independent experiments (black, dark grey, light grey). For each experiment, the threshold for positivity was defined as 3 SD above the mean fluorescence for the NTC (dashed horizontal lines). Based on these experiments, the assay LOD was defined as 100 copies/µL of RNA. FIG. 18B Bar plot of DNA template for determination of LOD.

FIG. 19—Screening of primary RNA samples from Subject A (upper panel) and Subject B (lower panel) by POWV SHERLOCK. Positive samples are indicated in black. Equivocal samples (standard deviation crosses the threshold for positivity) are indicated in dark grey. Negative samples are indicated in light grey. Subject B SYBR qPCR and low-depth sequencing confirms SHERLOCK positive detection (lower right panel).

FIG. 22A-22D—FIG. 22A schematic of SHERLOCK detection; FIG. 22B target site of ssRNA with crRNA sequence designed for target sequence (SEQ ID NOs: 30 and 31); FIG. 22C SHERLOCK detection with ssRNA concentration in aM with background subtracted fluorescence; FIG. 22D detection of ssDNA concentration in aM with background subtracted fluorescence.

Figures 1A, 1B, 1C, 1D, 1E, 2A, 2B, 2C, 2D, 2E:
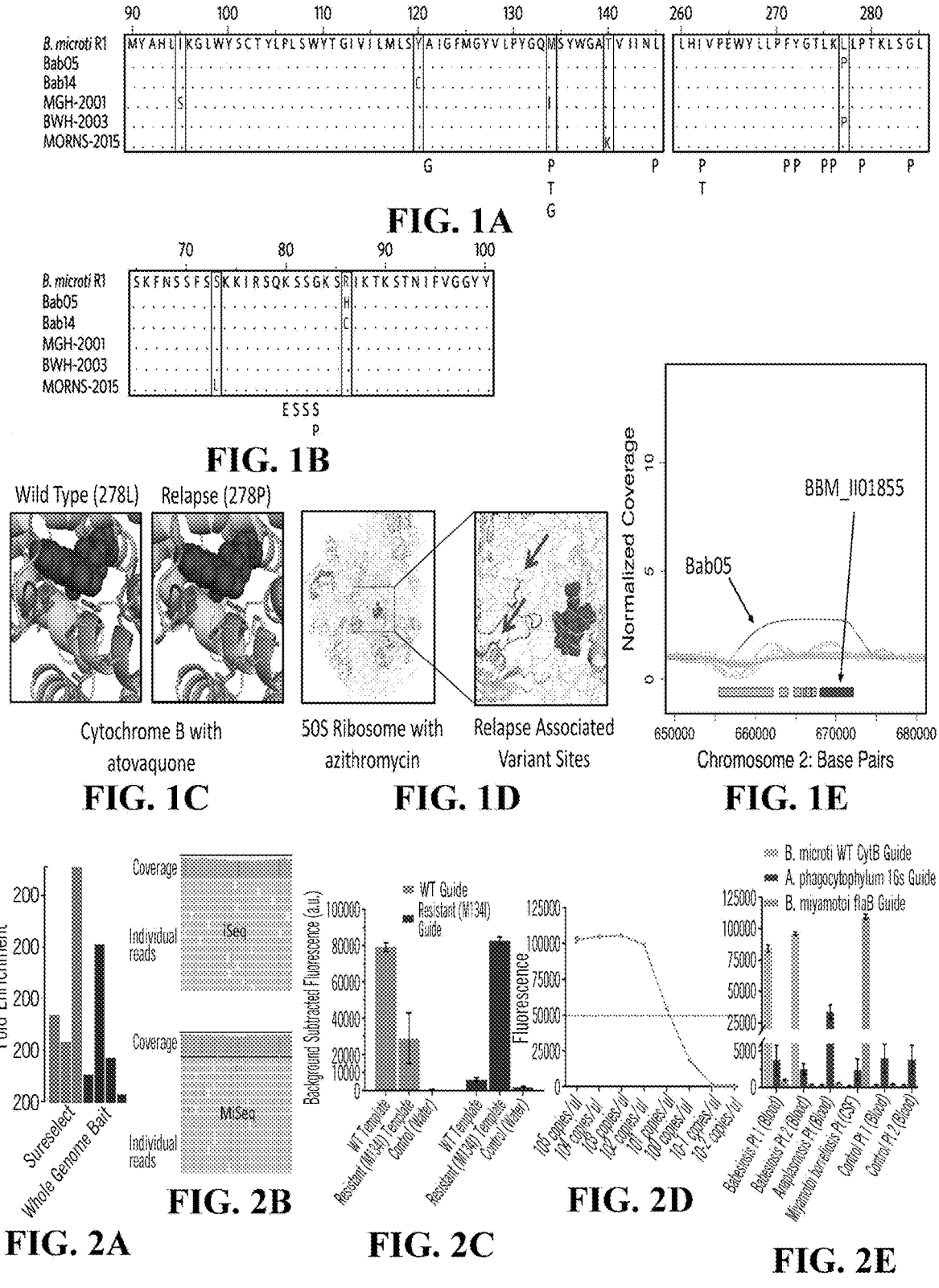
FIG. 1A-1E-Relapsing babesiosis (SEQ ID NOS: 1 and 2) cases contain substitutions in cytB (1A) and rpl4 (1B) (SEQ ID NO: 3—Babesiosis) resembling drug resistance variants in other organisms (Plasmodium—amino acids marked with P, Toxoplasma—T, Babesia gibsoni—G, E. coli (E), and S. pneumoniae—S). (1C) Modeling of variants in cytB (wild type shown in green; variant in gray, the highly conserved PEWY motif is colored blue; known variants in malaria are orange) and rpl4 (wild type amino acids in pink; variants in gray) shows adjacency to binding pockets for atovaquone and (1D) azithromycin. (1E) One relapsing case contained a 3-fold amplification of a locus containing BBM_II01855, an ABC transporter with homology to PfMDR, a transporter involved in multiple drug resistance in P. falciparum.
FIG. 2A-2E—(2A) Fold enrichment B. microti DNA as measured by Illumina sequencing, using hybrid selection with commercial (Agilent Sureselect, in green) and custom amplified whole-genome baits, in blue. (2B) Short read alignment to the B. burgdorferi chromosome with IGV104, displaying integrated coverage, reads, and variants calls (in color) for iSeq and MiSeq for an arbitrary 500 base region, showing identical variant calls and excellent coverage with both platforms. (2C) SHERLOCK assays for B. microti showing SNP-specific guide RNAs can distinguish between an atovaquone-resistance variant and the wild-in type allele in B. microti. (2D) The B. microti assay has high sensitivity. (2E) SHERLOCK assays can be extended to other TBD, including B. miyamotoi and A. phagocytophilum, by changing the RPA primers and guide RNAs.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M.J. MacPherson, B. D. Hames, and G. R. Taylor eds.): Antibodies, A Laboratory Manual (1988) (Harlow and Lane, eds.): Antibodies A Laboraotry Manual, $2^{nd}$ edition 2013 (E.A. Greenfield ed.); Animal Cell Culture (1987) (R.I. Freshney, ed.); Benjamin Lewin, Genes IX, published by Jones and Bartlet, 2008 (ISBN 0763752223); Kendrew et al.

(eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011)

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

"C2c2" is now referred to as "Cas13a", and the terms are used interchangeably herein unless indicated otherwise.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The embodiments disclosed herein utilize RNA or DNA targeting effectors to provide a robust CRISPR-based diagnostic with attomolar sensitivity. Embodiments disclosed herein can detect both DNA and RNA with comparable levels of sensitivity and can differentiate targets from non-targets based on single base pair differences. Moreover, the embodiments disclosed herein can be prepared in freeze-dried format for convenient distribution and point-of-care (POC) applications. Such embodiments are useful in multiple scenarios in human health including, for example, viral detection, bacterial strain typing, sensitive genotyping, and detection of disease-associated cell free DNA. In certain embodiments, the present invention is used for rapid detection of tick-borne pathogens using guide RNAs specific to a pathogen (e.g., *Babesia microti, Anaplasma phagocytophilum, Borrelia miyamotoi*).

Nucleic Acid Detection Systems

In some embodiments, the invention provides a nucleic acid detection system. The system may comprise a detection CRISPR system having an effector protein and one or more guide RNAs each designed to bind to corresponding target molecules that are diagnostic for a tick-borne disease state. The system may also comprise an RNA-based masking construct. In certain example embodiments, the assays may comprise multiple Cas12 orthologs or one or more orthologs in combination with one or more Cas13 orthologs. In certain example embodiments, the Cas12 orthologs are Cas12a, Cas12b, or Cas12c orthologs. In certain embodiments, the Cas13 orthologs are Cas13a or Cas13b orthologs.

CRISPR Effector Proteins

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). When the CRISPR protein is a C2c2 protein, a tracrRNA is not required. C2c2 has been described in Abudayyeh et al. (2016) "C2c2 is a single-component programmable RNA-guided d RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.mol-cel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein His A, C or U. In certain embodiments, the effector protein may be *Leptotrichia shahii* C2c2p, more preferably *Leptotrichia shahii* DSM 19757 C2c2, and 3' PAM is a 5' H.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target RNA may be an RNA polynucleotide or a part of an RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

The nucleic acid molecule encoding a CRISPR effector protein, in particular C2c2, is advantageously codon optimized CRISPR effector protein. An example of a codon optimized sequence is in this instance a sequence optimized for expression in eukaryotes, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprises one or more HEPN domains comprising an RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems"

filed on Mar. 15, 2017, and U.S. Provisional Patent Application 62/484,786 entitled "Novel Type VI CRISPR Orthologs and Systems," and filed on Apr. 12, 2017.

In an embodiment of the invention, a HEPN domain comprises at least one RxxxxH motif comprising the sequence of R{N/H/K}X1X2X3H In an embodiment of the invention, a HEPN domain comprises a RxxxxH motif comprising the sequence of R{N/H}X1X2X3H In an embodiment of the invention, a HEPN domain comprises the sequence of R{N/K}X1X2X3H In certain embodiments, X1 is R, S, D, E, Q, N, G, Y, or H. In certain embodiments, X2 is I, S, T, V, or L. In certain embodiments, X3 is L, F, N, Y, V, I, S, D, E, or A.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related or are only partially structurally related. An "orthologue" of a protein as used herein is a protein of a different species which performs the same or a similar function as the protein it is an orthologue of. Orthologous proteins may but need not be structurally related or are only partially structurally related.

In particular embodiments, the Type VI RNA-targeting Cas enzyme is C2c2. In other example embodiments, the Type VI RNA-targeting Cas enzyme is Cas 13b. In particular embodiments, the homologue or orthologue of a Type VI protein such as C2c2 as referred to herein has a sequence homology or identity of at least 30%, or at least 40%, or at least 50%, or at least 60%, or at least 70%, or at least 80%, more preferably at least 85%, even more preferably at least 90%, such as for instance at least 95% with a Type VI protein such as C2c2 (e.g., based on the wild-type sequence of any of *Leptotrichia shahii* C2c2, Lachnospiraceae bacterium MA2020 C2c2, Lachnospiraceae bacterium NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, Listeriaceae bacterium (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2). In further embodiments, the homologue or orthologue of a Type VI protein such as C2c2 as referred to herein has a sequence identity of at least 30%, or at least 40%, or at least 50%, or at least 60%, or at least 70%, or at least 80%, more preferably at least 85%, even more preferably at least 90%, such as for instance at least 95% with the wild type C2c2 (e.g., based on the wild-type sequence of any of *Leptotrichia shahii* C2c2, Lachnospiraceae bacterium MA2020 C2c2, Lachnospiraceae bacterium NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, Listeriaceae bacterium (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2).

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional 62/432,240 entitled "Novel Crispr Enzymes and Systems" filed Dec. 8, 2016. Reference is further made to East-Seletsky et al. "Two distinct RNase activities of CRISPR-C2c2 enable guide-RNA processing and RNA detection" Nature doi: 10/1038/nature19802 and Abudayyeh et al. "C2c2 is a single-component programmable RNA-guided RNA targeting CRISPR effector" bioRxiv doi: 10.1101/054742.

RNase function in CRISPR systems is known, for example mRNA targeting has been reported for certain type III CRISPR-Cas systems (Hale et al., 2014, *Genes Dev*, vol. 28, 2432-2443; Hale et al., 2009, Cell, vol. 139, 945-956; Peng et al., 2015, *Nucleic acids research*, vol. 43, 406-417) and provides significant advantages. In the *Staphylococcus epidermis* type III-A system, transcription across targets results in cleavage of the target DNA and its transcripts, mediated by independent active sites within the Cas10-Csm ribonucleoprotein effector protein complex (see, Samai et al., 2015, *Cell*, vol. 151, 1164-1174). A CRISPR-Cas system, composition or method targeting RNA via the present effector proteins is thus provided.

In an embodiment, the Cas protein may be a C2c2 ortholog of an organism of a genus which includes but is not limited to *Leptotrichia, Listeria, Corynebacterium, Sutterella, Legionella, Treponema, Filifactor, Eubacterium, Streptococcus, Lactobacillus, Mycoplasma, Bacteroides, Flavivirus, Flavobacterium, Sphaerochaeta, Azospirillum, Gluconacetobacter, Neisseria, Roseburia, Parvibaculum, Staphylococcus, Nitratifractor, Mycoplasma* and *Campylobacter*. Species of organisms of such a genus can be as otherwise herein discussed.

Some methods of identifying orthologues of CRISPR-Cas system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Leptotrichia, Listeria, Corynebacterium, Sutterella, Legionella, Treponema, Filifactor, Eubacterium, Streptococcus, Lactobacillus, Mycoplasma, Bacteroides, Flavivirus, Flavobacterium, Sphaerochaeta, Azospirillum, Gluconacetobacter, Neisseria, Roseburia, Parvibaculum, Staphylococcus, Nitratifractor, Mycoplasma* and *Campylobacter*. A chimeric enzyme can comprise a first fragment and a second fragment, and the fragments can be of CRISPR enzyme orthologs of organisms of genera herein mentioned or of species herein mentioned; advantageously the fragments are from CRISPR enzyme orthologs of different species.

In embodiments, the C2c2 protein as referred to herein also encompasses a functional variant of C2c2 or a homologue or an orthologue thereof. A "functional variant" of a protein as used herein refers to a variant of such protein which retains at least partially the activity of that protein. Functional variants may include mutants (which may be insertion, deletion, or replacement mutants), including polymorphs, etc. Also included within functional variants are fusion products of such protein with another, usually unrelated, nucleic acid, protein, polypeptide or peptide. Functional variants may be naturally occurring or may be manmade. Advantageous embodiments can involve engineered or non-naturally occurring Type VI RNA-targeting effector proteins.

In an embodiment, nucleic acid molecule(s) encoding the C2c2 or an ortholog or homolog thereof, may be codon-optimized for expression in a eukaryotic cell. A eukaryote can be as herein discussed. Nucleic acid molecule(s) can be engineered or non-naturally occurring.

In an embodiment, the C2c2 or an ortholog or homolog thereof, may comprise one or more mutations (and hence nucleic acid molecule(s) coding for same may have mutation(s). The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains.

In an embodiment, the C2c2 or an ortholog or homolog thereof, may comprise one or more mutations. The mutations may be artificially introduced mutations and may include but are not limited to one or more mutations in a catalytic domain. Examples of catalytic domains with reference to a Cas enzyme may include but are not limited to HEPN domains.

In an embodiment, the C2c2 or an ortholog or homolog thereof, may be used as a generic nucleic acid binding protein with fusion to or being operably linked to a functional domain. Exemplary functional domains may include but are not limited to translational initiator, translational activator, translational repressor, nucleases, in particular ribonucleases, a spliceosome, beads, a light inducible/controllable domain or a chemically inducible/controllable domain.

In certain example embodiments, the C2c2 effector protein may be from an organism selected from the group consisting of: *Leptotrichia, Listeria, Corynebacterium, Sutterella, Legionella, Treponema, Filifactor, Eubacterium, Streptococcus, Lactobacillus, Mycoplasma, Bacteroides, Flavivirus, Flavobacterium, Sphaerochaeta, Azospirillum, Gluconacetobacter, Neisseria, Roseburia, Parvibaculum, Staphylococcus, Nitratifractor, Mycoplasma*, and *Campylobacter.*

In certain embodiments, the effector protein may be a *Listeria* sp. C2c2p, preferably *Listeria seeligeri* C2c2p, more preferably *Listeria seeligeri* serovar 1/2b str. SLCC3954 C2c2p and the crRNA sequence may be 44 to 47 nucleotides in length, with a 5' 29-nt direct repeat (DR) and a 15-nt to 18-nt spacer.

In certain embodiments, the effector protein may be a *Leptotrichia* sp. C2c2p, preferably *Leptotrichia shahii* C2c2p, more preferably *Leptotrichia shahii* DSM 19757 C2c2p and the crRNA sequence may be 42 to 58 nucleotides in length, with a 5' direct repeat of at least 24 nt, such as a 5' 24-28-nt direct repeat (DR) and a spacer of at least 14 nt, such as a 14-nt to 28-nt spacer, or a spacer of at least 18 nt, such as 19, 20, 21, 22, or more nt, such as 18-28, 19-28, 20-28, 21-28, or 22-28 nt.

In certain example embodiments, the effector protein may be a *Leptotrichia* sp., *Leptotrichia wadei* F0279, or a *Listeria* sp., preferably *Listeria newyorkensis* FSL M6-0635.

In certain example embodiments, the C2c2 effector proteins of the invention include, without limitation, the following 21 ortholog species (including multiple CRISPR loci: *Leptotrichia shahii; Leptotrichia wadei* (Lw2); *Listeria seeligeri*; Lachnospiraceae bacterium MA2020; Lachnospiraceae bacterium NK4A179; [*Clostridium*] *aminophilum* DSM 10710; *Carnobacterium gallinarum* DSM 4847; *Carnobacterium gallinarum* DSM 4847 (second CRISPR Loci); *Paludibacter propionicigenes* WB4; *Listeria weihenstephanensis* FSL R9-0317; Listeriaceae bacterium FSL M6-0635; *Leptotrichia wadei* F0279; *Rhodobacter capsulatus* SB 1003; *Rhodobacter capsulatus* R121; *Rhodobacter capsulatus* DE442; *Leptotrichia buccalis* C-1013-b; Herbinix hemicellulosilytica; [*Eubacterium*] *rectale*; Eubacteriaceae bacterium CHKCI004; *Blautia* sp. Marseille-P2398; and *Leptotrichia* sp. oral taxon 879 str. F0557. Twelve (12) further non-limiting examples are: Lachnospiraceae bacterium NK4A144; Chloroflexus aggregans; *Demequina aurantiaca; Thalassospira* sp. TSL5-1; *Pseudobutyrivibrio* sp. OR37; *Butyrivibrio* sp. YAB3001; *Blautia* sp. Marseille-P2398; *Leptotrichia* sp. Marseille-P3007; *Bacteroides* ihuae; Porphyromonadaceae bacterium KH3CP3RA; *Listeria riparia*; and *Insolitispirillum peregrinum*.

In certain embodiments, the C2c2 protein according to the invention is or is derived from one of the orthologues as described in the table below, or is a chimeric protein of two or more of the orthologues as described in the table below, or is a mutant or variant of one of the orthologues as described in the table below (or a chimeric mutant or variant), including dead C2c2, split C2c2, destabilized C2c2, etc. as defined herein elsewhere, with or without fusion with a heterologous/functional domain.

In certain embodiments, a nucleic acid sequence encoding the C2c2 protein is provided.

In an embodiment of the invention, there is provided effector protein which comprises an amino acid sequence having at least 80% sequence homology to the wild-type sequence of any of *Leptotrichia shahii* C2c2, Lachno-spiraceae bacterium MA2020 C2c2, Lachnospiraceae bacterium NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, Listeriaceae bacterium (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2.

In an embodiment of the invention, the effector protein comprises an amino acid sequence having at least 80% sequence homology to a Type VI effector protein consensus sequence including, but not limited to a sequence described herein. According to the invention, a consensus sequence can be generated from multiple C2c2 orthologs, which can assist in locating conserved amino acid residues, and motifs, including but not limited to, catalytic residues and HEPN motifs in C2c2 orthologs that mediate C2c2 function.

In another non-limiting example, a sequence alignment tool to assist generation of a consensus sequence and identification of conserved residues is the MUSCLE alignment tool (ebi.ac.uk/Tools/msa/muscle/). For example, using MUSCLE, the following amino acid locations conserved among C2c2 orthologs can be identified in *Leptotrichia wadei* C2c2: K2; K5; V6; E301; L331; I335; N341; G351; K352; E375; L392; L396; D403; F446; I466; I470; R474 (HEPN); H475; H479 (HEPN), E508; P556; L561; I595; Y596; F600; Y669; I673; F681; L685; Y761; L676; L779; Y782; L836; D847; Y863; L869; I872; K879; I933; L954; I958; R961; Y965; E970; R971; D972; R1046 (HEPN), H1051 (HEPN), Y1075; D1076; K1078; K1080; I1083; I1090.

An exemplary sequence alignment of HEPN domains showing highly conserved residues can be utilized to identify HEPN domain sequences that can be used according to the present invention. In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, an N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from Bergeyella zoohelcum.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

Cas12 Proteins

Cas12a Orthologs

The present invention encompasses the use of a Cas12a (also referred to as Cpf1) effector protein, derived from a Cpf1 locus denoted as subtype V-A. Herein such effector proteins are also referred to as "Cpf1p", e.g., a Cpf1 protein (and such effector protein or Cpf1 protein or protein derived from a Cpf1 locus is also called "CRISPR enzyme"). Presently, the subtype V-A loci encompass cas1, cas2, a distinct gene denoted cpf1 and a CRISPR array. Cas12 a (CRISPR-associated protein Cpf1, subtype PREFRAN) is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in all Cas9 proteins, and the RuvC-like domain is contiguous in the Cpf1 sequence, in contrast to Cas9 where it contains long inserts including the HNH domain. Accordingly, in particular embodiments, the CRISPR-Cas enzyme comprises only a RuvC-like nuclease domain.

The programmability, specificity, and collateral activity of the RNA-guided Cpf1 also make it an ideal switchable nuclease for non-specific cleavage of nucleic acids. In one embodiment, a Cpf1 system is engineered to provide and take advantage of collateral non-specific cleavage of RNA. In another embodiment, a Cpf1 system is engineered to provide and take advantage of collateral non-specific cleavage of ssDNA. Accordingly, engineered Cpf1 systems provide platforms for nucleic acid detection and transcriptome manipulation. Cpf1 is developed for use as a mammalian transcript knockdown and binding tool. Cpf1 is capable of robust collateral cleavage of RNA and ssDNA when activated by sequence-specific targeted DNA binding.

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related or are only partially structurally related. An "orthologue" of a protein as used herein is a protein of a different species which performs the same or a similar function as the protein it is an orthologue of. Orthologous proteins may but need not be structurally related or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22 (4): 359-66. doi: 10.1002/pro.2225.). See also Shmakov et al. (2015) for application in the field of CRISPR-Cas loci. Homologous proteins may but need not be structurally related or are only partially structurally related.

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this putative novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cpf1 is denoted to be in subtype V-A to distinguish it from C2c1p which does not have an identical domain structure and is hence denoted to be in subtype V-B.

In particular embodiments, the effector protein is a Cpf1 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridium, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus.*

In further particular embodiments, the Cpf1 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii.*

The effector protein may comprise a chimeric effector protein comprising a first fragment from a first effector protein (e.g., a Cpf1) ortholog and a second fragment from a second effector (e.g., a Cpf1) protein ortholog, and wherein the first and second effector protein orthologs are different. At least one of the first and second effector protein (e.g., a Cpf1) orthologs may comprise an effector protein (e.g., a Cpf1) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridium, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*; e.g., a chimeric effector protein comprising a first fragment and a second fragment wherein each of the first and second fragments is selected from a Cpf1 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridium, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus* wherein the first and second fragments are not from the same bacteria; for instance a chimeric effector protein comprising a first fragment and a second fragment wherein each of the first and second fragments is selected from a Cpf1 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae;*

*L. monocytogenes, L. ivanovii; C. botulinum, C. difficile, C. tetani, C. sordellii; Francisella tularensis* 1, *Prevotella albensis,* Lachnospiraceae bacterium MC2017 1. *Butyrivibrio proteoclasticus,* Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai,* Lachnospiraceae bacterium ND2006, *Porphyromonas crevioricanis* 3, *Prevotella disiens* and *Porphyromonas macacae,* wherein the first and second fragments are not from the same bacteria.

In a more preferred embodiment, the Cpf1p is derived from a bacterial species selected from *Francisella tularensis* 1, *Prevotella albensis,* Lachnospiraceae bacterium MC2017 1. *Butyrivibrio proteoclasticus,* Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum, Eubacterium eligens, Moraxella bovoculi* 237, *Leptospira inadai,* Lachnospiraceae bacterium ND2006, *Porphyromonas crevioricanis* 3, *Prevotella disiens* and *Porphyromonas macacae.* In certain embodiments, the Cpf1p is derived from a bacterial species selected from *Acidaminococcus* sp. BV3L6, Lachnospiraceae bacterium MA2020. In certain embodiments, the effector protein is derived from a subspecies of *Francisella tularensis* 1, including but not limited to *Francisella tularensis* subsp. *Novicida.*

In some embodiments, the Cpf1p is derived from an organism from the genus of *Eubacterium.* In some embodiments, the CRISPR effector protein is a Cpf1 protein derived from an organism from the bacterial species of *Eubacterium rectale.* In some embodiments, the amino acid sequence of the Cpf1 effector protein corresponds to NCBI Reference Sequence WP_055225123.1, NCBI Reference Sequence WP_055237260.1, NCBI Reference Sequence WP_055272206.1, or GenBank ID OLA16049.1. In some embodiments, the Cpf1 effector protein has a sequence homology or sequence identity of at least 60%, more particularly at least 70, such as at least 80%, more preferably at least 85%, even more preferably at least 90%, such as for instance at least 95%, with NCBI Reference Sequence WP_055225123.1, NCBI Reference Sequence WP_055237260.1, NCBI Reference Sequence WP_055272206.1, or GenBank ID OLA16049.1. The skilled person will understand that this includes truncated forms of the Cpf1 protein whereby the sequence identity is determined over the length of the truncated form. In some embodiments, the Cpf1 effector recognizes the PAM sequence of TTTN or CTTN.

In particular embodiments, the homologue or orthologue of Cpf1 as referred to herein has a sequence homology or identity of at least 80%, more preferably at least 85%, even more preferably at least 90%, such as for instance at least 95% with Cpf1. In further embodiments, the homologue or orthologue of Cpf1 as referred to herein has a sequence identity of at least 80%, more preferably at least 85%, even more preferably at least 90%, such as for instance at least 95% with the wild type Cpf1. Where the Cpf1 has one or more mutations (mutated), the homologue or orthologue of said Cpf1 as referred to herein has a sequence identity of at least 80%, more preferably at least 85%, even more preferably at least 90%, such as for instance at least 95% with the mutated Cpf1.

In an embodiment, the Cpf1 protein may be an ortholog of an organism of a genus which includes, but is not limited to, *Acidaminococcus* sp., Lachnospiraceae bacterium or *Moraxella bovoculi*; in particular embodiments, the type V Cas protein may be an ortholog of an organism of a species which includes, but is not limited to *Acidaminococcus* sp. BV3L6; Lachnospiraceae bacterium ND2006 (LbCpf1) or *Moraxella bovoculi* 237. In particular embodiments, the homologue or orthologue of Cpf1 as referred to herein has a sequence homology or identity of at least 80%, more preferably at least 85%, even more preferably at least 90%, such as for instance at least 95% with one or more of the Cpf1 sequences disclosed herein. In further embodiments, the homologue or orthologue of Cpf as referred to herein has a sequence identity of at least 80%, more preferably at least 85%, even more preferably at least 90%, such as for instance at least 95% with the wild type FnCpf1, AsCpf1 or LbCpf1.

In particular embodiments, the Cpf1 protein of the invention has a sequence homology or identity of at least 60%, more particularly at least 70, such as at least 80%, more preferably at least 85%, even more preferably at least 90%, such as for instance at least 95% with FnCpf1, AsCpf1 or LbCpf1. In further embodiments, the Cpf1 protein as referred to herein has a sequence identity of at least 60%, such as at least 70%, more particularly at least 80%, more preferably at least 85%, even more preferably at least 90%, such as for instance at least 95% with the wild type AsCpf1 or LbCpf1. In particular embodiments, the Cpf1 protein of the present invention has less than 60% sequence identity with FnCpf1. The skilled person will understand that this includes truncated forms of the Cpf1 protein whereby the sequence identity is determined over the length of the truncated form.

Cas12b Orthologs

The present invention encompasses the use of a Cas12b (C2c1) effector proteins, derived from a C2c1 locus denoted as subtype V-B. Herein such effector proteins are also referred to as "C2c1p", e.g., a C2c1 protein (and such effector protein or C2c1 protein or protein derived from a C2c1 locus is also called "CRISPR enzyme"). Presently, the subtype V-B loci encompass cas1-Cas4 fusion, cas2, a distinct gene denoted C2c1 and a CRISPR array. C2c1 (CRISPR-associated protein C2c1) is a large protein (about 1100-1300 amino acids) that contains a RuvC-like nuclease domain homologous to the corresponding domain of Cas9 along with a counterpart to the characteristic arginine-rich cluster of Cas9. However, C2c1 lacks the HNH nuclease domain that is present in all Cas9 proteins, and the RuvC-like domain is contiguous in the C2c1 sequence, in contrast to Cas9 where it contains long inserts including the HNH domain. Accordingly, in particular embodiments, the CRISPR-Cas enzyme comprises only a RuvC-like nuclease domain.

C2c1 (also known as Cas12b) proteins are RNA guided nucleases. Its cleavage relies on a tracr RNA to recruit a guide RNA comprising a guide sequence and a direct repeat, where the guide sequence hybridizes with the target nucleotide sequence to form a DNA/RNA heteroduplex. Based on current studies, C2c1 nuclease activity also requires relies on recognition of PAM sequence. C2c1 PAM sequences are T-rich sequences. In some embodiments, the PAM sequence is 5' TTN 3' or 5' ATTN 3', wherein N is any nucleotide. In a particular embodiment, the PAM sequence is 5' TTC 3'. In a particular embodiment, the PAM is in the sequence of *Plasmodium falciparum*.

C2c1 creates a staggered cut at the target locus, with a 5' overhang, or a "sticky end" at the PAM distal side of the target sequence. In some embodiments, 5' overhang is 7 nt. See Lewis and Ke, Mol Cell. 2017 Feb. 2; 65 (3): 377-379.

The invention provides C2c1 (Type V-B; Cas12b) effector proteins and orthologues. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related or are only partially structurally related. An "orthologue" of a protein as used herein is a protein of a different species which performs the same or a similar function as the protein it is an orthologue of. Orthologous proteins may but need not be structurally related or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22 (4): 359-66. doi: 10.1002/pro.2225.). See also Shmakov et al. (2015) for application in the field of CRISPR-Cas loci. Homologous proteins may but need not be structurally related or are only partially structurally related.

The C2c1 gene is found in several diverse bacterial genomes, typically in the same locus with cas1, cas2, and cas4 genes and a CRISPR cassette. Thus, the layout of this putative novel CRISPR-Cas system appears to be similar to that of type II-B. Furthermore, similar to Cas9, the C2c1 protein contains an active RuvC-like nuclease, an arginine-rich region, and a Zn finger (absent in Cas9).

In particular embodiments, the effector protein is a C2c1 effector protein from an organism from a genus comprising *Alicyclobacillus, Desulfovibrio, Desulfonatronum, Opituta-ceae, Tuberibacillus, Bacillus, Brevibacillus, Candidatus, Desulfatirhabdium, Citrobacter, Elusimicrobia, Methylo-bacterium, Omnitrophica, Phycisphaerae, Planctomycetes, Spirochaetes*, and Verrucomicrobiaceae.

In further particular embodiments, the C2c1 effector protein is from a species selected from *Alicyclobacillus acido-terrestris* (e.g., ATCC 49025), *Alicyclobacillus contaminans* (e.g., DSM 17975), *Alicyclobacillus macrosporangiidus* (e.g., DSM 17980), *Bacillus hisashii* strain C4, *Candidatus* Lindowbacteria bacterium RIFCSPLOWO2, *Desulfovibrio inopinatus* (e.g., DSM 10711), *Desulfonatronum thiodis-mutans* (e.g., strain MLF-1), Elusimicrobia bacterium RIFOXYA12, Omnitrophica WOR 2 bacterium RIFCSPHIGHO2, Opituteaceae bacterium TAV5, Phycispha-erae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Cit-robacter freundii* (e.g., ATCC 8090), *Brevibacillus agri* (e.g., BAB-2500), *Methylobacterium nodulans* (e.g., ORS 2060).

The effector protein may comprise a chimeric effector protein comprising a first fragment from a first effector protein (e.g., a C2c1) ortholog and a second fragment from a second effector (e.g., a C2c1) protein ortholog, and wherein the first and second effector protein orthologs are different. At least one of the first and second effector protein (e.g., a C2c1) orthologs may comprise an effector protein (e.g., a C2c1) from an organism comprising *Alicyclobacillus, Desulfovibrio, Desulfonatronum, Opitutaceae, Tuberibacillus, Bacillus, Brevibacillus, Candidatus, Desulfatirhabdium, Elusimicrobia, Citrobacter, Methylobacterium, Omnitrophicai, Phycisphaerae, Planctomycetes, Spirochaetes*, and Verrucomicrobiaceae; e.g., a chimeric effector protein comprising a first fragment and a second fragment wherein each of the first and second fragments is selected from a C2c1 of an organism comprising *Alicyclobacillus, Desulfovibrio, Desulfonatronum, Opitutaceae, Tuberibacillus, Bacillus, Brevibacillus, Candidatus, Desulfatirhabdium, Elusimicrobia, Citrobacter, Methylobacterium, Omnitrophicai, Phycisphaerae, Planctomycetes, Spirochaetes*, and Verrucomicrobiaceae wherein the first and second fragments are not from the same bacteria; for instance a chimeric effector protein comprising a first fragment and a second fragment wherein each of the first and second fragments is selected from a C2c1 of *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus* Lindowbacteria bacterium RIFCSPLOWO2, *Desulfovibrio inopinatus* (e.g., DSM 10711), *Desulfonatronum thiodismutans* (e.g., strain MLF-1), Elusimicrobia bacterium RIFOXYA12, Omnitrophica WOR 2 bacterium RIFCSPHIGHO2, Opitutaceae bacterium TAV5, Phycisphaerae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060), wherein the first and second fragments are not from the same bacteria.

In a more preferred embodiment, the C2c1p is derived from a bacterial species selected from *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus* Lindowbacteria bacterium RIFCSPLOWO2, *Desulfovibrio inopinatus* (e.g., DSM 10711), Desulfonatronuim thiodismutans (e.g., strain MLF-1), Elusimicrobia bacterium RIFOXYA12, Omnitrophica WOR 2 bacterium RIFCSPHIGHO2, Opitutaceae bacterium TAV5, Phycisphaerae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060). In certain embodiments, the C2c1p is derived from a bacterial species selected from *Alicyclobacillus acidoterrestris* (e.g., ATCC 49025), *Alicyclobacillus contaminans* (e.g., DSM 17975).

In particular embodiments, the homologue or orthologue of C2c1 as referred to herein has a sequence homology or identity of at least 80%, more preferably at least 85%, even more preferably at least 90%, such as for instance at least 95% with C2c1. In further embodiments, the homologue or orthologue of C2c1 as referred to herein has a sequence identity of at least 80%, more preferably at least 85%, even more preferably at least 90%, such as for instance at least 95% with the wild type C2c1. Where the C2c1 has one or more mutations (mutated), the homologue or orthologue of said C2c1 as referred to herein has a sequence identity of at least 80%, more preferably at least 85%, even more preferably at least 90%, such as for instance at least 95% with the mutated C2c1.

In an embodiment, the C2c1 protein may be an ortholog of an organism of a genus which includes, but is not limited to *Alicyclobacillus, Desulfovibrio, Desulfonatromim, Opitutaceae, Tuberibacillus, Bacillus, Brevibacillus, Candidatus, Desulfatirhabdium, Elusimicrobia, Citrobacter, Methylobacterium, Omnitrophicai, Phycisphaerae, Planctomycetes, Spirochaetes*, and Verrucomicrobiaceae; in particular embodiments, the type V Cas protein may be an ortholog of an organism of a species which includes, but is not limited to *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus* Lindowbacteria bacterium RIFCSPLOWO2, *Desulfovibrio inopinatus* (e.g., DSM 10711), *Desulfonatronum thiodismutans* (e.g., strain MLF-1), Elusimicrobia bacterium RIFOXYA12, Omnitrophica WOR 2 bacterium RIFCSPHIGHO2, Opitutaceae bacterium TAV5, Phycisphaerae bacterium ST-NAGAB-D1, Planctomycetes bacterium RBG_13_46_10, Spirochaetes bacterium GWB1_27_13, Verrucomicrobiaceae bacterium UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060). In particular embodiments, the homologue or orthologue of C2c1 as referred to herein has a sequence homology or identity of at least 80%, more preferably at least 85%, even more preferably at least 90%, such as for instance at least 95% with one or more of the C2c1 sequences disclosed herein. In further embodiments, the homologue or orthologue of C2c1 as referred to herein has a sequence identity of at least 80%, more preferably at least 85%, even more preferably at least 90%, such as for instance at least 95% with the wild type AacC2c1 or BthC2c1.

In particular embodiments, the C2c1 protein of the invention has a sequence homology or identity of at least 60%, more particularly at least 70, such as at least 80%, more preferably at least 85%, even more preferably at least 90%, such as for instance at least 95% with AacC2c1 or BthC2c1. In further embodiments, the C2c1 protein as referred to herein has a sequence identity of at least 60%, such as at least 70%, more particularly at least 80%, more preferably at least 85%, even more preferably at least 90%, such as for instance at least 95% with the wild type AacC2c1. In particular embodiments, the C2c1 protein of the present invention has less than 60% sequence identity with AacC2c1. The skilled person will understand that this includes truncated forms of the C2c1 protein whereby the sequence identity is determined over the length of the truncated form.

The programmability, specificity, and collateral activity of the RNA-guided C2c1 also make it an ideal switchable nuclease for non-specific cleavage of nucleic acids. In one embodiment, a C2c1 system is engineered to provide and take advantage of collateral non-specific cleavage of RNA. In another embodiment, a C2c1 system is engineered to provide and take advantage of collateral non-specific cleavage of ssDNA. Accordingly, engineered C2c1 systems provide platforms for nucleic acid detection and transcriptome manipulation, and inducing cell death. C2c1 is developed for use as a mammalian transcript knockdown and binding tool. C2c1 is capable of robust collateral cleavage of RNA and ssDNA when activated by sequence-specific targeted DNA binding.

In an embodiment, the C2c1 system is engineered to non-specifically cleave RNA in a subset of cells distinguishable by the presence of an aberrant DNA sequence, for instance where cleavage of the aberrant DNA might be incomplete or ineffectual. In one non-limiting example, a DNA translocation that is present in a cancer cell and drives cell transformation is targeted. Whereas a subpopulation of cells that undergoes chromosomal DNA and repair may survive, non-specific collateral ribonuclease activity advantageously leads to cell death of potential survivors.

Collateral activity was recently leveraged for a highly sensitive and specific nucleic acid detection platform termed SHERLOCK that is useful for many clinical diagnoses (Gootenberg, J. S. et al. Nucleic acid detection with CRISPR-Cas13a/C2c2. *Science* 356, 438-442 (2017)).

According to the invention, engineered C2c1 systems are optimized for DNA or RNA endonuclease activity and can be expressed in mammalian cells and targeted to effectively knock down reporter molecules or transcripts in cells.

In certain example embodiments, the signal amplification CRISPR effector protein is a Type III-A CRISPR-Cas system effector protein. In certain example embodiments, the Type III-A CRISPR-Cas effector protein is Csm6. Csm6 functions with the multiprotein Csm effector complex, but is not part of the complex (see, e.g., US20170198286 A1; WO2016035044A1; M. Kazlauskiene et al., Science 10.1126/science.aao0100 (2017); and Niewoehner et al. 2017, bioRxiv preprint first posted online Jun. 23, 2017; doi: dx.doi.org/10.1101/153262).

In *Staphylococcus epidermidis* the Csm complex (SeCsm) is comprised of Cas10, Csm2, Csm3, Csm4, and Csm5 proteins. The Type III-A CRISPR-Cas system was demonstrated to have RNA cleavage activity both in vitro and in the cell using the Csm complex for *Streptococcus thermophilus* (St) (see, e.g., US20170198286 A1).

Type III-A CRISPR-Cas systems include *Streptococcus thermophilus* (GenBank KM222358), DGCC7710 (GenBank AWVZ01000003), LMD-9 (GenBank NC008532), *Staphylococcus epidermidis* RP62a (GenBank NC002976), *Enterococcus italicus* DSM15952 (GenBank AEPV01000074), *Lactococcus lactis* DGCC7167 (GenBank JX524189) and *Sulfolobus solfataricus* P2 (GenBank AE006641). The Type III-A system of DGCC8004 contains 10 cas genes flanking the CRISPR2 array and includes cast, cas2, cas6, cas10, csm2, csm3, csm4, csm5, csm6 and csm6' genes. The DGCC8004 CRISPR2 locus shares a similar gene arrangement to that of DGCC7710 (GenBank AWVZ00000000, (Horvath and Barrangou, 2010)) and LMD-9 (GenBank NC_008532, (Makarova et al., 2006)). The major difference is an additional csm6' gene in DGCC8004. The Csm6' protein in DGCC8004 is comprised of 386 aa and shows-34% amino acid identity to the 428 aa Csm6 protein, suggesting a possible ancient gene duplication event followed by sequence divergence. In contrast, DGCC7710 contains only a short 117-nt ORF in front of csm6. The Cas/Csm proteins associated to CRISPR2 in DGCC8004 are homologous to the corresponding proteins in DGCC7710 and LMD-9 (more than 90% aa identity, except for the Csm2 protein, which shares ~70% identity). Other experimentally characterized Type III-A systems including *S. epidermidis* RP62a (GenBank NC002976, (Marraffini and Sontheimer, 2008)), *Enterococcus italicus* DSM15952 (GenBank AEPV01000074, (Millen et al., 2012)) and *Lactococcus lactis* DGCC7167 (GenBank JX524189, (Millen et al., 2012)) share with DGCC8004 a conserved arrangement of the cas10-csm2-csm3-csm4-csm5-csm6 gene cluster, while the position of cas6 and cast/cas2 genes differ in some strains. The Type III-A CRISPR-Cas locus in *S. solfataricus* P2 (GenBank AE006641) has different gene organization and shows low protein sequence similarity to Cas/Csm orthologues in DGCC8004. Noteworthy, the Csm3 protein is most conserved among the Cas/Csm proteins across different strains and 5 copies of the Csm3 paralogues are present in *S. solfataricus*. Repeat sequences in *S. epidermidis, E. italicus* and *L. lactis* are of the same length (36 nt), however the nucleotide conservation is limited to the palindromic parts and 3'-terminal end of the repeats. The 8-nt 3'-terminal sequence of the repeat, which may contribute to the crRNA 5'-handle, shows an ACGRRAAC consensus between *S. thermophilus, S. epidermidis, E. italicus* and *L. lactis* but differs from that of *S. solfataricus* (AUUGAAG (Rouillon et al., 2013)).

Csm6 has been shown to be a ssRNA-specific endoribonuclease and the structural basis for this activity was determined (Niewoehner and Jinek, 2016, Structural basis for the endoribonuclease activity of the type III-A CRISPR-associated protein Csm6. RNA 22:318-329).

In some embodiments, one or more elements of a nucleic acid-targeting system of the present invention is derived from a particular organism comprising an endogenous CRISPR RNA-targeting system. In certain embodiments, the CRISPR RNA-targeting system comprises a Csm6 protein, Csm6 orthologue, or Csm6-like protein. As used herein, discussion of Csm6 also refers to Csm6 proteins, Csm6 orthologues, or Csm6-like proteins. Csm6 orthologues may be found in organisms as described herein and known in the art (see, e.g., WO2016035044A1 and Niewoehner and Jinek, 2016). Exemplary Csm6 orthologues include, but are not limited to *T. thermophilus* (TtCsm6, GI: 55978335), *S. epidermidis* (SeCsm6, GI: 488416649), *S. mutans* (SmCsm6, GI: 24379650), *S. thermophiles* (StCsm6, GI: 585230687), and *P. furiosus* Csx1 (PfCsx1, GI: 33359545). In certain embodiments, Csm6 proteins useful for the present invention comprise at least one N-terminal CARF (CRISPR-associated Rossman fold) domain and at least one C-terminal HEPN domain (higher eukaryotes and prokaryotes nucleotide-binding domain). In certain embodiments, Csm6 proteins form dimers. In certain embodiments, dimerization of the HEPN domains leads to the formation of a ribonuclease active site. In certain embodiments, the dimer interface of the CARF domains comprise an electropositive pocket. Not being bound by a theory, the pocket may function as a ligand-binding site for allosteric control of ribonuclease activity.

In certain example embodiments, the CRISPR-based detection systems described herein comprise a Csm6 protein comprising at least one HEPN domain, including but not limited to the HEPN domains described herein, HEPN domains known in the art (Niewoehner and Jinek, 2016), and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the Csm6 protein comprises a single HEPN domain. In certain other example embodiments, the Csm6 protein comprises two HEPN domains.

In one example embodiment, the Csm6 protein comprises one or more HEPN domains comprising an RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed herein. In certain embodiments, the HEPN domain comprises a conserved R-X4-6-H motif (Anantharaman et al., Biol Direct. 2013 Jun. 15; 8:15; and Kim et al., Proteins. 2013 February; 81 (2): 261-70).

In an embodiment of the invention, a HEPN domain comprises at least one RxxxxH motif comprising the sequence of R{N/H/K}X1X2X3H. In an embodiment of the invention, a HEPN domain comprises a RxxxxH motif comprising the sequence of R{N/H}X1X2X3H. In an embodiment of the invention, a HEPN domain comprises the sequence of R{N/K}X1X2X3H. In certain embodiments, X1 is R, S, D, E, Q, N, G, Y, or H. In certain embodiments, X2 is I, S, T, V, or L. In certain embodiments, X3 is L, F, N, Y, V, I, S, D, E, or A.

CARF domains and consensus sequences for CARF domains have been described (see, e.g., Makarova et al., Front Genet. 2014; 5:102). In certain embodiments, Csm6 comprises at least one CARF domain comprising a core domain comprising a six-stranded Rossmann-like fold with the core strand-5 and strand-6 forming a β-hairpin. The main regions of sequence conservation are associated with strand-1 and strand-4 of the core domain. In certain embodiments, the end of strand-1 is characterized by a polar residue, typically with an alcoholic side chain (S/T). In certain embodiments, immediately downstream of strand-4 is a highly conserved basic residue (K/R), preferably associated with a [DN]X[ST]XXX[RK] signature (SEQ ID NO: 36). In certain embodiments, Csm6 is truncated to remove the N-terminal CARF domain (e.g., amino acids 1-190 of TtCsm6 or the equivalent residues in orthologous Csm6 proteins).

In certain embodiments, Csm6 comprises at least one 6H domain (Niewoehner and Jinek, 2016). The 6H domain of TtCsm6 polypeptide chain (residues 191-292) consists of five α-helices and forms a right-handed solenoid domain. Not being bound by a theory, since some orthologues may not have a 6H domain, this domain is not required for activity of the Csm6 protein of the present invention.

Csm6 has been shown to contribute to interference by functioning as a standalone ribonuclease that degrades invader RNA transcripts. Csm6 proteins are activated through a second messenger generated by the type III interference complex. Upon target RNA binding by the type III interference complex, the Cas10 subunit converts ATP into a cyclic oligoadenylate product, which allosterically activates Csm6 by binding to its CARF domain. CARF domain mutations that abolish allosteric activation inhibit Csm6 activity in vivo, and mutations in the Cas10 Palm domain phenocopy loss of Csm6 (M. Kazlauskiene et al., 2017; and Niewoehner et al. 2017).

In certain example embodiments, the signal amplification CRISPR effector protein is activated when the activated CRISPR detection protein cleaves an activation sequence. The activation sequences are described in further detail below. The cleavage product of the activation sequence activates a separate activity of the signal amplification CRISPR effector protein, such as an RNA nuclease activity. For example, Csm6, once activated, cleaves RNA indiscriminately similar to the collateral effect of Cas13 enzymes.

Thus, in addition to detection effector modification of reporter constructs, the activated signal amplification CRISPR effector protein also modifies reporter constructs to further enhance signal generation. In certain embodiments, Csm6 is activated when provided in conjunction with another CRISPR enzyme (e.g., Cas13). In certain embodiments, Csm6 can generate a synergistic effect when used in conjunction with Cas13, such that Cas13 collateral activity is greatly increased. Not being bound by a theory, the concentration of Cas13 can be greatly decreased in an assay when Csm6 is also included in the assay (e.g., point of care assay). Thus, Csm6 addition to a Cas13 diagnostic assay can be used to increase sensitivity of the assay and decrease cost.

CRISPR effectors often interact with additional components to modulate activity, and Type VI-B CRISPR systems often harbor the interference-modulating proteins Csx27 and Csx28, and Csx28 co-expression has been demonstrated to increase the interference activity of Cas13b proteins in vivo. In certain embodiments, the one or more signal amplification CRISPR effector proteins comprise Csx28 or Csx27.

Guide RNAs

As used herein, the term "guide sequence," "crRNA," "guide RNA," or "single guide RNA," or "gRNA" refers to a polynucleotide comprising any polynucleotide sequence having sufficient complementarity with a target nucleic acid sequence to hybridize with the target nucleic acid sequence and to direct sequence-specific binding of a RNA-targeting complex comprising the guide sequence and a CRISPR effector protein to the target nucleic acid sequence. In some example embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAST, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and PA Carr and GM Church, 2009, Nature Biotechnology 27 (12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

In general, the CRISPR-Cas, CRISPR-Cas9 or CRISPR system may be as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAST, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

Guide Modifications

In certain embodiments, guides of the invention comprise non-naturally occurring nucleic acids and/or non-naturally occurring nucleotides and/or nucleotide analogs, and/or chemically modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified bases include, but are not limited to, 2-aminopurine, 5-bromo-uridine, pseudouridine ($\Psi$), N1-methylpseudouridine (me1$\Psi$), 5-methoxyuridine (5moU), inosine, 7-methylguanosine. Examples of guide RNA chemical modifications include, without limitation, incorporation of 2'-O-methyl (M), 2'-O-methyl-3'-phosphorothioate (MS), phosphorothioate (PS), S-constrained ethyl (cEt), or 2'-O-methyl-3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33 (9): 985-9, doi: 10.1038/nbt.3290, published online 29 Jun. 2015; Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33 (9): 985-989; Li et al., Nature Biomedical Engineering, 2017, 1, 0066 DOI: 10.1038/s41551-017-0066). In some embodiments, 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target DNA and one or more deoxyribonucleotides and/or nucleotide analogs in a region that binds to Cas9, Cpf1, or C2c1. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in 5'-handle of the stem-loop regions. Chemical modification in 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either 3' or 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at 5' and/or 3' end of the guide are chemically modified with 2'-O-methyl (M), 2'-O-methyl-3'-phosphorothioate (MS), S-constrained ethyl (cEt), or 2'-O-methyl-3'-thioPACE (MSP). Such modification can enhance genome editing efficiency (see Hendel et al., Nat. Biotechnol. (2015) 33 (9): 985-989). In certain embodiments, all of the phosphodiester bonds of a guide are substituted with phosphorothioates (PS) for enhancing levels of gene disruption. In certain embodiments, more than five nucleotides at 5' and/or 3' end of the guide are chemically modified with 2'-O-Me, 2'-F or S-constrained ethyl (cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6: e25312, DOI: 10.7554).

In certain embodiments, the CRISPR system as provided herein can make use of a crRNA or analogous polynucleotide comprising a guide sequence, wherein the polynucleotide is an RNA, a DNA or a mixture of RNA and DNA, and/or wherein the polynucleotide comprises one or more nucleotide analogs. The sequence can comprise any structure, including but not limited to a structure of a native crRNA, such as a bulge, a hairpin or a stem loop structure. In certain embodiments, the polynucleotide comprising the guide sequence forms a duplex with a second polynucleotide sequence which can be an RNA or a DNA sequence.

In certain embodiments, use is made of chemically modified guide RNAs. Examples of guide RNA chemical modifications include, without limitation, incorporation of 2'-O-methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33 (9): 985-9, doi: 10.1038/nbt.3290, published online 29 Jun. 2015). Chemically modified guide RNAs further include, without limitation, RNAs with phosphorothioate linkages and locked nucleic acid (LNA) nucleotides comprising a methylene bridge between the 2' and 4' carbons of the ribose ring.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 to 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target RNA may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methyl-guanosine, 2'-O-methyl-3'-phosphorothioate (MS), S-constrained ethyl (cEt), phosphorothioate (PS), or 2'-O-methyl- 3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in 3'-terminus are chemically modified. In certain embodiments, none of the nucleotides in 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in 3'-terminus are chemically modified. Such chemical modifications at the 3'-terminus of the Cpf1 CrRNA improve gene cutting efficiency (see Li, et al., Nature Biomedical Engineering, 2017, 1:0066). In a specific embodiment, 5 nucleotides in 3'-terminus are replaced with 2'-fluoro analogues. In a specific embodiment, 10 nucleotides in the 3'-terminus are replaced with 2'-fluoro analogues. In a specific embodiment, 5 nucleotides in 3'-terminus are replaced with 2'-O-methyl (M) analogs.

In some embodiments, the loop of 5'-handle of the guide is modified. In some embodiments, the loop of 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU.

A guide sequence, and hence a nucleic acid-targeting guide RNA may be selected to target any target nucleic acid sequence. In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nuclear RNA (snoRNA), double stranded RNA (dsRNA), non-coding RNA (ncRNA), long non-coding RNA (lncRNA), and small cytoplasmic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In certain embodiments, the spacer length of the guide RNA is less than 28 nucleotides. In certain embodiments, the spacer length of the guide RNA is at least 18 nucleotides and less than 28 nucleotides. In certain embodiments, the spacer length of the guide RNA is between 19 and 28 nucleotides. In certain embodiments, the spacer length of the guide RNA is between 19 and 25 nucleotides. In certain embodiments, the spacer length of the guide RNA is 20 nucleotides. In certain embodiments, the spacer length of the guide RNA is 23 nucleotides. In certain embodiments, the spacer length of the guide RNA is 25 nucleotides.

In certain embodiments, modulations of cleavage efficiency can be exploited by introduction of mismatches, e.g. 1 or more mismatches, such as 1 or 2 mismatches between spacer sequence and target sequence, including the position of the mismatch along the spacer/target. The more central (i.e. not 3' or 5') for instance a double mismatch is, the more cleavage efficiency is affected. Accordingly, by choosing mismatch position along the spacer, cleavage efficiency can be modulated. By means of example, if less than 100% cleavage of targets is desired (e.g. in a cell population), 1 or more, such as preferably 2 mismatches between spacer and target sequence may be introduced in the spacer sequences. The more central along the spacer of the mismatch position, the lower the cleavage percentage.

In certain example embodiments, the cleavage efficiency may be exploited to design single guides that can distinguish two or more targets that vary by a single nucleotide, such as a single nucleotide polymorphism (SNP), variation, or (point) mutation. The CRISPR effector may have reduced sensitivity to SNPs (or other single nucleotide variations) and continue to cleave SNP targets with a certain level of efficiency. Thus, for two targets, or a set of targets, a guide RNA may be designed with a nucleotide sequence that is complementary to one of the targets i.e. the on-target SNP. The guide RNA is further designed to have a synthetic mismatch. As used herein a "synthetic mismatch" refers to a non-naturally occurring mismatch that is introduced upstream or downstream of the naturally occurring SNP, such as at most 5 nucleotides upstream or downstream, for instance 4, 3, 2, or 1 nucleotide upstream or downstream, preferably at most 3 nucleotides upstream or downstream, more preferably at most 2 nucleotides upstream or downstream, most preferably 1 nucleotide upstream or downstream (i.e. adjacent the SNP). When the CRISPR effector binds to the on-target SNP, only a single mismatch will be formed with the synthetic mismatch and the CRISPR effector will continue to be activated, and a detectable signal produced. When the guide RNA hybridizes to an off-target SNP, two mismatches will be formed, the mismatch from the SNP and the synthetic mismatch, and no detectable signal generated. Thus, the systems disclosed herein may be designed to distinguish SNPs within a population. For, example the systems may be used to distinguish pathogenic strains that differ by a single SNP or detect certain disease specific SNPs, such as but not limited to, disease associated SNPs, such as without limitation cancer associated SNPs.

In certain embodiments, the guide RNA is designed such that the SNP is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the SNP is located on position 1, 2, 3, 4, 5, 6, 7, 8, or 9 of the spacer sequence (starting at the 5' end). In certain embodiments, the guide RNA is designed such that the SNP is located on position 2, 3, 4, 5, 6, or 7 of the spacer sequence (starting at the 5' end). In certain embodiments, the guide RNA is designed such that the SNP is located on position 3, 4, 5, or 6 of the spacer sequence (starting at the 5' end). In certain embodiments, the guide RNA is designed such that the SNP is located on position 3 of the spacer sequence (starting at the 5' end).

In certain embodiments, the guide RNA is designed such that the mismatch (e.g., the synthetic mismatch, i.e., an additional mutation besides a SNP) is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the mismatch is located on position 1, 2, 3, 4, 5, 6, 7, 8, or 9 of the spacer sequence (starting at the 5' end). In certain embodiments, the guide RNA is designed such that the mismatch is located on position 4, 5, 6, or 7 of the spacer sequence (starting at the 5' end. In certain embodiments, the guide RNA is designed such that the mismatch is located on position 5 of the spacer sequence (starting at the 5' end).

In certain embodiments, the guide RNA is designed such that the mismatch is located 2 nucleotides upstream of the SNP (i.e. one intervening nucleotide).

In certain embodiments, the guide RNA is designed such that the mismatch is located 2 nucleotides downstream of the SNP (i.e. one intervening nucleotide).

In certain embodiments, the guide RNA is designed such that the mismatch is located on position 5 of the spacer sequence (starting at the 5' end) and the SNP is located on position 3 of the spacer sequence (starting at the 5' end).

The embodiments described herein comprehend inducing one or more nucleotide modifications in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s). The mutations can include the introduction, deletion, or substitution of 1-75 nucleotides at each target sequence of said cell(s) via the guide(s) RNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 40, 45, 50, 75, 100, 200, 300, 400 or 500 nucleotides at each target sequence of said cell(s) via the guide(s) RNA(s).

Typically, in the context of an endogenous CRISPR system, formation of a CRISPR complex (comprising a guide sequence hybridized to a target sequence and complexed with one or more Cas proteins) results in cleavage in or near (e.g. within 1, 2, 3, 4, 5, 6, 7, 8, 9, 10, 20, 50, or more base pairs from) the target sequence, but may depend on for instance secondary structure, in particular in the case of RNA targets.

In some embodiments, the one or more guide RNAs are designed to bind to one or more target molecules that are diagnostic for a disease state. In still further embodiments, the disease state is an infection, an organ disease, a blood disease, an immune system disease, a cancer, a brain and nervous system disease, an endocrine disease, a pregnancy or childbirth-related disease, an inherited disease, or an environmentally-acquired disease. In still further embodiments, the disease state is cancer or an autoimmune disease or an infection.

In specific embodiments, the target molecule or target sequence is diagnostic for a tick-borne disease state. A tick-borne disease state comprises detection of a tick-borne disease, detection of a phenotype of a disease-causing agent, for example, antibiotic resistance or susceptibility, and/or a combination thereof.

In some embodiments, the tick-borne disease may include, but is not necessarily limited to; anaplasmosis caused by the bacterium *Anaplasma phagocytophilum* or other *Anaplasma* species; babesiosis caused by the parasite *Babesia microti* or other *Babesia* species; *Borrelia* infections caused by *Borrelia mayonii, Borrelia miyamotoi, Borrelia burgdorferi* (Lyme disease), or other *Borrelia* species; infections caused by Bourbon virus; Colorado tick fever caused by Coltivirus; Ehrlichiosis caused by the bacterium *Ehrlichia chaffeensis*; Heartland virus infection; Powassan disease caused by Powassan virus; *Rickettsia parkeri* rickettsiosis caused by *Rickettsia parkeri*; Rocky Mountain spotted fever caused by the bacterium *Rickettsia rickettsii*; Southern tick-associated rash illness; tick-borne relapsing fever caused by bacterial *Borrelia hermsii, Borrelia parkeri, Borrelia turicatae*, or *Borrelia hermsii* species; Tularemia caused by the bacterium *Francisella tularensis*; and 364D rickettsiosis caused by *Rickettsia* species.

In specific embodiments, the guide RNAs may be designed to bind to the cytB region of *Babesia microti*, the glycerophosphodiester phosphodiesterase gene (glpQ) gene of *Babesia microti*, the flagellin B gene (flab) of *Babesia microti*, the 16s region of 16S IRNA gene of *A. phagocytophilum*, and/or the cytB gene of *B. miyamotoi*, as described in the examples. In some embodiments, the guide RNA is designed to bind to the *B. microti* atovaquone-binding region of cytB.

In specific embodiments, the guide RNAs comprise 20, 21, 22, 23, 24, 25, 26, 27 or 28 continuous nucleotides of a sequence selected from SEQ ID NOs: 6-29. In certain embodiments, the guide RNA comprises at least 95% sequence identity of 28 continuous nucleotides of a sequence selected from SEQ ID Nos: 6-29. In an aspect, the guide RNAs are selected from the guide RNAs depicted in any of FIGS. 6A-6C.

In specific embodiments, the guide RNAs are designed to detect variants of *Babesia microti*. For example, a set of guide RNAs is designed that can identify, for example, all microbial species within a defined set of microbes. In certain example embodiments, the methods for generating guide RNAs as described herein may be compared to methods disclosed in WO 2017/040316, incorporated herein by reference. As described in WO 2017040316, a set cover solution may identify the minimal number of target sequences probes or guide RNAs needed to cover an entire target sequence or set of target sequences, e.g. a set of genomic sequences. Set cover approaches have been used previously to identify primers and/or microarray probes, typically in the 20 to 50 base pair range. See, e.g. Pearson et al., cs.virginia.edu/~robins/papers/primers_dam11_final.pdf., Jabado et al. Nucleic Acids Res. 2006 34 (22): 6605-11, Jabado et al. Nucleic Acids Res. 2008, 36 (1): e3 doi 10.1093/nar/gkm 1106, Duitama et al. Nucleic Acids Res. 2009, 37 (8): 2483-2492, Phillippy et al. BMC Bioinformatics. 2009, 10:293 doi: 10.1186/1471-2105-10-293. However, such approaches generally involved treating each primer/probe as k-mers and searching for exact matches or allowing for inexact matches using suffix arrays. In addition, the methods generally take a binary approach to detecting hybridization by selecting primers or probes such that each input sequence only needs to be bound by one primer or probe and the position of this binding along the sequence is irrelevant. Alternative methods may divide a target genome into pre-defined windows and effectively treat each window as a separate input sequence under the binary approach—i.e. they determine whether a given probe or guide RNA binds within each window and require that all of the windows be bound by the state of some probe or guide RNA. Effectively, these approaches treat each element of the "universe" in the set cover problem as being either an entire input sequence or a pre-defined window of an input sequence, and each element is considered "covered" if the start of a probe or guide RNA binds within the element. These approaches limit the fluidity to which different probe or guide RNA designs are allowed to cover a given target sequence.

In contrast, the embodiments disclosed herein are directed to detecting longer probe or guide RNA lengths, for example, in the range of 70 bp to 200 bp that are suitable for hybrid selection sequencing. In addition, the methods disclosed WO 2017/040316 herein may be applied to take a pan-target sequence approach capable of defining a probe or guide RNA sets that can identify and facilitate the detection sequencing of all species and/or strains sequences in a large and/or variable target sequence set. For example, the methods disclosed herein may be used to identify all variants of a given virus, or multiple different viruses in a single assay. Further, the method disclosed herein treat each element of the "universe" in the set cover problem as being a nucleotide of a target sequence, and each element is considered "covered" as long as a probe or guide RNA binds to some segment of a target genome that includes the element. These types of set cover methods may be used instead of the binary approach of previous methods, the methods disclosed in herein better model how a probe or guide RNA may hybridize to a target sequence. Rather than only asking if a given guide RNA sequence does or does not bind to a given window, such approaches may be used to detect a hybridization pattern—i.e. where a given probe or guide RNA binds to a target sequence or target sequences—and then determines from those hybridization patterns the minimum number of probes or guide RNAs needed to cover the set of target sequences to a degree sufficient to enable both enrichment from a sample and sequencing of any and all target sequences. These hybridization patterns may be determined by defining certain parameters that minimize a loss function, thereby enabling identification of minimal probe or guide RNA sets in a way that allows parameters to vary for each species, e.g. to reflect the diversity of each species, as well as in a computationally efficient manner that cannot be achieved using a straightforward application of a set cover solution, such as those previously applied in the probe or guide RNA design context.

The ability to detect multiple transcript abundances may allow for the generation of unique microbial signatures indicative of a particular phenotype. Various machine learning techniques may be used to derive the gene signatures. Accordingly, the guide RNAs of the CRISPR systems may be used to identify and/or quantitate relative levels of biomarkers defined by the gene signature in order to detect certain phenotypes. In certain example embodiments, the gene signature indicates susceptibility to an antibiotic, resistance to an antibiotic, or a combination thereof.

In one aspect of the invention, a method comprises detecting one or more pathogens. In this manner, differentiation between infection of a subject by individual microbes may be obtained. In some embodiments, such differentiation may enable detection or diagnosis by a clinician of specific diseases, for example, different variants of a disease. Preferably the pathogen sequence is a genome of the pathogen or a fragment thereof. The method further may comprise determining the evolution of the pathogen. Determining the evolution of the pathogen may comprise identification of pathogen mutations, e.g. nucleotide deletion, nucleotide insertion, nucleotide substitution. Amongst the latter, there are non-synonymous, synonymous, and noncoding substitutions. Mutations are more frequently non-synonymous during an outbreak. The method may further comprise determining the substitution rate between two pathogen sequences analyzed as described above. Whether the mutations are deleterious or even adaptive would require functional analysis, however, the rate of non-synonymous mutations suggests that continued progression of this epidemic could afford an opportunity for pathogen adaptation, underscoring the need for rapid containment. Thus, the method may further comprise assessing the risk of viral adaptation, wherein the number non-synonymous mutations is determined. (Gire, et al., Science 345, 1369, 2014).

In some embodiments, the invention provides a nucleic acid detection system comprising two or more CRISPR systems, each CRISPR system comprising an effector protein and a guide RNA designed to bind to a corresponding target molecule that is diagnostic for a tick-borne disease state.

RNA-Based Masking Constructs

As used herein, a "masking construct" refers to a molecule that can be cleaved or otherwise deactivated by an activated CRISPR system effector protein described herein. The term "masking construct" may also be referred to in the alternative as a "detection construct" or "reporter construct." In certain example embodiments, the masking construct is an RNA-based masking construct. The masking construct prevents the generation or detection of a positive detectable signal. A positive detectable signal may be any signal that can be detected using optical, fluorescent, chemiluminescent, electrochemical or other detection methods known in the art. The masking construct may prevent the generation of a detectable positive signal or mask the presence of a detectable positive signal until the masking construct is removed or otherwise silenced. The term "positive detectable signal" is used to differentiate from other detectable signals that may be detectable in the presence of the masking construct. For example, in certain embodiments a first signal may be detected when the masking agent is present (i.e. a negative detectable signal), which then converts to a second signal (e.g. the positive detectable signal) upon detection of the target molecules and cleavage or deactivation of the masking agent by the activated CRISPR effector protein.

In certain example embodiments, the masking construct may suppress generation of a gene product. The gene product may be encoded by a reporter construct that is added to the sample. The masking construct may be an interfering RNA involved in an RNA interference pathway, such as a shRHN or siRNA. The masking construct may also comprise microRNA (miRNA). While present, the masking construct suppresses expression of the gene product. The gene product may be a fluorescent protein or other RNA transcript or proteins that would otherwise be detectable by a labeled probe or antibody but for the presence of the masking construct. Upon activation of the effector protein the masking construct is cleaved or otherwise silenced allowing for expression and detection of the gene product as the positive detectable signal.

In certain example embodiments, the masking construct may sequester one or more reagents needed to generate a detectable positive signal such that release of the one or more reagents from the masking construct results in generation of the detectable positive signal. The one or more reagents may combine to produce a colorimetric signal, a chemiluminescent signal, a fluorescent signal, or any other detectable signal and may comprise any reagents known to be suitable for such a purpose. In certain example embodiments, the one or more reagents are sequestered by RNA aptamers that bind the one or more reagents. The one or more reagents are released when the effector protein is activated upon detection of a target molecule. In certain example embodiments, the one or more reagents is a protein, such as an enzyme, capable of facilitating generation of a detectable signal, such as a colorimetric, chemiluminescent, or fluorescent signal, that is inhibited or sequestered such that the protein cannot generate the detectable signal by the binding of one or more RNA aptamers to the protein. Upon activation of the effector proteins disclosed herein, the RNA aptamers are cleaved or degraded to the extent they no longer inhibit the protein's ability to generate the detectable signal. In certain example embodiments, the aptamer is a thrombin inhibitor aptamer. In certain example embodiments the thrombin inhibitor aptamer has a sequence of GGGAACAAAGCUGAAGUACUUACCC (SEQ ID NO: 32). When this aptamer is cleaved, thrombin will become active and will cleave a peptide colorimetric or fluorescent substrate. In certain example embodiments, the colorimetric substrate is para-nitroanilide (pNA) covalently linked to the peptide substrate for thrombin. Upon cleavage by thrombin, pNA is released and becomes yellow in color and easily visible to the eye. In certain example embodiments, the fluorescent substrate is 7-amino-4-methylcoumarin a blue fluorophore that can be detected using a fluorescence detector. Inhibitory aptamers may also be used for horseradish peroxidase (HRP), beta-galactosidase, or calf alkaline phosphatase (CAP) within the general principals laid out above.

In certain embodiments, RNAse activity is detected colorimetrically via cleavage of enzyme-inhibiting aptamers. One potential mode of converting RNAse activity into a colorimetric signal is to couple the cleavage of an RNA aptamer with the re-activation of an enzyme that is capable of producing a colorimetric output. In the absence of RNA cleavage, the intact aptamer will bind to the enzyme target and inhibit its activity. The advantage of this readout system is that the enzyme provides an additional amplification step: once liberated from an aptamer via collateral activity (e.g. Cas13a collateral activity), the colorimetric enzyme will continue to produce colorimetric product, leading to a multiplication of signal.

In certain embodiments, an existing aptamer that inhibits an enzyme with a colorimetric readout is used. Several aptamer/enzyme pairs with colorimetric readouts exist, such as thrombin, protein C, neutrophil elastase, and substilisin. These proteases have colorimetric substrates based upon pNA and are commercially available. In certain embodiments, a novel aptamer targeting a common colorimetric enzyme is used. Common and robust enzymes, such as beta-galactosidase, horseradish peroxidase, or calf intestinal alkaline phosphatase, could be targeted by engineered aptamers designed by selection strategies such as SELEX. Such strategies allow for quick selection of aptamers with nanomolar binding efficiencies and could be used for the development of additional enzyme/aptamer pairs for colorimetric readout.

In certain embodiments, RNAse activity is detected colorimetrically via cleavage of RNA-tethered inhibitors. Many common colorimetric enzymes have competitive, reversible inhibitors: for example, beta-galactosidase can be inhibited by galactose. Many of these inhibitors are weak, but their effect can be increased by increases in local concentration. By linking local concentration of inhibitors to RNAse activity, colorimetric enzyme and inhibitor pairs can be engineered into RNAse sensors. The colorimetric RNAse sensor based upon small-molecule inhibitors involves three components: the colorimetric enzyme, the inhibitor, and a bridging RNA that is covalently linked to both the inhibitor and enzyme, tethering the inhibitor to the enzyme. In the uncleaved configuration, the enzyme is inhibited by the increased local concentration of the small molecule; when the RNA is cleaved (e.g. by Cas13a collateral cleavage), the inhibitor will be release and the colorimetric enzyme will be activated.

In certain embodiments, RNAse activity is detected colorimetrically via formation and/or activation of G-quadruplexes. G quadraplexes in DNA can complex with heme (iron (III)-protoporphyrin IX) to form a DNAzyme with peroxidase activity. When supplied with a peroxidase substrate (e.g. ABTS: (2,2'-Azinobis [3-ethylbenzothiazoline-6-sulfonic acid]-diammonium salt)), the G-quadraplex-heme complex in the presence of hydrogen peroxide causes oxidation of the substrate, which then forms a green color in solution. An example G-quadraplex forming DNA sequence is: GGGTAGGGCGGGTTGGGA (SEQ ID NO: 33). By hybridizing an RNA sequence to this DNA aptamer, formation of the G-quadraplex structure will be limited. Upon RNAse collateral activation (e.g. C2c2-complex collateral activation), the RNA staple will be cleaved allowing the G quadraplex to form and heme to bind. This strategy is particularly appealing because color formation is enzymatic, meaning there is additional amplification beyond RNAse activation.

In certain example embodiments, the masking construct may be immobilized on a solid substrate in an individual discrete volume (defined further below) and sequesters a single reagent. For example, the reagent may be a bead comprising a dye. When sequestered by the immobilized reagent, the individual beads are too diffuse to generate a detectable signal, but upon release from the masking construct are able to generate a detectable signal, for example by aggregation or simple increase in solution concentration. In certain example embodiments, the immobilized masking agent is an RNA-based aptamer that can be cleaved by the activated effector protein upon detection of a target molecule.

In certain other example embodiments, the masking construct binds to an immobilized reagent in solution thereby blocking the ability of the reagent to bind to a separate labeled binding partner that is free in solution. Thus, upon application of a washing step to a sample, the labeled binding partner can be washed out of the sample in the absence of a target molecule. However, if the effector protein is activated, the masking construct is cleaved to a degree sufficient to interfere with the ability of the masking construct to bind the reagent thereby allowing the labeled binding partner to bind to the immobilized reagent. Thus, the labeled binding partner remains after the wash step indicating the presence of the target molecule in the sample. In certain aspects, the masking construct that binds the immobilized reagent is an RNA aptamer. The immobilized reagent may be a protein, and the labeled minding partner may be a labeled antibody. Alternatively, the immobilized reagent may be a streptavidin, and the labeled binding partner may be labeled biotin. The label on the binding partner used in the above embodiments may be any detectable label known in the art. In addition, other known binding partners may be used in accordance with the overall design described here.

In certain example embodiments, the masking construct may comprise a ribozyme. Ribozymes are RNA molecules having catalytic properties. As ribozymes, both naturally and engineered, comprise or consist of RNA, that may be targeted by the effector proteins disclosed herein. The ribozyme may be selected or engineered to catalyze a reaction that either generates a negative detectable signal or prevents generation of a positive control signal. Upon deactivation of the ribozyme by the activated effector protein molecule the reaction generating a negative controls signal or preventing generation of a positive detectable signal is removed, thereby allowing a positive detectable signal to be detected. In one example embodiment, the ribozyme may catalyze a colorimetric reaction causing a solution to appear as a first color. When the ribozyme is deactivated, the solution then turns to a second color, the second color being the detectable positive signal. An example of how ribozymes can be used to catalyze a colorimetric reaction are described in Zhao et al. "Signal amplification of glucosamine-6-phosphate based on ribozyme glmS," Biosens Bioelectron. 2014; 16:337-42, and provide an example of how such a system could be modified to work in the context of the embodiments disclosed herein. Alternatively, ribozymes, when present can generate cleavage products of, for example, RNA transcripts. Thus, detection of a positive detectable signal may comprise detection of non-cleaved RNA transcripts that are only generated in the absence of the ribozyme.

In one example embodiment, the masking construct comprises a detection agent that changes color depending on whether the detection agent is aggregated or dispersed in solution. For example, certain nanoparticles, such as colloidal gold, undergo a visible purple to red color shift as they move from aggregates to dispersed particles. Accordingly, in certain example embodiments, such detection agents may be held in aggregate by one or more bridge molecules. See e.g. FIG. 43. At least a portion of the bridge molecule comprises RNA. Upon activation of the effector proteins disclosed herein, the RNA portion of the bridge molecule is cleaved allowing the detection agent to disperse and resulting in the corresponding change in color. See e.g. FIG. 45. In certain example embodiments, the bridge molecule is an RNA molecule. In certain example embodiments, the detection agent is a colloidal metal. The colloidal metal material may include water-insoluble metal particles or metallic compounds dispersed in a liquid, a hydrosol, or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, derived from an appropriate metal compound, for example the $A13+$, $Ru3+$, $Zn2+$, $Fe3+$, $Ni2+$ and $Ca2+$ ions.

In certain other example embodiments, the masking construct may comprise an RNA oligonucleotide to which are attached a detectable label and a masking agent of that detectable label. An example of such a detectable label/masking agent pair is a fluorophore and a quencher of the fluorophore. Quenching of the fluorophore can occur as a result of the formation of a non-fluorescent complex between the fluorophore and another fluorophore or non-fluorescent molecule. This mechanism is known as ground-state complex formation, static quenching, or contact quenching. Accordingly, the RNA oligonucleotide may be designed so that the fluorophore and quencher are in sufficient proximity for contact quenching to occur. Fluorophores and their cognate quenchers are known in the art and can be selected for this purpose by one having ordinary skill in the art. The particular fluorophore/quencher pair is not critical in the context of this invention, only that selection of the fluorophore/quencher pairs ensures masking of the fluorophore. Upon activation of the effector proteins disclosed herein, the RNA oligonucleotide is cleaved thereby severing the proximity between the fluorophore and quencher needed to maintain the contact quenching effect. Accordingly, detection of the fluorophore may be used to determine the presence of a target molecule in a sample.

In certain other example embodiments, the masking construct may comprise one or more RNA oligonucleotides to which are attached one or more metal nanoparticles, such as gold nanoparticles. In some embodiments, the masking construct comprises a plurality of metal nanoparticles cross-linked by a plurality of RNA oligonucleotides forming a closed loop. In one embodiment, the masking construct comprises three gold nanoparticles crosslinked by three RNA oligonucleotides forming a closed loop. In some embodiments, the cleavage of the RNA oligonucleotides by the CRISPR effector protein leads to a detectable signal produced by the metal nanoparticles.

In certain other example embodiments, the masking construct may comprise one or more RNA oligonucleotides to which are attached one or more quantum dots. In some embodiments, the cleavage of the RNA oligonucleotides by the CRISPR effector protein leads to a detectable signal produced by the quantum dots.

In one example embodiment, the masking construct may comprise a quantum dot. The quantum dot may have multiple linker molecules attached to the surface. At least a portion of the linker molecule comprises RNA. The linker molecule is attached to the quantum dot at one end and to one or more quenchers along the length or at terminal ends of the linker such that the quenchers are maintained in sufficient proximity for quenching of the quantum dot to occur. The linker may be branched. As above, the quantum dot/quencher pair is not critical, only that selection of the quantum dot/quencher pair ensures masking of the fluorophore. Quantum dots and their cognate quenchers are known in the art and can be selected for this purpose by one having ordinary skill in the art Upon activation of the effector proteins disclosed herein, the RNA portion of the linker molecule is cleaved thereby eliminating the proximity between the quantum dot and one or more quenchers needed to maintain the quenching effect. In certain example embodiments the quantum dot is streptavidin conjugated. RNA are attached via biotin linkers and recruit quenching molecules with the sequences /5Biosg/UCUCGUACGUUC/3IAbRQSp/ (SEQ ID NO. 34) or /5Biosg/UCUCGUACGUUCUCUCGUACGUUC/3IAbRQSp/ (SEQ ID NO. 35), where /5Biosg/ is a biotin tag and /31AbRQSp/ is an Iowa black quencher. Upon cleavage, by the activated effectors disclosed herein the quantum dot will fluoresce visibly.

In a similar fashion, fluorescence energy transfer (FRET) may be used to generate a detectable positive signal. FRET is a non-radiative process by which a photon from an energetically excited fluorophore (i.e. "donor fluorophore") raises the energy state of an electron in another molecule (i.e. "the acceptor") to higher vibrational levels of the excited singlet state. The donor fluorophore returns to the ground state without emitting a fluoresce characteristic of that fluorophore. The acceptor can be another fluorophore or non-fluorescent molecule. If the acceptor is a fluorophore, the transferred energy is emitted as fluorescence characteristic of that fluorophore. If the acceptor is a non-fluorescent molecule the absorbed energy is loss as heat. Thus, in the context of the embodiments disclosed herein, the fluorophore/quencher pair is replaced with a donor fluorophore/acceptor pair attached to the oligonucleotide molecule. When intact, the masking construct generates a first signal (negative detectable signal) as detected by the fluorescence or heat emitted from the acceptor. Upon activation of the effector proteins disclosed herein the RNA oligonucleotide is cleaved and FRET is disrupted such that fluorescence of the donor fluorophore is now detected (positive detectable signal).

In certain example embodiments, the masking construct comprises the use of intercalating dyes which change their absorbance in response to cleavage of long RNAs to short nucleotides. Several such dyes exist. For example, pyronine-Y will complex with RNA and form a complex that has an absorbance at 572 nm. Cleavage of the RNA results in loss of absorbance and a color change. Methylene blue may be used in a similar fashion, with changes in absorbance at 688 nm upon RNA cleavage. Accordingly, in certain example embodiments the masking construct comprises an RNA and intercalating dye complex that changes absorbance upon the cleavage of RNA by the effector proteins disclosed herein.

In certain example embodiments, the masking construct may comprise an initiator for an HCR reaction. Dirks and Pierce. PNAS 101, 15275-15728 (2004). HCR reactions utilize the potential energy in two hairpin species. When a single-stranded initiator having a portion of complementary to a corresponding region on one of the hairpins is released into the previously stable mixture, it opens a hairpin of one species. This process, in turn, exposes a single-stranded region that opens a hairpin of the other species. This process, in turn, exposes a single stranded region identical to the original initiator. The resulting chain reaction may lead to the formation of a nicked double helix that grows until the hairpin supply is exhausted. Detection of the resulting products may be done on a gel or colorimetrically. Example colorimetric detection methods include, for example, those disclosed in Lu et al. "Ultra-sensitive colorimetric assay system based on the hybridization chain reaction-triggered enzyme cascade amplification ACS Appl Mater Interfaces, 2017, 9 (1): 167-175, Wang et al. "An enzyme-free colorimetric assay using hybridization chain reaction amplification and split aptamers" Analyst 2015, 150, 7657-7662, and Song et al. "Non-covalent fluorescent labeling of hairpin DNA probe coupled with hybridization chain reaction for sensitive DNA detection." Applied Spectroscopy, 70 (4): 686-694 (2016).

In certain example embodiments, the masking construct may comprise a HCR initiator sequence and a cleavable structural element, such as a loop or hairpin, that prevents the initiator from initiating the HCR reaction. Upon cleavage of the structure element by an activated CRISPR effector protein, the initiator is then released to trigger the HCR reaction, detection thereof indicating the presence of one or more targets in the sample. In certain example embodiments, the masking construct comprises a hairpin with an RNA loop. When an activated CRISRP effector protein cuts the RNA loop, the initiator can be released to trigger the HCR reaction.

In certain example embodiments, the masking construct may comprise a HCR initiator sequence and a cutting motif, or a cleavable structural element, such as a loop or hairpin, that prevents the initiator from initiating the HCR reaction. The cutting motif may be preferentially cut by one of the activated CRISPR effector proteins. Upon cleavage of the cutting motif or structure element by an activated CRISPR effector protein, the initiator is then released to trigger the HCR reaction, detection thereof indicating the presence of one or more targets in the sample. In certain example embodiments, the masking construct comprises a hairpin with an RNA loop. When an activated CRISPR effector protein cuts the RNA loop, the initiator can be released to trigger the HCR reaction.

In embodiments, different orthologs with different sequence specificities may be used. Cutting motifs may be used to take advantage of the sequence specificities of different orthologs. The masking construct can comprise a cutting motif preferentially cut by a Cas protein. A cutting motif sequence can be a particular nucleotide base, a repeat nucleotide base in a homopolymer, or a heteropolymer of bases. The cutting motif can be a dinucleotide sequence, a trinucleotide sequence or more complex motifs comprising 4, 5, 6, 7, 8, 9, or 10 nucleotide motifs. For example, one orthologue may preferentially cut A, while others preferentially cut C, G, U/T. Accordingly, masking constructs completely comprising, or comprised of a substantial portion, of a single nucleotide may be generated, each with a different fluorophore that can be detected at differing wavelengths. In this way up to four different targets may be screened in a single individual discrete volume. In certain example embodiments, different orthologues from a same class of CRISPR effector protein may be used, such as two Cas13a orthologues, two Cas13b orthologues, or two Cas13c orthologues. In certain other example embodiments, different orthologues with different nucleotide editing preferences may be used such as a Cas13a and Cas13b orthologs, or a Cas13a and a Cas13c orthologs, or a Cas13b orthologs and a Cas13c orthologs etc. In certain example embodiments, a Cas13 protein with a polyU preference and a Cas13 protein with a polyA preference are used. In certain example embodiments, the Cas13 protein with a polyU preference is a *Prevotella intermedia* Cas13b, and the Cas13 protein with a poly A preference is a *Prevotella* sp. MA2106 Cas13b protein (PsmCas13b). In certain example embodiments, the Cas13 protein with a polyU preference is a *Leptotrichia wadei* Cas13a (LwaCas13a) protein and the Cas13 protein with a poly A preference is a *Prevotella* sp. MA2106 Cas13b protein. In certain example embodiments, the Cas13 protein with a polyU preference is Capnocytophaga canimorsus Cas13b protein (CcaCas13b).

Amplification of Target

In certain example embodiments, target RNAs and/or DNAs may be amplified prior to activating the CRISPR effector protein. Any suitable RNA or DNA amplification technique may be used. In certain example embodiments, the RNA or DNA amplification is an isothermal amplification. In certain example embodiments, the isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

In certain example embodiments, the RNA or DNA amplification is nucleic acid sequence-based amplification NASBA, which is initiated with reverse transcription of target RNA by a sequence-specific reverse primer to create an RNA/DNA duplex. RNase H is then used to degrade the RNA template, allowing a forward primer containing a promoter, such as the T7 promoter, to bind and initiate elongation of the complementary strand, generating a double-stranded DNA product. The RNA polymerase promoter-mediated transcription of the DNA template then creates copies of the target RNA sequence. Importantly, each of the new target RNAs can be detected by the guide RNAs thus further enhancing the sensitivity of the assay. Binding of the target RNAs by the guide RNAs then leads to activation of the CRISPR effector protein and the methods proceed as outlined above. The NASBA reaction has the additional advantage of being able to proceed under moderate isothermal conditions, for example at approximately 41° C., making it suitable for systems and devices deployed for early and direct detection in the field and far from clinical laboratories.

In certain other example embodiments, a recombinase polymerase amplification (RPA) reaction may be used to amplify the target nucleic acids. RPA reactions employ recombinases which are capable of pairing sequence-specific primers with homologous sequence in duplex DNA. If target DNA is present, DNA amplification is initiated and no other sample manipulation such as thermal cycling or chemical melting is required. The entire RPA amplification system is stable as a dried formulation and can be transported safely without refrigeration. RPA reactions may also be carried out at isothermal temperatures with an optimum reaction temperature of 37-42° C. The sequence specific primers are designed to amplify a sequence comprising the target nucleic acid sequence to be detected. In certain example embodiments, an RNA polymerase promoter, such as a T7 promoter, is added to one of the primers. This results in an amplified double-stranded DNA product comprising the target sequence and an RNA polymerase promoter. After, or during, the RPA reaction, an RNA polymerase is added that will produce RNA from the double-stranded DNA templates. The amplified target RNA can then in turn be detected by the CRISPR effector system. In this way target DNA can be detected using the embodiments disclosed herein. RPA reactions can also be used to amplify target RNA. The target RNA is first converted to cDNA using a reverse transcriptase, followed by second strand DNA synthesis, at which point the RPA reaction proceeds as outlined above.

Accordingly, in certain example embodiments, the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride (MgCl2), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate [(NH4)2SO4], or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful for the invention, including Taq polymerase, Q5 polymerase, or the like.

In some embodiments, amplification reagents as described herein may be appropriate for use in hot-start amplification. Hot start amplification may be beneficial in some embodiments to reduce or eliminate dimerization of adaptor molecules or oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or apatamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment and may be performed in single reactions or in bulk, such that any desired number of reactions may be performed simultaneously. In some embodiments, amplification may be performed using microfluidic or robotic devices or may be performed using manual alteration in temperatures to achieve the desired amplification. In some embodiments, optimization may be performed to obtain the optimum reaction conditions for the particular application or materials. One of skill in the art will understand and be able to optimize reaction conditions to obtain sufficient amplification.

In certain embodiments, detection of DNA with the methods or systems of the invention requires transcription of the (amplified) DNA into RNA prior to detection.

In certain example embodiments, further modifications may be introduced that further amplify the detectable positive signal. For example, activated CRISPR effector protein collateral activation may be used to generate a secondary target or additional guide sequence, or both. In one example embodiment, the reaction solution would contain a secondary target that is spiked in at high concentration. The secondary target may be distinct from the primary target (i.e. the target for which the assay is designed to detect) and in certain instances may be common across all reaction volumes. A secondary guide sequence for the secondary target may be protected, e.g. by a secondary structural feature such as a hairpin with an RNA loop, and unable to bind the second target or the CRISPR effector protein. Cleavage of the protecting group by an activated CRISPR effector protein (i.e. after activation by formation of complex with the primary target(s) in solution) and formation of a complex with free CRISPR effector protein in solution and activation from the spiked in secondary target. In certain other example embodiments, a similar concept is used with free guide sequence to a secondary target and protected secondary target. Cleavage of a protecting group off the secondary target would allow additional CRISPR effector protein, guide sequence, secondary target sequence to form. In yet another example embodiment, activation of CRISPR effector protein by the primary target(s) may be used to cleave a protected or circularized primer, which would then be released to perform an isothermal amplification reaction, such as those disclosed herein, on a template for either secondary guide sequence, secondary target, or both. Subsequent transcription of this amplified template would produce more secondary guide sequence and/or secondary target sequence, followed by additional CRISPR effector protein collateral activation.

In some embodiments, the target molecule comprises a SNP, as described herein. In specific embodiments, the guide RNA is designed to bind to *B. microti* comprising a SNP cytB M134I.

Lateral Flow Devices

The embodiments disclosed herein are directed to lateral flow detection devices that comprise SHERLOCK systems. Reference is made to Gootenberg, et al., "Multiplexed and portable nucleic acid detection platform with Cas13, Cas12a, and Csm6," Science. 2018 Apr. 27; 360 (6387): 439-444. doi: 10.1126/science.aaq0179, and International Patent Publication No, WO 2019/071051, each specifically incorporated herein by reference. The device may comprise a lateral flow substrate for detecting a SHERLOCK reaction. Substrates suitable for use in lateral flow assays are known in the art. These may include, but are not necessarily limited to, membranes or pads made of cellulose and/or glass fiber, polyesters, nitrocellulose, or absorbent pads (J Saudi Chem Soc 19 (6): 689-705; 2015). The SHERLOCK system, i.e. one or more CRISPR systems and corresponding reporter constructs are added to the lateral flow substrate at a defined reagent portion of the lateral flow substrate, typically on one end of the lateral flow substrate. Reporting constructs used within the context of the present invention comprise a first molecule and a second molecule linked by an RNA or DNA linker. The lateral flow substrate further comprises a sample portion. The sample portion may be equivalent to, continuous with, or adjacent to the reagent portion. The lateral flow strip further comprises a first capture line, typically a horizontal line running across the device, but other configurations are possible. The first capture region is proximate to and on the same end of the lateral flow substrate as the sample loading portion. A first binding agent that specifically binds the first molecule of the reporter construct is fixed or otherwise immobilized to the first capture region. The second capture region is located towards the opposite end of the lateral flow substrate from the first binding region. A second binding agent is fixed or otherwise immobilized at the second capture region. The second binding agent specifically binds the second molecule of the reporter construct, or the second binding agent may bind a detectable ligand. For example, the detectable ligand may be a particle, such as a colloidal particle, that when it aggregates can be detected visually. The particle may be modified with an antibody that specifically binds the second molecule on the reporter construct. If the reporter construct is not cleaved, it will facilitate accumulation of the detectable ligand at the first binding region. If the reporter construct is cleaved the detectable ligand is released to flow to the second binding region. In such an embodiment, the second binding agent is an agent capable of specifically or non-specifically binding the detectable ligand on the antibody on the detectable ligand. Examples of suitable binding agents for such an embodiment include, but are not limited to, protein A and protein G.

Lateral support substrates may be located within a housing (see for example, "Rapid Lateral Flow Test Strips" Merck Millipore 2013). The housing may comprise at least one opening for loading samples and a second single opening or separate openings that allow for reading of detectable signal generated at the first and second capture regions.

The SHERLOCK system may be freeze-dried to the lateral flow substrate and packaged as a ready to use device, or the SHERLOCK system may be added to the reagent portion of the lateral flow substrate at the time of using the device. Samples to be screened are loaded at the sample loading portion of the lateral flow substrate. The samples must be liquid samples or samples dissolved in an appropriate solvent, usually aqueous. The liquid sample reconstitutes the SHERLOCK reagents such that a SHERLOCK reaction can occur. The liquid sample begins to flow from the sample portion of the substrate towards the first and second capture regions. Intact reporter construct is bound at the first capture region by binding between the first binding agent and the first molecule. Likewise, the detection agent will begin to collect at the first binding region by binding to the second molecule on the intact reporter construct. If target molecule(s) are present in the sample, the CRISPR effector protein collateral effect is activated. As activated CRISPR effector protein comes into contact with the bound reporter construct, the reporter constructs are cleaved, releasing the second molecule to flow further down the lateral flow substrate towards the second binding region. The released second molecule is then captured at the second capture region by binding to the second binding agent, where additional detection agent may also accumulate by binding to the second molecule. Accordingly, if the target molecule(s) is not present in the sample, a detectable signal will appear at the first capture region, and if the target molecule(s) is present in the sample, a detectable signal will appear at the location of the second capture region.

Specific binding-integrating molecules comprise any members of binding pairs that can be used in the present invention. Such binding pairs are known to those skilled in the art and include, but are not limited to, antibody-antigen pairs, enzyme-substrate pairs, receptor-ligand pairs, and streptavidin-biotin. In addition to such known binding pairs, novel binding pairs may be specifically designed. A characteristic of binding pairs is the binding between the two members of the binding pair.

Oligonucleotide Linkers having molecules on either end may comprise DNA if the CRISPR effector protein has DNA collateral activity (Cpf1 and C2c1) or RNA if the CRISPR effector protein has RNA collateral activity. Oligonucleotide linkers may be single stranded or double stranded, and in certain embodiments, they could contain both RNA and DNA regions. Oligonucleotide linkers may be of varying lengths, such as 5-10 nucleotides, 10-20 nucleotides, 20-50 nucleotides, or more.

In some embodiments, the polypeptide identifier elements include affinity tags, such as hemagglutinin (HA) tags, Myc tags, FLAG tags, V5 tags, chitin binding protein (CBP) tags, maltose-binding protein (MBP) tags, GST tags, poly-His tags, and fluorescent proteins (for example, green fluorescent protein (GFP), yellow fluorescent protein (YFP), cyan fluorescent protein (CFP), dsRed, mCherry, Kaede, Kindling, and derivatives thereof, FLAG tags, Myc tags, AU1 tags, T7 tags, OLLAS tags, Glu-Glu tags, VSV tags, or a combination thereof. Other Affinity tags are well known in the art. Such labels can be detected and/or isolated using methods known in the art (for example, by using specific binding agents, such as antibodies, that recognize a particular affinity tag). Such specific binding agents (for example, antibodies) can further contain, for example, detectable labels, such as isotope labels and/or nucleic acid barcodes such as those described herein.

For instance, a lateral flow strip allows for RNAse (e.g. Cas13a) detection by color. The RNA reporter is modified to have a first molecule (such as for instance FITC) attached to the 5' end and a second molecule (such as for instance biotin) attached to the 3' end (or vice versa). The lateral flow strip is designed to have two capture lines with anti-first molecule (e.g. anti-FITC) antibodies hybridized at the first line and anti-second molecule (e.g. anti-biotin) antibodies at the second downstream line. As the SHERLOCK reaction flows down the strip, uncleaved reporter will bind to anti-first molecule antibodies at the first capture line, while cleaved reporters will liberate the second molecule and allow second molecule binding at the second capture line. Second molecule sandwich antibodies, for instance conjugated to nanoparticles, such as gold nanoparticles, will bind any second molecule at the first or second line and result in a strong readout/signal (e.g. color). As more reporter is cleaved, more signal will accumulate at the second capture line and less signal will appear at the first line. In certain aspects, the invention relates to the use of a follow strip as described herein for detecting nucleic acids or polypeptides. In certain aspects, the invention relates to a method for detecting nucleic acids or polypeptides with a flow strip as defined herein, e.g. (lateral) flow tests or (lateral) flow immunochromatographic assays.

In specific embodiments, the RNA reporter construct may comprise a first molecule on a first end and a second molecule on a second end. The first molecule may be FITC, and the second molecule may be biotin, or vice versa. In specific embodiments, the first capture region may comprise a first binding agent that specifically binds the first molecule of the reporter construct. The first binding agent may be an antibody that is fixed or otherwise immobilized to the first capture region. The second capture region may comprise a second binding agent that specifically binds the second molecule of the reporter construct, or the detectable ligand. The second binding agent may be an antibody or an antibody-binding protein that is fixed or otherwise immobilized to the second capture region.

In certain example embodiments, a lateral flow device comprises a lateral flow substrate comprising a first end for application of a sample. The first region is loaded with a detectable ligand, such as those disclosed herein, for example a gold nanoparticle. The gold nanoparticle may be modified with a first antibody, such as an anti-FITC antibody. The first region also comprises a detection construct. In one example embodiment, an RNA detection construct and a CRISPR effector system (a CRISPR effector protein and one or more guide sequences configured to bind to one or more target sequences) as disclosed herein. In one example embodiment, and for purposes of further illustration, the RNA construct may comprise a FAM molecule on a first end of the detection construction and a biotin on a second end of the detection construct. Upstream of the flow of solution from the first end of the lateral flow substrate is a first test band. The test band may comprise a biotin ligand. Accordingly, when the RNA detection construct is present it its initial state, i.e. in the absence of target, the FAM molecule on the first end will bind the anti-FITC antibody on the gold nanoparticle, and the biotin on the second end of the RNA construct will bind the biotin ligand allowing for the detectable ligand to accumulate at the first test, generating a detectable signal. Generation of a detectable signal at the first band indicate the absence of the target ligand. In the presence of target, the CRISPR effector complex forms and the CRISPR effector protein is activated resulting in cleavage of the RNA detection construct. In the absence of intact RNA detection construct the colloidal gold will flow past the second strip. The lateral flow device may comprise a second band, upstream of the first band. The second band may comprise a molecule capable of binding the antibody-labeled colloidal gold molecule, for example an anti-rabbit antibody capable of binding a rabbit anti-FTIC antibody on the colloidal gold. Therefore, in the presence of one or more targets, the detectable ligand will accumulate at the second band, indicating the presence of the one or more targets in the sample.

Microbial Clustered Regularly Interspaced Short Palindromic Repeats (CRISPR) and CRISPR-associated (CRISPR-Cas) adaptive immune systems contain programmable endonucleases, such as Cas9 and Cpf1 (Shmakov et al., 2017; Zetsche et al., 2015). Although both Cas9 and Cpf1 target DNA, single effector RNA-guided RNases have been recently discovered (Shmakov et al., 2015) and characterized (Abudayyeh et al., 2016; Smargon et al., 2017), including C2c2, providing a platform for specific RNA sensing. RNA-guided RNases can be easily and conveniently reprogrammed using CRISPR RNA (crRNAs) to cleave target RNAs. Unlike the DNA endonucleases Cas9 and Cpf1, which cleave only its DNA target, RNA-guided RNases, like C2c2, remain active after cleaving their RNA target, leading to "collateral" cleavage of non-targeted RNAs in proximity (Abudayyeh et al., 2016). This crRNA-programmed collateral RNA cleavage activity presents the opportunity to use RNA-guided RNases to detect the presence of a specific RNA by triggering in vivo programmed cell death or in vitro nonspecific RNA degradation that can serve as a readout (Abudayyeh et al., 2016; East-Seletsky et al., 2016). Collateral activity has also been recognized in other CRISPR Cas enzymes [lead flag for me to provide cites for Cpf1 and C2c1 collateral activity].

In specific embodiments, lateral flow device comprises a substrate comprising a first end, wherein the first end comprises a sample loading portion and a first region loaded with a detectable ligand, the nucleic acid detection system, a first capture region comprising a first binding agent, and a second capture region comprising a second binding agent.

In specific embodiments, the sample loading portion may further comprise one or more amplification reagents to amplify the one or more target molecules, as described elsewhere herein. The reagents may comprise regents for nucleic acid sequence-based amplification (NASBA), recombinase polymerase amplification (RPA), loop-mediated isothermal amplification (LAMP), strand displacement amplification (SDA), helicase-dependent amplification (HDA), nicking enzyme amplification reaction (NEAR), PCR, multiple displacement amplification (MDA), rolling circle amplification (RCA), ligase chain reaction (LCR), or ramification amplification method (RAM), as described elsewhere herein.

Sample Types

Appropriate samples for use in the methods disclosed herein include any conventional biological sample obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including, without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as an infection with a pathogenic microorganism, such as a pathogenic bacterium or virus). For example, a biological sample can be a biological fluid obtained from, for example, blood, plasma, serum, urine, stool, sputum, mucous, lymph fluid, synovial fluid, bile, ascites, pleural effusion, seroma, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis), or a swab of skin or mucosal membrane surface.

A sample can also be a sample obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will be appreciated that any method of obtaining tissue from a subject can be utilized, and that the selection of the method used will depend upon various factors such as the type of tissue, age of the subject, or procedures available to the practitioner. Standard techniques for acquisition of such samples are available in the art. See, for example Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984). In some embodiments the sample may be a cell free DNA sample.

In other embodiments, a sample may be an environmental sample, such as water, soil, or a surface such as industrial or medical surface. In some embodiments, methods such as those disclosed in US patent publication No. 2013/0190196 may be applied for detection of nucleic acid signatures, specifically RNA levels, directly from crude cellular samples with a high degree of sensitivity and specificity. Sequences specific to each pathogen of interest may be identified or selected by comparing the coding sequences from the pathogen of interest to all coding sequences in other organisms by BLAST software.

Several embodiments of the present disclosure involve the use of procedures and approaches known in the art to successfully fractionate clinical blood samples. See, e.g. the procedure described in Han Wei Hou et al., Microfluidic Devices for Blood Fractionation, Micromachines 2011, 2, 319-343; Ali Asgar S. Bhagat et al., Dean Flow Fractionation (DFF) Isolation of Circulating Tumor Cells (CTCs) from Blood, 15th International Conference on Miniaturized Systems for Chemistry and Life Sciences, Oct. 2-6, 2011, Seattle, WA; and International Patent Publication No. WO2011109762, the disclosures of which are herein incorporated by reference in their entirety. Blood samples are commonly expanded in culture to increase sample size for testing purposes. In some embodiments of the present invention, blood or other biological samples may be used in methods as described herein without the need for expansion in culture.

Further, several embodiments of the present disclosure involve the use of procedures and approaches known in the art to successfully isolate pathogens from whole blood using spiral microchannel, as described in Han Wei Hou et al., Pathogen Isolation from Whole Blood Using Spiral Microchannel, Case No. 15995JR, Massachusetts Institute of Technology, manuscript in preparation, the disclosure of which is herein incorporated by reference in its entirety.

Owing to the increased sensitivity of the embodiments disclosed herein, in certain example embodiments, the assays and methods may be run on crude samples or samples where the target molecules to be detected are not further fractionated or purified from the sample.

In specific embodiments, the sample loading portion comprises a receiving input for a blood stick.

Methods for Detecting Target Nucleic Acids

The invention also provides methods for detecting target nucleic acids in a sample. Such methods may comprise distributing a sample or set of samples into one or more individual discrete volumes.

An "individual discrete volume" is a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents maybe passed in or through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

In some embodiments, the individual discrete volumes may comprise a nucleic acid detection system as described herein.

In some embodiments, the sample may be blood, RBC supernatant, plasma, cerebrospinal fluid, as described herein.

In some embodiments, the method may further comprise the steps of i) incubating the sample at 37-50° C. for 5-20 minutes; ii) incubating the sample at 64-95° C. for 5 minutes; iii) performing RT-RPA; iv) performing T7 transcription; and v) detecting the target nucleic acids.

In some embodiments, the method may further comprise treating the sample with heat, optionally at 99° C. for 10 minutes.

In some embodiments, target nucleic acid may be from a sample of cell free DNA as described herein.

In some embodiments, the target nucleic acid may be DNA and the method may further comprise the step of extracting DNA from cells in the sample. In certain embodiments, the present invention provides steps of obtaining a sample of biological fluid (e.g., urine, blood plasma or serum, sputum, cerebral spinal fluid), and extracting the DNA. The mutant nucleotide sequence to be detected, may be a fraction of a larger molecule or can be present initially as a discrete molecule. In certain embodiments, blood samples are collected and plasma immediately separated from the blood cells by centrifugation. Serum may be filtered and stored frozen until DNA extraction.

In some embodiments, the sample may be collected on a Whatman FTA card, as described in the Examples. The method may further comprise eluting the sample from the FTA card.

Example Methods and Assays

The low cost and adaptability of the assay platform lends itself to a number of applications including (i) general RNA/DNA quantitation, (ii) rapid, multiplexed RNA/DNA expression detection, and (iii) sensitive detection of target nucleic acids, peptides in both clinical and environmental samples. Additionally, the systems disclosed herein may be adapted for detection of transcripts within biological settings, such as cells. Given the highly specific nature of the CRISPR effectors described herein, it may be possible to track allelic specific expression of transcripts or disease-associated mutations in live cells.

In certain example embodiments, a single guide sequence specific to a single target is placed in separate volumes. Each volume may then receive a different sample or aliquot of the same sample. In certain example embodiments, multiple guide sequences each to a separate target may be placed in a single well such that multiple targets may be screened in a different well. In order to detect multiple guide RNAs in a single volume, in certain example embodiments, multiple effector proteins with different specificities may be used. For example, different orthologs with different sequence specificities may be used. For example, one orthologue may preferentially cut A, while others preferentially cut C, G, U/T. Accordingly, masking constructs that are all, or comprise a substantial portion, of a single nucleotide may be generated, each with a different fluorophore which can be detected at differing wavelengths. Reference is made to Gootenberg, et al., "Multiplexed and portable nucleic acid detection platform with Cas13, Cas12a, and Csm6," Science. 2018 Apr. 27; 360 (6387): 439-444. doi: 10.1126/science.aaq0179, and WO 2019/126577, incorporated by reference in their entirety. In this way, up to four different targets may be screened in a single individual discrete volume. In certain example embodiments, different orthologues from a same class of CRISPR effector protein may be used, such as two Cas13a orthologues, two Cas13b orthologues, or two Cas13 orthologues. In certain other example embodiments, different orthologues with different nucleotide editing preferences may be used, such as a Cas13a and a Cas13b ortholog, or a Cas13a and a Cas13c ortholog, or a Cas13b ortholog and a Cas13c ortholog etc. In certain example embodiments, a Cas13 protein with a polyU preference and a Cas13b protein with a polyA preference are used. In certain example embodiments, the Cas13b protein with a polyU preference is a *Prevotella intermedia* Cas13b and the Cas13b protein with a polyA preference is a *Prevotella* sp. MA2106 Cas13b protein. In certain example embodiments, the Cas13 protein with a polyU preference is a *Leptotrichia wadei* Cas13a protein and the Cas13 protein with a poly A preference is a *Prevotella* sp. MA2106 Cas13b protein.

As demonstrated herein, the CRISPR effector systems are capable of detecting down to attomolar concentrations of target molecules. See e.g. Examples described below. Due to the sensitivity of said systems, a number of applications that require rapid and sensitive detection may benefit from the embodiments disclosed herein and are contemplated to be within the scope of the invention. Example assays and applications are described in further detail below.

Microbial Applications

In certain example embodiments, the systems, devices, and methods, disclosed herein are directed to detecting the presence of one or more microbial agents in a sample, such as a biological sample obtained from a subject. In certain example embodiments, the microbe may be a bacterium, a fungus, a yeast, a protozoan, a parasite, or a virus. Accordingly, the methods disclosed herein can be adapted for use in other methods (or in combination) with other methods that require quick identification of microbe species, monitoring the presence of microbial proteins (antigens), antibodies, antibody genes, detection of certain phenotypes (e.g. bacterial resistance), monitoring of disease progression and/or outbreak, and antibiotic screening. Because of the rapid and sensitive diagnostic capabilities of the embodiments disclosed here, detection of microbe species type, down to a single nucleotide difference, and the ability to be deployed as a POC device, the embodiments disclosed herein may be used as guide therapeutic regimens, such as a selection of the appropriate antibiotic or antiviral. The embodiments disclosed herein may also be used to screen environmental samples (air, water, surfaces, food etc.) for the presence of microbial contamination.

Disclosed is a method to identify microbial species, such as bacterial, viral, fungal, yeast, or parasitic species, or the like. Particular embodiments disclosed herein describe methods and systems that will identify and distinguish microbial species within a single sample, or across multiple samples, allowing for recognition of many different microbes. The present methods allow the detection of pathogens and distinguishing between two or more species of one or more organisms, e.g., bacteria, viruses, yeast, protozoa, and fungi or a combination thereof, in a biological or environmental sample, by detecting the presence of a target nucleic acid sequence in the sample. A detectable signal obtained from the sample indicates the presence of the microbe. Multiple microbes can be identified simultaneously using the methods and systems of the invention, by employing the use of more than one effector protein, wherein each effector protein targets a specific microbial target sequence. In this way, a multi-level analysis can be performed for a particular subject in which any number of microbes can be detected at once. In some embodiments, simultaneous detection of multiple microbes may be performed using a set of probes that can identify one or more microbial species.

Multiplex analysis of samples enables large-scale detection of samples, reducing the time and cost of analyses. However, multiplex analyses are often limited by the availability of a biological sample. In accordance with the invention, however, alternatives to multiplex analysis may be performed such that multiple effector proteins can be added to a single sample and each masking construct may be combined with a separate quencher dye. In this case, positive signals may be obtained from each quencher dye separately for multiple detection in a single sample.

Disclosed herein are methods for distinguishing between two or more species of one or more organisms in a sample. The methods are also amenable to detecting one or more species of one or more organisms in a sample.

Microbe Detection

In some embodiments, a method for detecting microbes in samples is provided comprising distributing a sample or set of samples into one or more individual discrete volumes, the individual discrete volumes comprising a CRISPR system as described herein; incubating the sample or set of samples under conditions sufficient to allow binding of the one or more guide RNAs to one or more microbe-specific targets; activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules in the sample. The one or more target molecules may be mRNA, gDNA (coding or non-coding), trRNA, or RNA comprising a target nucleotide tide sequence that may be used to distinguish two or more microbial species/strains from one another. The guide RNAs may be designed to detect target sequences. The embodiments disclosed herein may also utilize certain steps to improve hybridization between guide RNA and target RNA sequences. Methods for enhancing ribonucleic acid hybridization are disclosed in WO 2015/085194, entitled "Enhanced Methods of Ribonucleic Acid Hybridization" which is incorporated herein by reference. The microbe-specific target may be RNA or DNA or a protein. A DNA method may further comprise the use of DNA primers that introduce an RNA polymerase promoter as described herein. If the target is a protein then the method will utilize aptamers and steps specific to protein detection described herein.

Detection of Single Nucleotide Variants

In some embodiments, one or more identified target sequences may be detected using guide RNAs that are specific for and bind to the target sequence as described herein. The systems and methods of the present invention can distinguish even between single nucleotide polymorphisms present among different microbial species and therefore, use of multiple guide RNAs in accordance with the invention may further expand on or improve the number of target sequences that may be used to distinguish between species. For example, in some embodiments, the one or more guide RNAs may distinguish between microbes at the species, genus, family, order, class, phylum, kingdom, or phenotype, or a combination thereof.

Detection Based on rRNA Sequences

In certain example embodiments, the devices, systems, and methods disclosed herein may be used to distinguish multiple microbial species in a sample. In certain example embodiments, identification may be based on ribosomal RNA sequences, including the 16S, 23S, and 5S subunits. Methods for identifying relevant rRNA sequences are disclosed in U.S. Patent Application Publication No. 2017/0029872. In certain example embodiments, a set of guide RNAs may be designed to distinguish each species by a variable region that is unique to each species or strain. Guide RNAs may also be designed to target RNA genes that distinguish microbes at the genus, family, order, class, phylum, or kingdom levels, or a combination thereof. In certain example embodiments where amplification is used, a set of amplification primers may be designed to flanking constant regions of the ribosomal RNA sequence and a guide RNA designed to distinguish each species by a variable internal region. In certain example embodiments, the primers and guide RNAs may be designed to conserved and variable regions in the 16S subunit respectfully. Other genes or genomic regions that are uniquely variable across species or a subset of species such as the RecA gene family, RNA polymerase β subunit, may be used as well. Other suitable phylogenetic markers, and methods for identifying the same, are discussed for example in Wu et al. arXiv: 1307.8690 [q-bio.GN].

In certain example embodiments, a method or diagnostic is designed to screen microbes across multiple phylogenetic and/or phenotypic levels at the same time. For example, the method or diagnostic may comprise the use of multiple CRISPR systems with different guide RNAs. A first set of guide RNAs may distinguish, for example, between mycobacteria, gram-positive, and gram-negative bacteria. These general classes can be even further subdivided. For example, guide RNAs could be designed and used in the method or diagnostic that distinguish enteric and non-enteric within gram negative bacteria. A second set of guide RNAs can be designed to distinguish microbes at the genus or species level. Thus, a matrix may be produced identifying all mycobacteria, gram positive, gram negative (further divided into enteric and non-enteric) with each genus of species of bacteria identified in a given sample that fall within one of those classes. The foregoing is for example purposes only. Other means for classifying other microbe types are also contemplated and would follow the general structure described above.

Screening for Drug Resistance

In certain example embodiments, the devices, systems and methods disclosed herein may be used to screen for microbial genes of interest, for example antibiotic and/or antiviral resistance genes. Guide RNAs may be designed to distinguish between known genes of interest. Samples, including clinical samples, may then be screened using the embodiments disclosed herein for detection of such genes. The ability to screen for drug resistance at POC would have tremendous benefit in selecting an appropriate treatment regime. In certain example embodiments, the antibiotic resistance genes are carbapenemases including KPC, NDM1, CTX-M15, OXA-48. Other antibiotic resistance genes are known and may be found for example in the Comprehensive Antibiotic Resistance Database (Jia et al. "CARD 2017: expansion and model-centric curation of the Comprehensive Antibiotic Resistance Database." Nucleic Acids Research, 45, D566-573).

Ribavirin is an effective antiviral that hits a number of RNA viruses. Several clinically important viruses have evolved ribavirin resistance, including Foot and Mouth Disease Virus doi: 10.1128/JVI.03594-13; polio virus (Pfeifer and Kirkegaard. PNAS, 100 (12): 7289-7294, 2003); and hepatitis C virus (Pfeiffer and Kirkegaard, J. Virol. 79

(4): 2346-2355, 2005). A number of other persistent RNA viruses, such as hepatitis and HIV, have evolved resistance to existing antiviral drugs: hepatitis B virus (lamivudine, tenofovir, entecavir) doi: 10/1002/hep22900; hepatitis C virus (telaprevir, BILN2061, ITMN-191, SCh6, boceprevir, AG-021541, ACH-806) doi: 10.1002/hep.22549; and HIV (many drug resistance mutations) hivb.standford.edu. The embodiments disclosed herein may be used to detect such variants among others.

Aside from drug resistance, there are a number of clinically relevant mutations that could be detected with the embodiments disclosed herein, such as persistent versus acute infection in LCMV (doi: 10.1073/pnas. 1019304108), and increased infectivity of Ebola (Diehl et al. Cell. 2016, 167 (4): 1088-1098.

As described herein elsewhere, closely related microbial species (e.g. having only a single nucleotide difference in a given target sequence) may be distinguished by introduction of a synthetic mismatch in the gRNA.

Set Cover Approaches

In particular embodiments, a set of guide RNAs is designed that can identify, for example, all microbial species within a defined set of microbes. Such methods are described in certain example embodiments; the methods for generating guide RNAs as described herein may be compared to methods disclosed in WO 2017/040316, incorporated herein by reference. As described in WO 2017040316, a set cover solution may identify the minimal number of target sequences probes or guide RNAs needed to cover an entire target sequence or set of target sequences, e.g. a set of genomic sequences. Set cover approaches have been used previously to identify primers and/or microarray probes, typically in the 20 to 50 base pair range. See, e.g. Pearson et al., cs.virginia.edu/~robins/papers/primers_dam11_final.pdf., Jabado et al. Nucleic Acids Res. 2006 34 (22): 6605-11, Jabado et al. Nucleic Acids Res. 2008, 36 (1): e3 doi 10.1093/nar/gkm1106, Duitama et al. Nucleic Acids Res. 2009, 37 (8): 2483-2492, Phillippy et al. BMC Bioinformatics. 2009, 10:293 doi: 10.1186/1471-2105-10-293. However, such approaches generally involved treating each primer/probe as k-mers and searching for exact matches or allowing for inexact matches using suffix arrays. In addition, the methods generally take a binary approach to detecting hybridization by selecting primers or probes such that each input sequence only needs to be bound by one primer or probe and the position of this binding along the sequence is irrelevant. Alternative methods may divide a target genome into pre-defined windows and effectively treat each window as a separate input sequence under the binary approach—i.e. they determine whether a given probe or guide RNA binds within each window and require that all of the windows be bound by the state of some probe or guide RNA. Effectively, these approaches treat each element of the "universe" in the set cover problem as being either an entire input sequence or a pre-defined window of an input sequence, and each element is considered "covered" if the start of a probe or guide RNA binds within the element. These approaches limit the fluidity to which different probe or guide RNA designs are allowed to cover a given target sequence.

In contrast, the embodiments disclosed herein are directed to detecting longer probe or guide RNA lengths, for example, in the range of 70 bp to 200 bp that are suitable for hybrid selection sequencing. In addition, the methods disclosed herein may be applied to take a pan-target sequence approach capable of defining a probe or guide RNA sets that can identify and facilitate the detection sequencing of all species and/or strain sequences in a large and/or variable target sequence set. For example, the methods disclosed herein may be used to identify all variants of a given virus, or multiple different viruses in a single assay. Further, the method disclosed herein treats each element of the "universe" in the set cover problem as being a nucleotide of a target sequence, and each element is considered "covered" as long as a probe or guide RNA binds to some segment of a target genome that includes the element. These types of set cover methods may be used instead of the binary approach of previous methods, the methods disclosed herein better model how a probe or guide RNA may hybridize to a target sequence. Rather than only asking if a given guide RNA sequence does or does not bind to a given window, such approaches may be used to detect a hybridization pattern— i.e. where a given probe or guide RNA binds to a target sequence or target sequences- and then determines from those hybridization patterns the minimum number of probes or guide RNAs needed to cover the set of target sequences to a degree sufficient to enable both enrichment from a sample and sequencing of any and all target sequences. These hybridization patterns may be determined by defining certain parameters that minimize a loss function, thereby enabling identification of minimal probe or guide RNA sets in a way that allows parameters to vary for each species, e.g. to reflect the diversity of each species, as well as in a computationally efficient manner that cannot be achieved using a straightforward application of a set cover solution, such as those previously applied in the probe or guide RNA design context.

The ability to detect multiple transcript abundances may allow for the generation of unique microbial signatures indicative of a particular phenotype. Various machine learning techniques may be used to derive the gene signatures. Accordingly, the guide RNAs of the CRISPR systems may be used to identify and/or quantitate relative levels of biomarkers defined by the gene signature in order to detect certain phenotypes. In certain example embodiments, the gene signature indicates susceptibility to an antibiotic, resistance to an antibiotic, or a combination thereof.

In one aspect of the invention, a method comprises detecting one or more pathogens. In this manner, differentiation between infection of a subject by individual microbes may be obtained. In some embodiments, such differentiation may enable detection or diagnosis by a clinician of specific diseases, for example, different variants of a disease. Preferably the pathogen sequence is a genome of the pathogen or a fragment thereof. The method further may comprise determining the evolution of the pathogen. Determining the evolution of the pathogen may comprise identification of pathogen mutations, e.g. nucleotide deletion, nucleotide insertion, nucleotide substitution. Amongst the latter, there are non-synonymous, synonymous, and noncoding substitutions. Mutations are more frequently non-synonymous during an outbreak. The method may further comprise determining the substitution rate between two pathogen sequences analyzed as described above. Whether the mutations are deleterious or even adaptive would require functional analysis, however, the rate of non-synonymous mutations suggests that continued progression of this epidemic could afford an opportunity for pathogen adaptation, underscoring the need for rapid containment. Thus, the method may further comprise assessing the risk of viral adaptation, wherein the number non-synonymous mutations is determined (Gire, et al., Science 345, 1369, 2014).

Monitoring Microbe Outbreaks

In some embodiments, a CRISPR system or methods of use thereof as described herein may be used to determine the evolution of a pathogen outbreak. The method may comprise detecting one or more target sequences from a plurality of samples from one or more subjects, wherein the target sequence is a sequence from a microbe causing the outbreaks. Such a method may further comprise determining a pattern of pathogen transmission, or a mechanism involved in a disease outbreak caused by a pathogen.

The pattern of pathogen transmission may comprise continued new transmissions from the natural reservoir of the pathogen or subject-to-subject transmissions (e.g. human-to-human transmission) following a single transmission from the natural reservoir or a mixture of both. In one embodiment, the pathogen transmission may be bacterial or viral transmission, in such case, the target sequence is preferably a microbial genome or fragments thereof. In one embodiment, the pattern of the pathogen transmission is the early pattern of the pathogen transmission, i.e. at the beginning of the pathogen outbreak. Determining the pattern of the pathogen transmission at the beginning of the outbreak increases likelihood of stopping the outbreak at the earliest possible time thereby reducing the possibility of local and international dissemination.

Determining the pattern of the pathogen transmission may comprise detecting a pathogen sequence according to the methods described herein. Determining the pattern of the pathogen transmission may further comprise detecting shared intra-host variations of the pathogen sequence between the subjects and determining whether the shared intra-host variations show temporal patterns. Patterns in observed intrahost and interhost variation provide important insight about transmission and epidemiology (Gire, et al., 2014).

Detection of shared intra-host variations between the subjects that show temporal patterns is an indication of transmission links between subjects (in particular between humans) because it can be explained by subject infection from multiple sources (superinfection), sample contamination recurring mutations (with or without balancing selection to reinforce mutations), or co-transmission of slightly divergent viruses that arose by mutation earlier in the transmission chain (Park, et al., Cell 161 (7): 1516-1526, 2015). Detection of shared intra-host variations between subjects may comprise detection of intra-host variants located at common single nucleotide polymorphism (SNP) positions. Positive detection of intra-host variants located at common (SNP) positions is indicative of superinfection and contamination as primary explanations for the intra-host variants. Superinfection and contamination can be parted on the basis of SNP frequency appearing as inter-host variants (Park, et al., 2015). Otherwise superinfection and contamination can be ruled out. In this latter case, detection of shared intra-host variations between subjects may further comprise assessing the frequencies of synonymous and nonsynonymous variants and comparing the frequency of synonymous and nonsynonymous variants to one another. A nonsynonymous mutation is a mutation that alters the amino acid of the protein, likely resulting in a biological change in the microbe that is subject to natural selection. Synonymous substitution does not alter an amino acid sequence. Equal frequency of synonymous and nonsynonymous variants is indicative of the intra-host variants evolving neutrally. If frequencies of synonymous and nonsynonymous variants are divergent, the intra-host variants are likely to be maintained by balancing selection. If frequencies of synonymous and nonsynonymous variants are low, this is indicative of recurrent mutation. If frequencies of synonymous and nonsynonymous variants are high, this is indicative of co-transmission (Park, et al., 2015).

Like Ebola virus, Lassa virus (LASV) can cause hemorrhagic fever with high case fatality rates. Andersen et al. generated a genomic catalog of almost 200 LASV sequences from clinical and rodent reservoir samples (Andersen, et al., Cell Volume 162, Issue 4, p 738-750, 13 Aug. 2015). Andersen et al. show that whereas the 2013-2015 EVD epidemic is fueled by human-to-human transmissions, LASV infections mainly result from reservoir-to-human infections. Andersen et al. elucidated the spread of LASV across West Africa and show that this migration was accompanied by changes in LASV genome abundance, fatality rates, codon adaptation, and translational efficiency. The method may further comprise phylogenetically comparing a first pathogen sequence to a second pathogen sequence, and determining whether there is a phylogenetic link between the first and second pathogen sequences. The second pathogen sequence may be an earlier reference sequence. If there is a phylogenetic link, the method may further comprise rooting the phylogeny of the first pathogen sequence to the second pathogen sequence. Thus, it is possible to construct the lineage of the first pathogen sequence (Park, et al., 2015).

The method may further comprise determining whether the mutations are deleterious or adaptive. Deleterious mutations are indicative of transmission-impaired viruses and dead-end infections, thus normally only present in an individual subject. Mutations unique to one individual subject are those that occur on the external branches of the phylogenetic tree, whereas internal branch mutations are those present in multiple samples (i.e. in multiple subjects). Higher rate of nonsynonymous substitution is a characteristic of external branches of the phylogenetic tree (Park, et al., 2015).

In internal branches of the phylogenetic tree, selection has had more opportunity to filter out deleterious mutants. Internal branches, by definition, have produced multiple descendent lineages and are thus less likely to include mutations with fitness costs. Thus, lower rate of nonsynonymous substitution is indicative of internal branches (Park, et al., 2015).

Synonymous mutations, which likely have less impact on fitness, occurred at more comparable frequencies on internal and external branches (Park, et al., 2015).

By analyzing the sequenced target sequence, such as viral genomes, it is possible to discover the mechanisms responsible for the severity of the epidemic episode such as during the 2014 Ebola outbreak. For example, Gire et al. made a phylogenetic comparison of the genomes of the 2014 outbreak to all 20 genomes from earlier outbreaks, which suggests that the 2014 West African virus likely spread from central Africa within the past decade. Rooting the phylogeny using divergence from other ebolavirus genomes was problematic (6, 13). However, rooting the tree on the oldest outbreak revealed a strong correlation between sample date and root-to-tip distance, with a substitution rate of $8 \times 10^{-4}$ per site per year (13). This suggests that the lineages of the three most recent outbreaks all diverged from a common ancestor at roughly the same time, around 2004, which supports the hypothesis that each outbreak represents an independent zoonotic event from the same genetically diverse viral population in its natural reservoir. They also found out that the 2014 EBOV outbreak might be caused by a single transmission from the natural reservoir, followed by human-to-human transmission during the outbreak. Their results also suggested that the epidemic episode in Sierra Leone might stem from the introduction of two genetically distinct viruses from Guinea around the same time (Gire, et al., 2014).

It has been also possible to determine how the Lassa virus spread out from its origin point, in particular thanks to human-to-human transmission; and it was even possible to retrace the history of this spread 400 years back (Andersen, et al., Cell 162 (4): 738-50, 2015).

In relation to the work needed during the 2013-2015 EBOV outbreak and the difficulties encountered by the medical staff at the site of the outbreak, and more generally, the method of the invention makes it possible to carry out sequencing using fewer selected probes such that sequencing can be accelerated, thus shortening the time needed from sample taking to results procurement. Further, kits and systems can be designed to be usable on the field so that diagnostics of a patient can be readily performed without need to send or ship samples to another part of the country or the world.

In any method described above, sequencing the target sequence or fragment thereof may use any of the sequencing processes described above. Further, sequencing the target sequence or fragment thereof may be a near-real-time sequencing. Sequencing the target sequence or fragment thereof may be carried out according to previously described methods (Experimental Procedures: Matranga et al., 2014; and Gire, et al., 2014). Sequencing the target sequence or fragment thereof may comprise parallel sequencing of a plurality of target sequences. Sequencing the target sequence or fragment thereof may comprise Illumina sequencing.

Analyzing the target sequence or fragment thereof that hybridizes to one or more of the selected probes may be an identifying analysis, wherein hybridization of a selected probe to the target sequence or a fragment thereof indicates the presence of the target sequence within the sample.

Currently, primary diagnostics are based on the symptoms a patient has. However, various diseases may share identical symptoms so that diagnostics rely much on statistics. For example, malaria triggers flu-like symptoms: headache, fever, shivering, joint pain, vomiting, hemolytic anemia, jaundice, hemoglobin in the urine, retinal damage, and convulsions. These symptoms are also common for septicemia, gastroenteritis, and viral diseases. Amongst the latter, Ebola hemorrhagic fever has the following symptoms: fever, sore throat, muscular pain, headaches, vomiting, diarrhea, rash, decreased function of the liver and kidneys, internal and external hemorrhage.

When a patient is presented to a medical unit, for example in tropical Africa, basic diagnostics will conclude to malaria because statistically, malaria is the most probable disease within that region of Africa. The patient is consequently treated for malaria although the patient might not actually have contracted the disease, and the patient ends up not being correctly treated. This lack of correct treatment can be life-threatening, especially when the disease the patient contracted presents a rapid evolution. It might be too late before the medical staff realizes that the treatment given to the patient is ineffective and comes to the correct diagnostics and administers the adequate treatment to the patient.

The method of the invention provides a solution to this situation. Indeed, because the number of guide RNAs can be dramatically reduced, this makes it possible to provide on a single chip, selected probes divided into groups, each group being specific to one disease, such that a plurality of diseases, e.g. viral infection, can be diagnosed at the same time. Thanks to the invention, more than 3 diseases can be diagnosed on a single chip, preferably more than 4, 5, 6, 7, 8, 9, 10, 11, 12, 13, 14, 15, 16, 17, 18, 19, 20 diseases at the same time, preferably the diseases that most commonly occur within the population of a given geographical area. Since each group of selected probes is specific to one of the diagnosed diseases, a more accurate diagnosis can be performed, thus diminishing the risk of administering the wrong treatment to the patient.

In other cases, a disease such as a viral infection may occur without any symptoms, or has caused symptoms but they faded out before the patient is presented to the medical staff. In such cases, either the patient does not seek any medical assistance or the diagnosis is complicated due to the absence of symptoms on the day of the presentation.

The present invention may also be used in concert with other methods of diagnosing disease, identifying pathogens and optimizing treatment based upon detection of nucleic acids, such as mRNA in crude, non-purified samples.

The method of the invention also provides a powerful tool to address this situation. Indeed, since a plurality of groups of selected guide RNAs, each group being specific to one of the most common diseases that occur within the population of the given area, are comprised within a single diagnostic, the medical staff only need to contact a biological sample taken from the patient with the chip. Reading the chip reveals the diseases the patient has contracted.

In some cases, the patient is presented to the medical staff for diagnostics of particular symptoms. The method of the invention makes it possible not only to identify which disease causes these symptoms but at the same time determine whether the patient suffers from another disease he was not aware of.

This information might be of utmost importance when searching for the mechanisms of an outbreak. Indeed, groups of patients with identical viruses also show temporal patterns suggesting a subject-to-subject transmission link.

Screening Microbial Genetic Perturbations

In certain example embodiments, the CRISPR systems disclosed herein may be used to screen microbial genetic perturbations. Such methods may be useful, for example to map out microbial pathways and functional networks. Microbial cells may be genetically modified and then screened under different experimental conditions. As described above, the embodiments disclosed herein can screen for multiple target molecules in a single sample, or a single target in a single individual discrete volume in a multiplex fashion. Genetically modified microbes may be modified to include a nucleic acid barcode sequence that identifies the particular genetic modification carried by a particular microbial cell or population of microbial cells. A barcode is a short sequence of nucleotides (for example, DNA, RNA, or combinations thereof) that is used as an identifier. A nucleic acid barcode may have a length of 4-100 nucleotides and be either single or double-stranded. Methods for identifying cells with barcodes are known in the art. Accordingly, guide RNAs of the CRISPR effector systems described herein may be used to detect the barcode. Detection of the positive detectable signal indicates the presence of a particular genetic modification in the sample. The methods disclosed herein may be combined with other methods for detecting complimentary genotype or phenotypic readouts indicating the effect of the genetic modification under the experimental conditions tested. Genetic modifications to be screened may include, but are not limited to a gene knock-in, a gene knock-out, inversions, translocations, transpositions, or one or more nucleotide insertions, deletions, substitutions, mutations, or addition of nucleic acids encoding an epitope with a functional consequence such as altering protein stability or detection. In a similar fashion, the methods described herein may be used in synthetic biology application to screen the functionality of specific arrangements of gene regulatory elements and gene expression modules.

In certain example embodiments, the methods may be used to screen hypomorphs. Generation of hypomorphs and their use in identifying key bacterial functional genes and identification of new antibiotic therapeutics as disclosed in PCT/US2016/060730 entitled "Multiplex High-Resolution Detection of Micro-organism Strains, Related Kits, Diagnostic Methods and Screening Assays" filed Nov. 4, 2016, which is incorporated herein by reference.

The different experimental conditions may comprise exposure of the microbial cells to different chemical agents, combinations of chemical agents, different concentrations of chemical agents or combinations of chemical agents, different durations of exposure to chemical agents or combinations of chemical agents, different physical parameters, or both. In certain example embodiments, the chemical agent is an antibiotic or antiviral. Different physical parameters to be screened may include different temperatures, atmospheric pressures, different atmospheric and non-atmospheric gas concentrations, different pH levels, different culture media compositions, or a combination thereof.

Screening Environmental Samples

The methods disclosed herein may also be used to screen environmental samples for contaminants by detecting the presence of target nucleic acid or polypeptides. For example, in some embodiments, the invention provides a method of detecting microbes, comprising: exposing a CRISPR system as described herein to a sample; activating an RNA effector protein via binding of one or more guide RNAs to one or more microbe-specific target RNAs or one or more trigger RNAs such that a detectable positive signal is produced. The positive signal can be detected and is indicative of the presence of one or more microbes in the sample. In some embodiments, the CRISPR system may be on a substrate as described herein, and the substrate may be exposed to the sample. In other embodiments, the same CRISPR system, and/or a different CRISPR system may be applied to multiple discrete locations on the substrate. In further embodiments, the different CRISPR system may detect a different microbe at each location. As described in further detail above, a substrate may be a flexible materials substrate, for example, including, but not limited to, a paper substrate, a fabric substrate, or a flexible polymer-based substrate.

In accordance with the invention, the substrate may be exposed to the sample passively, by temporarily immersing the substrate in a fluid to be sampled, by applying a fluid to be tested to the substrate, or by contacting a surface to be tested with the substrate. Any means of introducing the sample to the substrate may be used as appropriate.

As described herein, a sample for use with the invention may be a biological or environmental sample, such as a food sample (fresh fruits or vegetables, meats), a beverage sample, a paper surface, a fabric surface, a metal surface, a wood surface, a plastic surface, a soil sample, a freshwater sample, a wastewater sample, a saline water sample, exposure to atmospheric air or other gas sample, or a combination thereof. For example, household/commercial/industrial surfaces made of any materials including, but not limited to, metal, wood, plastic, rubber, or the like, may be swabbed and tested for contaminants. Soil samples may be tested for the presence of pathogenic bacteria or parasites, or other microbes, both for environmental purposes and/or for human, animal, or plant disease testing. Water samples such as freshwater samples, wastewater samples, or saline water samples can be evaluated for cleanliness and safety, and/or potability, to detect the presence of, for example, *Cryptosporidium parvum, Giardia lamblia*, or other microbial contamination. In further embodiments, a biological sample may be obtained from a source including, but not limited to, a tissue sample, saliva, blood, plasma, sera, stool, urine, sputum, mucous, lymph, synovial fluid, cerebrospinal fluid, ascites, pleural effusion, seroma, pus, or swab of skin or a mucosal membrane surface. In some particular embodiments, an environmental sample or biological samples may be crude samples and/or the one or more target molecules may not be purified or amplified from the sample prior to application of the method. Identification of microbes may be useful and/or needed for any number of applications, and thus any type of sample from any source deemed appropriate by one of skill in the art may be used in accordance with the invention.

A microbe in accordance with the invention may be a pathogenic microbe or a microbe that results in food or consumable product spoilage. A pathogenic microbe may be pathogenic or otherwise undesirable to humans, animals, or plants. For human or animal purposes, a microbe may cause a disease or result in illness. Animal or veterinary applications of the present invention may identify animals infected with a microbe. For example, the methods and systems of the invention may identify companion animals with pathogens including, but not limited to, kennel cough, rabies virus, and heartworms. In other embodiments, the methods and systems of the invention may be used for parentage testing for breeding purposes. A plant microbe may result in harm or disease to a plant, reduction in yield, or alter traits such as color, taste, consistency, odor. For food or consumable contamination purposes, a microbe may adversely affect the taste, odor, color, consistency or other commercial properties of the food or consumable product. In certain example embodiments, the microbe is a bacterial species. The bacteria may be a psychrotroph, a coliform, a lactic acid bacteria, or a spore-forming bacterium. In certain example embodiments, the bacterium may be any bacterial species that causes disease or illness, or otherwise results in an unwanted product or trait. Bacteria in accordance with the invention may be pathogenic to humans, animals, or plants.

Example Microbes

The embodiment disclosed herein may be used to detect a number of different microbes. The term microbe as used herein includes bacteria, fungi, protozoa, parasites and viruses. In particular embodiments, the microbe is a bacteria. In embodiments, the bacteria is *Borelia* sp. Or *Anaplsam* In some embodiments, the bacterium *Anaplasma phagocytophilum* or other *Anaplasma* species; babesiosis caused by the parasite *Babesia microti* or other *Babesia* species; *Borrelia* infections caused by *Borrelia mayonii, Borrelia miyamotoi, Borrelia burgdorferi* (Lyme disease), or other *Borrelia* species; infections caused by Bourbon virus; Colorado tick fever caused by Coltivirus; Ehrlichiosis caused by the bacterium *Ehrlichia chaffeensis*; Heartland virus infection; Powassan disease caused by Powassan virus; *Rickettsia parkeri* rickettsiosis caused by *Rickettsia parkeri*; Rocky Mountain spotted fever caused by the bacterium *Rickettsia rickettsii*; Southern tick-associated rash illness; tick-borne relapsing fever caused by bacterial *Borrelia hermsii, Borrelia parkeri, Borrelia turicatae*, or *Borrelia hermsii* species; Tularemia caused by the bacterium *Francisella tularensis*; and 364D rickettsiosis caused by *Rickettsia* species.

Bacteria

The following provides an example list of the types of microbes that might be detected using the embodiments disclosed herein. In certain example embodiments, the microbe is a bacterium. Examples of bacteria that can be detected in accordance with the disclosed methods include without limitation any one or more of (or any combination of) *Acinetobacter baumannii, Actinobacillus* sp., Actinomycetes, *Actinomyces* sp. (such as *Actinomyces israelii* and *Actinomyces naeslundii*), *Aeromonas* sp. (such as *Aeromonas hydrophila, Aeromonas veronii* biovar *sobria* (*Aeromonas sobria*), and *Aeromonas caviae*), *Anaplasma phagocytophilum, Anaplasma* marginale *Alcaligenes xylosoxidans, Acinetobacter baumannii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melitensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), Capnocytophaga sp., Cardiobacterium *hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeium* and *Corynebacterium*), *Clostridium* sp. (such as *Clostridium perfringens, Clostridium difficile, Clostridium botulinum* and *Clostridium tetani*), Eikenella corrodens, *Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chaffeensis* and *Ehrlichia canis*), *Epidermophyton floccosum, Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingae, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Mannheimia* kingae, *Microsporum canis, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Pityrosporum orbiculare* (*Malassezia furfur*), *Plesiomonas shigelloides*. Pre-

*votella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella choleraesuis* and *Salmonella typhimurium*), *Serratia* sp. (such as *Serratia marcescens* and *Serratia liquefaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equisimilis*, Group D streptococci, *Streptococcus bovis*, Group F streptococci, and *Streptococcus anginosus* Group G streptococci), *Spirillum minus, Streptobacillus moniliformis, Treponema* sp. (such as *Treponema carateum, Treponema pertenue, Treponema pallidum* and *Treponema endemicum, Trichophyton rubrum, T. mentagrophytes, Tropheryma whipplei, Ureaplasma urealyticum, Veillonella* sp., *Vibrio* sp. (such as *Vibrio cholerae, Vibrio parahaemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metschnikovii, Vibrio damsela* and *Vibrio furnisii*), *Yersinia* sp. (such as *Yersinia enterocolitica, Yersinia pestis*, and *Yersinia pseudotuberculosis*) and *Xanthomonas maltophilia* among others.

Fungi

In certain example embodiments, the microbe is a fungus or a fungal species. Examples of fungi that can be detected in accordance with the disclosed methods include without limitation any one or more of (or any combination of), *Aspergillus, Blastomyces*, Candidiasis, Coccidioidomycosis, *Cryptococcus neoformans, Cryptococcus gattii*, sp. *Histoplasma* sp. (such as *Histoplasma capsulatum*), *Pneumocystis* sp. (such as *Pneumocystis jirovecii*), Stachybotrys (such as *Stachybotrys chartarum*), Mucroymcosis, *Sporothrix*, fungal eye infections ringworm, *Exserohilum, Cladosporium*.

Protozoa

In certain example embodiments, the microbe is a protozoan. Examples of protozoa that can be detected in accordance with the disclosed methods and devices include without limitation any one or more of (or any combination of), Euglenozoa, Heterolobosea, Diplomonadida, Amoebozoa, *Blastocystis*, and Apicomplexa.

Parasites

In certain example embodiments, the microbe is a parasite. Examples of parasites that can be detected in accordance with disclosed methods include without limitation one or more of (or any combination of), an *Onchocerca* species and a *Plasmodium* species.

Viruses

In certain example embodiments, the microbe is a virus. A particular virus that can be detected in accordance with disclosed methods and systems include without limitation one or more of (or any combination of), a flavivirus, including Powassan virus. In embodiments, the NS5 gene of the Powassan virus is detected. In embodiments, Lineage I and/or Lineage II is detected. Detection may also comprise detection of sub-clusters of flaviviruses which can be geographical. In certain instances, geographical sub-clusters of Midwest versus Northeast sub-clustering of lineage II of POWV can be distinguished and detected.

In some embodiments, a method of diagnosing a species-specific bacterial infection in a subject suspected of having a bacterial infection is described as obtaining a sample comprising bacterial ribosomal ribonucleic acid from the subject; contacting the sample with one or more of the probes described, and detecting hybridization between the bacterial ribosomal ribonucleic acid sequence present in the sample and the probe, wherein the detection of hybridization indicates that the subject is infected with one or more bacteria as disclosed herein.

Biomarker Detection

In certain example embodiments, the systems, devices, and methods disclosed herein may be used for biomarker detection. For example, the systems, devices and method disclosed herein may be used for SNP detection and/or genotyping. The systems, devices and methods disclosed herein may be also used for the detection of any disease state or disorder characterized by aberrant gene expression. Aberrant gene expression includes aberration in the gene expressed, location of expression and level of expression. Multiple transcripts or protein markers related to cardiovascular, immune disorders, and cancer among other diseases may be detected. In certain example embodiments, the embodiments disclosed herein may be used for cell free DNA detection of diseases that involve lysis, such as liver fibrosis and restrictive/obstructive lung disease. In certain example embodiments, the embodiments could be utilized for faster and more portable detection for pre-natal testing of cell-free DNA. The embodiments disclosed herein may be used for screening panels of different SNPs associated with, among others, cardiovascular health, lipid/metabolic signatures, ethnicity identification, paternity matching, human ID (e.g. matching suspect to a criminal database of SNP signatures). The embodiments disclosed herein may also be used for cell free DNA detection of mutations related to and released from cancer tumors. The embodiments disclosed herein may also be used for detection of meat quality, for example, by providing rapid detection of different animal sources in a given meat product. Embodiments disclosed herein may also be used for the detection of GMOs or gene editing related to DNA. As described herein elsewhere, closely related genotypes/alleles or biomarkers (e.g. having only a single nucleotide difference in a given target sequence) may be distinguished by introduction of a synthetic mismatch in the gRNA.

In an aspect, the invention relates to a method for detecting target nucleic acids in samples, comprising: distributing a sample or set of samples into one or more individual discrete volumes, the individual discrete volumes comprising a CRISPR system according to the invention as described herein; incubating the sample or set of samples under conditions sufficient to allow binding of the one or more guide RNAs to one or more target molecules; activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules in the sample.

Biomarker Sample Types

The sensitivity of the assays described herein are well suited for detection of target nucleic acids in a wide variety of biological sample types, including sample types in which the target nucleic acid is dilute or for which sample material is limited. Biomarker screening may be carried out on a number of sample types including, but not limited to, saliva, urine, blood, feces, sputum, and cerebrospinal fluid. The embodiments disclosed herein may also be used to detect up- and/or down-regulation of genes. For example, as sample may be serially diluted such that only over-expressed genes remain above the detection limit threshold of the assay.

In certain embodiments, the present invention provides steps of obtaining a sample of biological fluid (e.g., urine, blood plasma or serum, sputum, cerebral spinal fluid), and extracting the DNA. The mutant nucleotide sequence to be detected, may be a fraction of a larger molecule or can be present initially as a discrete molecule.

In certain embodiments, DNA is isolated from plasma/serum of a cancer patient. For comparison, DNA samples isolated from neoplastic tissue and a second sample may be isolated from non-neoplastic tissue from the same patient (control), for example, lymphocytes. The non-neoplastic tissue can be of the same type as the neoplastic tissue or from a different organ source. In certain embodiments, blood samples are collected and plasma immediately separated from the blood cells by centrifugation. Serum may be filtered and stored frozen until DNA extraction.

In certain example embodiments, target nucleic acids are detected directly from a crude or unprocessed sample sample, such as blood, serum, saliva, cerebrospinal fluid, sputum, or urine. In certain example embodiments, the target nucleic acid is cell free DNA.

Cell-Free Chromatin

In certain embodiments, cell free chromatin fragments are isolated and analyzed according to the present invention. Nucleosomes can be detected in the serum of healthy individuals (Stroun et al., Annals of the New York Academy of Sciences 906:161-168 (2000)) as well as individuals afflicted with a disease state. Moreover, the serum concentration of nucleosomes is considerably higher in patients suffering from benign and malignant diseases, such as cancer and autoimmune disease (Holdenrieder et al (2001) Int J Cancer 95, 1 14-120, Trejo-Becerril et al (2003) Int J Cancer 104, 663-668; Kuroi et al 1999 Breast Cancer 6, 361-364; Kuroi et al (2001) Int j Oncology 19, 143-148; Amoura et al (1997) Arth Rheum 40, 2217-2225; Williams et al (2001) J Rheumatol 28, 81-94). Not being bound by a theory, the high concentration of nucleosomes in tumor bearing patients derives from apoptosis, which occurs spontaneously in proliferating tumors. Nucleosomes circulating in the blood contain uniquely modified histones. For example, U.S. Patent Publication No. 2005/0069931 (Mar. 31, 2005) relates to the use of antibodies directed against specific histone N-terminus modifications as diagnostic indicators of disease, employing such histone-specific antibodies to isolate nucleosomes from a blood or serum sample of a patient to facilitate purification and analysis of the accompanying DNA for diagnostic/screening purposes. Accordingly, the present invention may use chromatin bound DNA to detect and monitor, for example, tumor mutations. The identification of the DNA associated with modified histones can serve as diagnostic markers of disease and congenital defects.

Thus, in another embodiment, isolated chromatin fragments are derived from circulating chromatin, preferably circulating mono and oligonucleosomes. Isolated chromatin fragments may be derived from a biological sample. The biological sample may be from a subject or a patient in need thereof. The biological sample may be sera, plasma, lymph, blood, blood fractions, urine, synovial fluid, spinal fluid, saliva, circulating tumor cells or mucous.

Cell-free DNA (cfDNA)

In certain embodiments, the present invention may be used to detect cell free DNA (cfDNA). Cell free DNA in plasma or serum may be used as a non-invasive diagnostic tool. For example, cell free fetal DNA has been studied and optimized for testing on-compatible RhD factors, sex determination for X-linked genetic disorders, testing for single gene disorders, identification of preeclampsia. For example, sequencing the fetal cell fraction of cfDNA in maternal plasma is a reliable approach for detecting copy number changes associated with fetal chromosome aneuploidy. For another example, cfDNA isolated from cancer patients has been used to detect mutations in key genes relevant for treatment decisions.

In certain example embodiments, the present disclosure provides detecting cfDNA directly from a patient sample. In certain other example embodiment, the present disclosure provides enriching cfDNA using the enrichment embodiments disclosed above and prior to detecting the target cfDNA.

Exosomes

In one embodiment, exosomes can be assayed with the present invention. Exosomes are small extracellular vesicles that have been shown to contain RNA. Isolation of exosomes by ultracentrifugation, filtration, chemical precipitation, size exclusion chromatography, and microfluidics are known in the art. In one embodiment exosomes are purified using an exosome biomarker. Isolation and purification of exosomes from biological samples may be performed by any known methods (see e.g., WO2016172598A1).

SNP Detection and Genotyping

In certain embodiments, the present invention may be used to detect the presence of single nucleotide polymorphisms (SNP) in a biological sample. The SNPs may be related to maternity testing (e.g., sex determination, fetal defects). They may be related to a criminal investigation. In one embodiment, a suspect in a criminal investigation may be identified by the present invention. Not being bound by a theory nucleic acid based forensic evidence may require the most sensitive assay available to detect a suspect or victim's genetic material because the samples tested may be limiting.

In other embodiments, SNPs associated with a disease are encompassed by the present invention. SNPs associated with diseases are well known in the art and one skilled in the art can apply the methods of the present invention to design suitable guide RNAs (see e.g., ncbi.nlm.nih.gov/clinvar?term=human%5Borgn%5D).

In an aspect, the invention relates to a method for genotyping, such as SNP genotyping, comprising:

distributing a sample or set of samples into one or more individual discrete volumes, the individual discrete volumes comprising a CRISPR system according to the invention as described herein;

incubating the sample or set of samples under conditions sufficient to allow binding of the one or more guide RNAs to one or more target molecules;

activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules characteristic for a particular genotype in the sample.

In certain embodiments, the detectable signal is compared to (e.g. by comparison of signal intensity) one or more standard signal, preferably a synthetic standard signal. In certain embodiments, the standard is or corresponds to a particular genotype. In certain embodiments, the standard comprises a particular SNP or other (single) nucleotide variation. In certain embodiments, the standard is a (PCR-amplified) genotype standard. In certain embodiments, the standard is or comprises DNA. In certain embodiments, the standard is or comprises RNA. In certain embodiments, the standard is or comprised RNA which is transcribed from DNA. In certain embodiments, the standard is or comprises DNA which is reverse transcribed from RNA. In certain embodiments, the detectable signal is compared to one or more standard, each of which corresponds to a known genotype, such as a SNP or other (single) nucleotide variation. In certain embodiments, the detectable signal is compared to one or more standard signal and the comparison comprises statistical analysis, such as by parametric or non-parametric statistical analysis, such as by one- or two-way ANOVA, etc. In certain embodiments, the detectable signal is compared to one or more standard signal and when the detectable signal does not (statistically) significantly deviate from the standard, the genotype is determined as the genotype corresponding to said standard.

In other embodiments, the present invention allows rapid genotyping for emergency pharmacogenomics. In one embodiment, a single point of care assay may be used to genotype a patient brought into the emergency room. The patient may be suspected of having a blood clot and an emergency physician needs to decide a dosage of blood thinner to administer. In exemplary embodiments, the present invention may provide guidance for administration of blood thinners during myocardial infarction or stroke treatment based on genotyping of markers such as VKORC1, CYP2C9, and CYP2C19. In one embodiment, the blood thinner is the anticoagulant warfarin (Holford, NH (December 1986). "Clinical Pharmacokinetics and Pharmacodynamics of Warfarin Understanding the Dose-Effect Relationship". Clinical Pharmacokinetics. Springer International Publishing. 11 (6): 483-504). Genes associated with blood clotting are known in the art (see e.g., US20060166239A1;

Litin S C, Gastineau D A (1995) "Current concepts in anticoagulant therapy". Mayo Clin. Proc. 70 (3): 266-72; and Rusdiana et al., Responsiveness to low-dose warfarin associated with genetic variants of VKORC1, CYP2C9, CYP2C19, and CYP4F2 in an Indonesian population. Eur J Clin Pharmacol. 2013 March; 69 (3): 395-405). Specifically, in the VKORC1 1639 (or 3673) single-nucleotide polymorphism, the common ("wild-type") G allele is replaced by the A allele. People with an A allele (or the "A haplotype") produce less VKORC1 than do those with the G allele (or the "non-A haplotype"). The prevalence of these variants also varies by race, with 37% of Caucasians and 14% of Africans carrying the A allele. The end result is a decreased number of clotting factors and therefore, a decreased ability to clot.

In certain example embodiments, the availability of genetic material for detecting a SNP in a patient allows for detecting SNPs without amplification of a DNA or RNA sample. In the case of genotyping, the biological sample tested is easily obtained. In certain example embodiments, the incubation time of the present invention may be shortened. The assay may be performed in a period of time required for an enzymatic reaction to occur. One skilled in the art can perform biochemical reactions in 5 minutes (e.g., 5 minute ligation). The present invention may use an automated DNA extraction device to obtain DNA from blood. The DNA can then be added to a reaction that generates a target molecule for the effector protein. Immediately upon generating the target molecule the masking agent can be cut and a signal detected. In exemplary embodiments, the present invention allows a POC rapid diagnostic for determining a genotype before administering a drug (e.g., blood thinner). In the case where an amplification step is used, all of the reactions occur in the same reaction in a one step process. In preferred embodiments, the POC assay may be performed in less than an hour, preferably 10 minutes, 20 minutes, 30 minutes, 40 minutes, or 50 minutes.

EXAMPLES

Example 1—Research Strategy and Initial Analysis of *B. microti*

There are over a dozen tick-borne pathogens in the United States, at least five of which have been recognized over the past decade. Infections are characterized by clinical heterogeneity that is poorly understood and contributes to a sense of mystery and fear surrounding Lyme and other tick-borne diseases (TBDs). Using a large cohort of TBD cases (over 250 at present), the complete genomes have been sequenced of over 300 combined cases of Lyme and babesiosis, with the goal of developing SHERLOCK diagnostics. Variants associated with relapsing babesiosis have been identified which resemble known mutations in the targets of atovaquone and azithromycin that cause resistance in other species, suggesting a probable basis of clinical relapse. In particular, Applicants have identified variants associated with relapsing babesiosis in cytochrome B (cytB) and ribosome protein subunit L4 (rpl4). A genome-wide scan for proteins with increased non-synonymous rates of substitution in relapsing cases compared to controls which identified five amino acid substitutions in cytB (FIG. 1A) and three amino acid substitutions in rpl4 (FIG. 1B) that occur only in relapsing cases. Structural modeling of these variants in orthologs of cytB and rpl4 demonstrated that these substitutions occur in regions adjacent to the binding site of atovaquone (FIG. 1C) and azithromycin (FIG. 1D). Also identified is the three-fold amplification of an approximately 15 kilobase locus containing a putative drug efflux pump in a single case of relapse with prolonged survival under drug pressure (FIG. 1E). Without being bound by theory, it is believed that these variants reduce the susceptibility to anti-babesial drugs by altering target binding (cytB and rpl4) or promoting drug efflux (BBM_II01855).

It is believed variants cause drug resistance and relapse-associated variants may be transmitted to humans from ticks or arise de novo in patients. *B. microti* putative drug-resistance alleles may evolve during treatment of human infections while being rare or absent in nature, which will also be tested using SHERLOCK.

Development of Detection

It is unclear whether relapse-associated variants circulate in ticks or arise de novo during treatment of human infection. If these variants are present in ticks, then many more patients could be at risk, particularly as *B. microti* genotypes are expanding at different rates in the population. It is possible relapse-associated variants evolve during treatment and are extremely rare in nature. Accordingly, use of sensitive, low-cost, culture-independent methods of detecting disease-associated variants and applying them to screen ticks and monitor allelic dynamics during human infections is needed. Such tools will be invaluable for understanding tick-borne pathogens which circulate in complex, enzootic cycles which are interconnected with human activities and the environment.

*B. microti* genome sequencing created a target capture method which produces 50-100-fold enrichment of target sequences (FIG. 2A). This approach is limited by high cost (approximately $300-500 per sample) and is therefore impractical for large entomological surveys or longitudinal analysis in multiple patients. Use of Illumina iSeq, is ideal for small genomes such as those of TBD pathogens (FIG. 2B). Additionally, as described herein new low-cost, sequence-specific diagnostic SHERLOCK (Specific High sensitivity Enzymatic Reporter unLOCKing) has been developed and is a sensitive and robust method to detect pathogens. Initial SHERLOCK assays developed for *B. microti* that differentiate between wild-type alleles and a putative atovaquone-resistance SNP (FIGS. 2c-d). These assays can be reprogrammed by altering amplification primers and determining optimal guide RNA to detect additional variants or other TBDs (FIG. 2e) and described in these examples creating flexible tools for surveillance of multiple TBD and individual variants. Novel diagnostics with variant specificity: Building off the successful development of a variant-specific SHERLOCK for *B. microti* (FIGS. 2c-d), SNP-specific assays to detect all relapse-associated variants will be developed. Development of these assays will proceed in a similar fashion to the initial *B. microti* SHERLOCK: creating and testing candidate recombinase polymerase amplification (RPA) primer or other amplification primer sets, and selection of multiple CRISPR RNA guides. Since the collateral cleavage of Cas13 has a sequence specificity of 2 base mismatches in the guide RNA, these RNAs can be synthesized with a known mismatch, such that when a variant is encountered, activity is lost. Multiple variants may be multiplexed by leveraging the recent discovery of multiple Cas13 orthologs, including Cas13b, Cas13c, and Cas13d.

Variant-specific assays will be applied to a collection of ticks collected from local sites. If relapse-associated variants are identified, this would suggest that these variants circulate in enzootic cycles in nature. The fraction of ticks in which such variants are identified will provide an estimate of their frequency in nature. Further analysis of patient samples will be conducted as described in later examples herein, and can include samples before, during, and after treatment with antiparasitic drugs. The SHERLOCK assays may be used to sample each time point for the resistance allele. SHER-LOCK will provide a very sensitive binary measurement that determines the presence or absence of target DNA (FIG. 2c-e). Samples for this work will be available under the Partners Institutional Review Board (IRB) protocol 2014P000948, which currently includes longitudinal samples from over 60 individuals with babesiosis, including three with relapsing babesiosis.

Example 2—Sensitive Diagnostics to Guide Treatment of TBD

Diagnosis of TBD is challenging as the syndromes associated with these illnesses are quite variable. As a result, patients are frequently misdiagnosed or treated with unnecessarily broad empiric antimicrobial therapy. There is a critical need for rapid, sensitive, sequence-specific, point-of-care (POC) diagnostics to guide treatment of TBD. Here, Applicants propose (1) to develop rapid POC diagnostic tests using SHERLOCK (specific, high-sensitivity, molecular unlocking) for the most common TBDs in the region and (2) to evaluate their performance on a well-phenotyped clinical cohort. The assays developed will greatly improve the detection TBD and thereby improve the care of patients with these illnesses.

Figure 11:
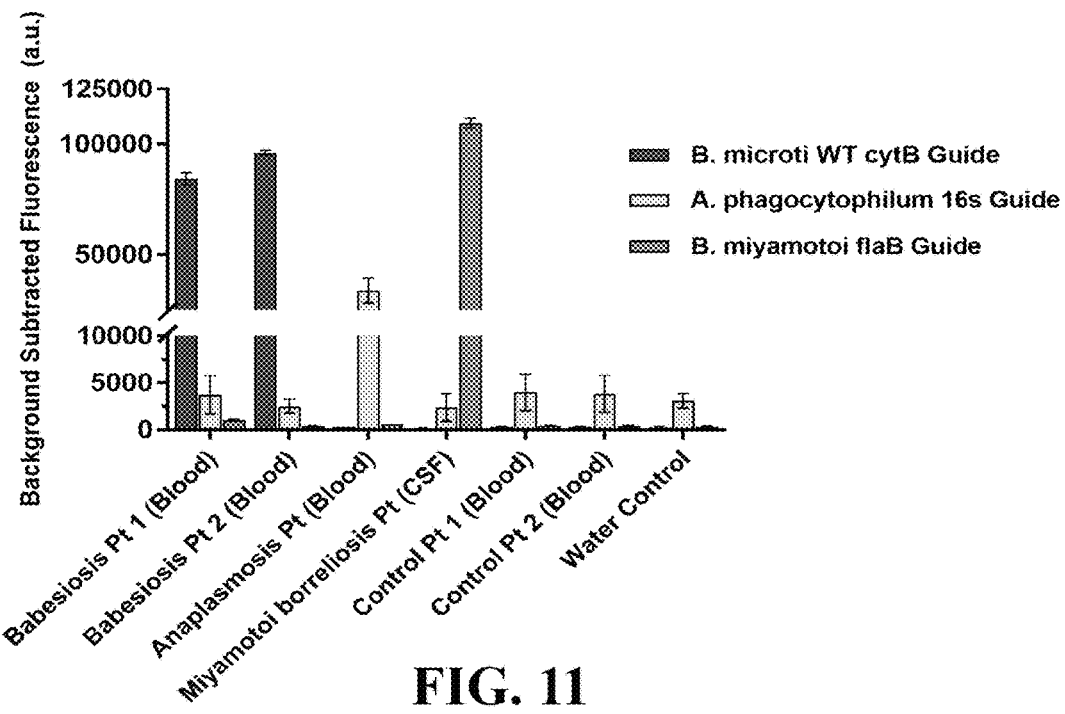
FIG. 11—Results of validating assays on clinical samples, DNA extract of patient samples with confirmed diagnosis by diagnostic standard.

Develop specific high-sensitivity enzymatic reporter unlocking (SHERLOCK) assays is shown, see, e.g. FIG. 11, for POC detection of *Borrelia* spp., *Babesia microti*, and *Anaplasma phagocytophilum*. In addition to pathogen detection, these assays will be developed to identify subspecies, lineage, and clinically relevant (drug resistance) variants.

Validation of TBD-SHERLOCK assays in a preliminary cohort of patients with Lyme and other *Borrelia* spp. (e.g. *miyamotoi, mayonii*) (n=10), babesiosis (n=10), anaplasmosis (n=10) and TBD negative controls (n=10) to establish the clinical performance (sensitivity and specificity) of these assays.

First, the Applicants designed assays using synthetic template genomic DNA ("g-blocks"). The analytical sensitivity of each assay using serial dilutions, and define cross-reactivity by measuring assay performance on control DNA including human DNA and other TBD pathogens. Refinement and validation of the assays using a cohort of n=10 *B. burgdorferi*, n=10 *B. microti*, and n=10 *A. phagocytophilum* samples collected, will be the next step.

Figures 3A, 3B, 3C, 3D, 4A, 4B, 4C, 4D:
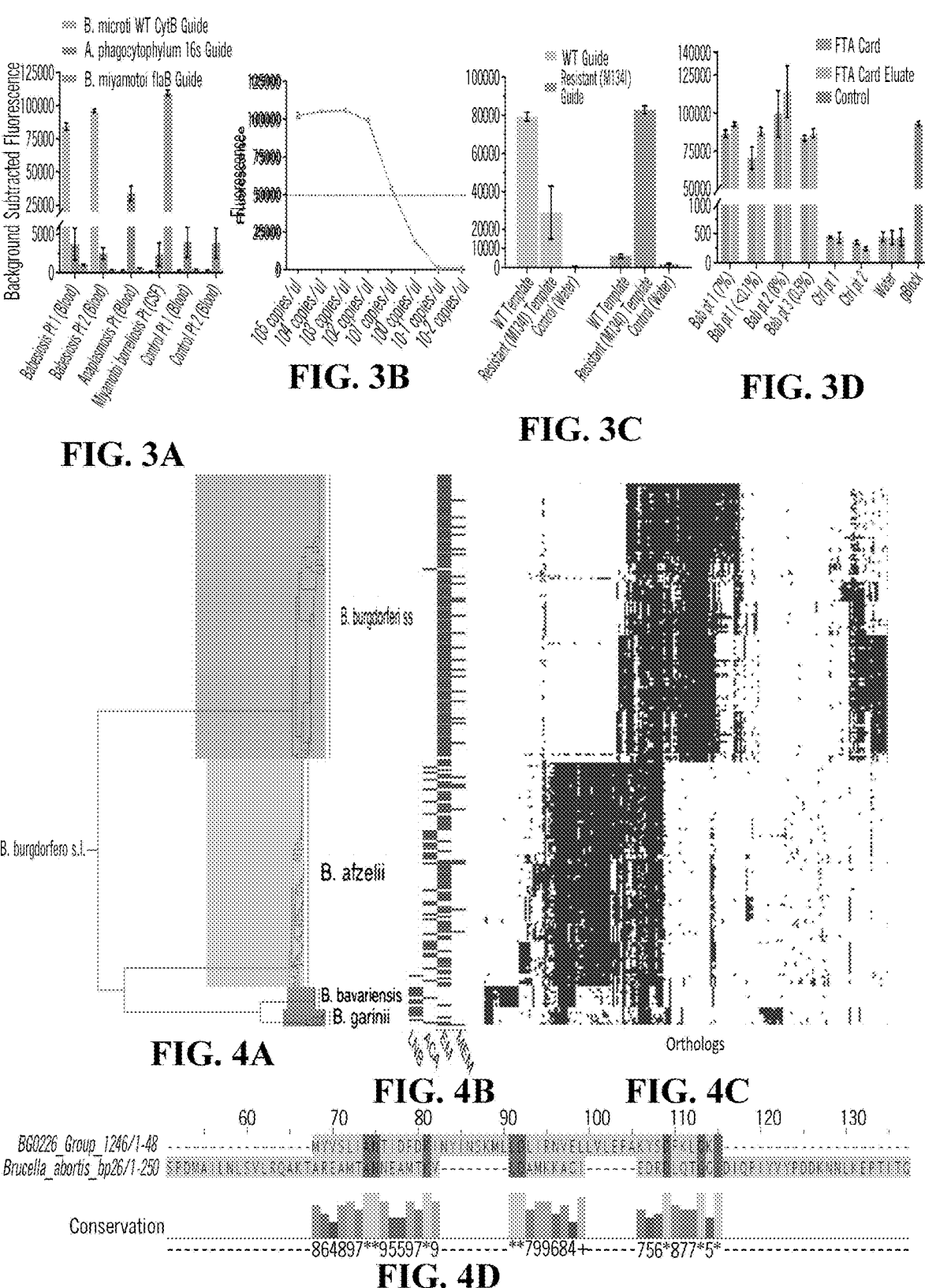
FIG. 3A-3D—(3A) SHERLOCK assays for babesiosis (B. microti), anaplasmosis (A. phagocytophilum), and neuroborreliosis (B. miyamotoi) successfully detect pathogens from clinical specimens. (3B) B. microti SHERLOCK assays are highly sensitive with a detection limit in the 1-10 copies per uL range. (3C) SHERLOCK assays can detect clinically relevant mutations, including a drug-resistance variant in B. microti. (3D) POC nucleic acid extraction on Whatman FTA cards can be used as input for SHERLOCK.
FIGS. 4A-4D-Core chromosomal phylogeny of B. burgdorferi s.l. strains 4(B) Clinical phenotype of each strain (LNB—Lyme neuroborreliosis; ACA acrodermatitis chronica atrophicans; EM—erythema migrans; MEM— multiple EM). (4C) Matrix of orthologs (Columns) by strains (Rows) A blue dot signifies that the ortholog is present in a given strain. As in 4B, the ordering of rows corresponds to the phylogeny in 4A, (4D) Alignment of Group_1246, SIMPL-containing protein (SEQ ID NO: 4), with Brucella abortus bp26 (SEQ ID NO: 5), showing conserved domains.

As provided herein, Applicants designed preliminary SHERLOCK assays for *B. microti, A. phagocytophilum*, and *B. miyamotoi*. These show highly promising detection properties including pathogen-specific detection (FIG. 3a), high sensitivity (FIG. 3b), and single-nucleotide specificity (FIG. 3c). DNA extraction can be omitted by placing analyte on a Whatman FTA card (FIG. 3d). The next step is to extend and adapt these assays to create POC tests. To do so, Applicants will first design additional assays to include the two known species of Lyme disease in the United States (*B. burgdorferi* and *B. mayonii*) and which distinguish between US and European strains of Lyme (*B. burgdurferi* sensu lato). These will be transferred from a fluorescence reader to paper and optimize extraction free detection methods (FIG. 8) using the HUDSON protocol, which the Sabeti lab has developed for viral detection, to create a POC diagnostic.

Description of the cohort/patient group: Applicants will recruit 10 patients with Lyme and other *Borrelia* infections, 10 patients with babesiosis, 10 patients with anaplasmosis, and 10 TBD-negative controls with TBD-like illness during tick season. Recruitment will be split over two seasons, and Applicants will recruit at least 20 patients per year.

Description of the proposed laboratory investigation: Applicants will apply TBD SHERLOCK assays at "bedside" (immediately after obtaining sample, but in the clinical microbiology laboratory and separated from the clinical workflow). Applicants will calculate the sensitivity and specificity by comparing cases to controls for each illness. As a "gold-standard", Applicants will use CDC criteria for Lyme disease (i.e. clinical criteria plus the result of two-tier serological testing, depending on stage), PCR for *B. miyamotoi, B. microti* and *A. phagocytophilum*.

Discussion of the collaboration and value added by this effort: Creating a diagnostic that meets the required design criteria along with the needs of patients and providers requires a multidisciplinary approach and team.

Demonstration of feasibility or preliminary results: Applicants previously successfully enrolled over 50 cases of babesiosis over a three-year period. Based on our track record of recruitment, along with the preliminary success of SHERLOCK diagnostics and extraction-free sample preparation techniques. Applicants believe it is feasible to enroll the proposed numbers of cases and apply SHERLOCK assays in a POC setting.

Example 3: *B. burgdorferi* and Synovial Fluid

Development of methods to enrich spirochetal DNA from synovial fluid: I will first establish the analytical sensitivity of the target capture technique by spiking *B. burgdorferi* s.s. DNA into uninfected synovial fluid across a range of concentrations. I will use quantitative PCR to measure the absolute concentration of *B. burgdorferi* s.s. in these samples. I will also measure *B. burgdorferi* s.s. DNA concentrations in patient synovial fluid samples. If the sensitivity of *B. burgdorferi* s.s. target capture is sufficient to recover DNA from synovial fluid in cases of Lyme arthritis, I will then apply target capture and sequencing to a pilot set of samples comprising 10 synovial fluid samples from Lyme arthritis, 10 negative control samples of normal synovial fluid, and 10 positive control samples spiked with different concentrations of *B. burgdorferi* s.s. DNA. This technology will enable genomic association studies of Lyme arthritis. The Sabeti lab's background and experience with hybrid capture for a variety of microbes and sample types will be an important determinant of success for this work. However, if Applicants encounter challenges with this approach, alternate approaches, discussed below, will enable association studies of *B. burgdorferi* genes in Lyme arthritis.

Sub-classification of Lyme arthritis cases: Lyme arthritis is a complex condition with both infectious and autoimmune components.[51,95] There are antibiotic-responsive and antibiotic-refractory cases, as well as subsets of each. To characterize the precise clinical phenotype of Lyme arthritis cases, I will review case records of a cohort of 124 cases of Lyme arthritis for which synovial fluid is available.

Pan-genome and genome-wide association studies of Lyme arthritis: After developing protocols for target capture of *B. burgdorferi* s.s. genomic material in synovial fluid and characterizing clinical cases, Applicants will sequence the genomic material from a cohort of 124 samples of synovial fluid samples. Based on a power analysis (described below), this cohort will be sufficient to identify alleles that cause Lyme arthritis using a matched-pair study design that can be used in the SHERLOCK diagnostic.

It is believed microbial genetic factors that allow spirochetes to invade through host endothelium and adhere to neural or synovial tissues promote neuroborreliosis and Lyme arthritis, identification of which can be used in the SHERLOCK diagnostics.

Preliminary data: The list of phenotype-associated genes (Tables 7 and 8) contains some well-understood genes such as CRASP1 (CspA)[104], but the majority are unannotated. I manually reviewed the BLAST results of this list to identify genes of particular interest for further analysis. The notable genes include Group_1246, which corresponds to BG0226, an unannotated gene which is present in *B. bavariensis* and *B. garinii* but for which a close homolog is absent in other Lyme disease-causing genospecies. A primary homology search identifies a signaling molecule that interacts with the mouse pelle-like kinase (SIMPL) domain. Such domains are present in other *B. burgdorferi* s.l. proteins as well as both bacteria and higher eukaryotes. In *Brucella abortus*, the related, immunogenic BP26 protein contains a SIMPL domain; crystallography shows that these monomers collectively form into a 16-mer, which creates a novel pore structure that may play a role in infection. BG0226/Group_1246 has homology to the alpha-1 alpha helix region of the BP26 protein (FIG. 4D), suggesting that it may form multimers or a protein complex with other SIMPL-domain containing *B. burgdorferi* s.l. proteins. The initial characterization is focused on BG0226.

During the independent phase of this grant, candidate will be tested for in vitro function, and 2-3 in the mouse model, which may include genes identified in this example, including Tables 7 and 8. Potential candidates include: Group_231, a member of the important MLP-lipoprotein family with a unique isoform in *B. bavariensis*; Group_543, a protein with homology to virulence-associated lipoproteins; Group_1501 (BGP290), which has no annotated function but which shares homology to DNA helicases; and Group_1251, a putative outer surface lipoprotein. After learning the methods of *Borrelia* genetics, molecular biology, and the *B. burgdorferi* mouse model, studies will be expanded to allow for further, directed characterization of 3-5 additional genes associated with neuroborreliosis or acrodermatitis or human infection and arthritis.

These experiments will determine whether BG0226 facilitates binds to neuronal tissues and leads to increased virulence and/or meningeal binding in the mouse model. The existing dataset consists of 249 strains, a sample size that has been sufficiently powerful to identify genes significantly associated with neuroborreliosis and acrodermatitis (Tables 7 and 8) using pan-genome association studies. For microbial genome-wide association studies that focus on variants rather than whole genes, the existing dataset is similar in size to published studies. Microbial genome-wide association studies typically require smaller sample sizes than comparable human genetic studies, due to smaller genome sizes and fewer genes.

Preliminary data: In collaboration with Drs. Klemen Strle, Franc Strle, and Allen Steere, Dr. Sabeti and 249 *B. burgdorferi* s.l. genomes were sequenced using next-generation sequencing with Illumina instruments. Applicants then de novo assembled the genomes, annotated the draft assemblies, and identified orthologs present in each of the strains.[71] FIG. 4A-4C shows the resulting phylogeny (FIG. 4a), clinical phenotype (FIG. 4b), and accessory genome elements (FIG. 4c). Consistent with prior reports, *B. afzelii* is strongly associated with acrodermatitis chronica atrophicans (ACA) (chi-square test, p=3.3e-10), and the *B. garinii*/*B. Bavariensis* group is associated with Lyme neuroborreliosis (LNB) (chi-square test, p<2.2e-16), supporting a heritable bacterial genetic cause for neuroborreliosis and acrodermatitis. Applicants then conducted microbial pan-genome association studies, correlating the clinical phenotype with the presence or absence of individual accessory genome elements. Table 7 and Table 8 show the top 10 most strongly associated genes for two key phenotypes, neuroborreliosis and acrodermatitis chronica atrophicans. Nearly all of the genes associated with these phenotypes lie outside the core-genome of approximately 1250 proteins[73] that shows stability across strains and genospecies of *B. burgdorferi* s.l. The resulting set of phenotype-associated genes provides candidate loci for further characterization and for SHERLOCK diagnostics according to methods and approaches described further herein.

TABLE 7

| Ortholog Group | P Value | Odd ratio | Annotation |
|---|---|---|---|
| group_1246 | 4.33E−17 | 897.85 | Hypothetical protein (Chromosome) |
| group_231 | 4.33E−17 | 897.85 | Lipoporotein (plasmid) |
| group_543 | 1.19E−16 | 772.78 | Antigen P35 (Plasmid) |
| group_1474 | 8.17E−16 | 399.41 | Hypothetical protein (plasmid) |
| group_1501 | 8.17E−16 | 399.41 | Replicative DNA helicase (Plasmid) |
| group_1167 | 7.60E−15 | 273.14 | Hypothetical protein BB_0102 (chromosome) |
| group_1249 | 7.60E−15 | 273.14 | CRASP 1 (Plasmid) |
| group_1251 | 7.60E−15 | 273.14 | Outer surface protein (plasmid) |

TABLE 8

| Ortholog Group | P Value | Odd ratio | Annotation |
|---|---|---|---|
| group_287 | 1.75E−13 | 35.87 | Hypothetical protein (plasmid) |
| group_280 | 2.59E−13 | 34.81 | Lipoporotein (plasmid) |
| group_102 | 5.60E−13 | 33.45 | Virulence associated lipoprotein (plasmid) |
| yhjE | 2.02E−12 | 35.87 | Lipoporotein (plasmid) |
| group_1594 | 2.46E−12 | 23.57 | Hypothetical protein BB_0242 (Chromosome) |
| group_205 | 2.46E−12 | 23.57 | Outer membrane protein (plasmid) |
| group_298 | 2.47E−12 | 30.88 | hypothetical protein (plasmid) |
| group_700 | 2.47E−12 | 30.88 | membrane protein (plasmid) |

TABLE 9

| Ortholog Group | P Value | Odd ratio | Annotation |
|---|---|---|---|
| group_2454 | 5.28E−23 | 2321.57 | Antigen, P35 (lp56 plasmid) |
| group_41 | 5.28E−23 | 2321.57 | Hypothetical lipoprotein (lp56 plasmid) |
| group_2450 | 1.58E−21 | 765.09 | Hypothetical protein (chromosome) |
| group_532 | 2.34E−20 | 450.34 | Adenine specific DNA methyltransferase (lp56 plasmid) |
| group_1515 | 5.11E−20 | 441.42 | Outer surface protein C (cp26 plasmid) |
| group_1516 | 2.38E−19 | 317.35 | hypothetical protein (lp36 plasmid) |
| group_8670 | 2.38E−19 | 317.35 | Hypothetical protein (lp28-1 plasmid) |
| group_1261 | 6.66E−17 | 162.39 | PF-32 protein (lp56 plasmid) |
| group_2453 | 6.66E−17 | 162.39 | Hypothetical protein BB_Q09 (lp56 plasmid) |
| group_8667 | 1.20E−16 | 441.42 | Hypothetical protein BB_H26 (lp56 plasmid) |

Example 4—CRISPR Guide Design

CRISPR-RNA Guide Design: Applicants chose preferred sites based on prior knowledge of drug-resistance variants, copy number, and other genetic conservation for each of the assays as noted below. Spacer sequences (crRNAs) for SHERLOCK detection of tick-borne diseases are designed based on insights from research generated by our group, as well as known or suspected clinically relevant variants.

Figures 6A, 6B, 6C:
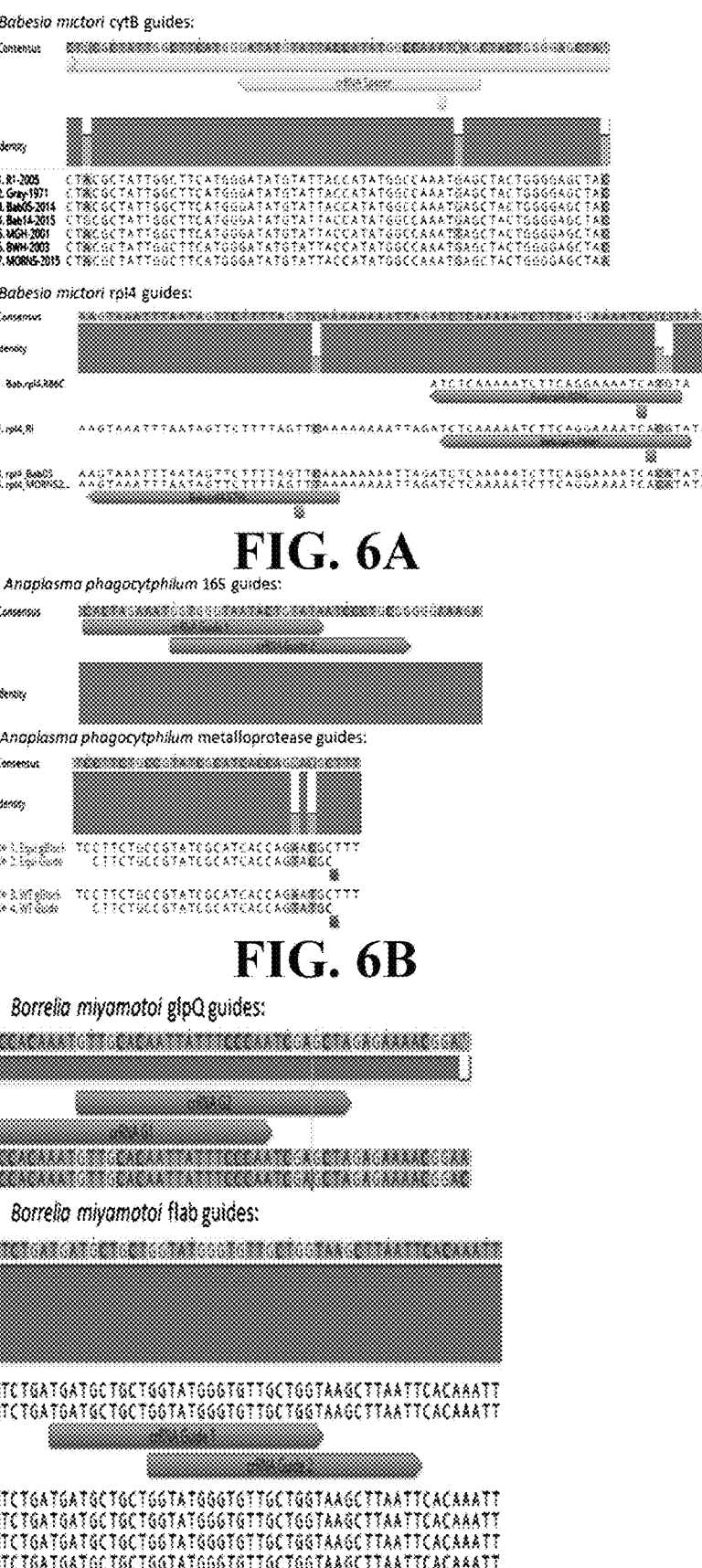
FIGS. 6A-6C-depiction of guide sequences (6A) B. microti SEQ ID NOS: 6-13 and 15-19; (6B) A. phagocytophilum SEQ ID NOS: 20-25; and (6C) B. miyamotoi SEQ ID NOS: 26-29.

*Babesia microti: Babesia microti* guides make use the increased copy number of mitochondrial and apicomplexan sequences relative to chromosomal targets (FIG. 1). For detection, Applicants focus on the mitochondrial sequences that are present in roughly 20-fold excess. The relative abundance of *B. microti* sequences are known from our existing database of whole genome sequences (Lemieux et al., 2016). *B. microti* crRNA guides are designed to detect the single nucleotide polymorphism associated with a methionine to isoleucine substitution in the cytochrome B complex associated with atovaquone resistance and clinical relapsing disease (Lemieux et al., 2016; FIG. 6A). Sequences generated by our group discovered this novel mutation in *B. microti*, as well as other relevant SNPs and variants associated with first-line drug therapy resistance, including azithromycin resistance inherited through mutations in the ribosomal protein subunit L4 (FIG. 7). Our crRNA guides designed to detect clinically relevant variants show strong discrimination and highly sensitive detection.

*Anaplasma phagocytophilum: Anaplasma phagocytohilum* crRNA guides are designed to detect a SNP along the coding region for metalloprotease APH_RS04870, associated with variation in infectivity in humans versus equine species (FIG. 6B). Further guides are designed for sensitive detection of *A. phagocytophilum* using suspected highly conserved segments of the pathogen genome, including in the coding region for the 16S ribosomal RNA.

*Borrelia miyamotoi: Borrelia miyamotoi* crRNA guides are designed for highly sensitive detection along highly preserved regions of the genome, including along the coding regions of the glycerophosphodiester phosphodiesterase gene (glpQ) and flagellin B gene (flaB; FIG. 6C).

Example 6—Paper-Based Nucleic Acid Extraction for SHERLOCK Input

Figure 8A:
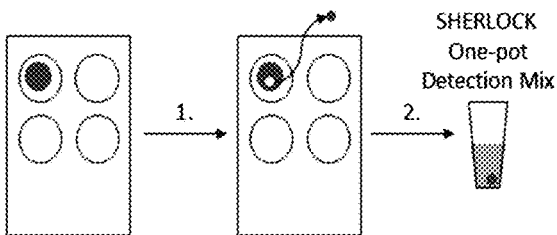
FIG. 8A—Nucleic acid extracted on filter paper (Whatman FTA cards, GE Healthcare) as input to SHERLOCK. Clinical specimen is spotted on paper and allowed to dry, then (1) a 1.2 mm punch is removed from the spotted area. The punch is then (2) input directly into the RPA/Cas13a fluorescent detection mastermix, creating a single-pot nucleic acid extraction and SHERLOCK detection mix.
Figure 8B:
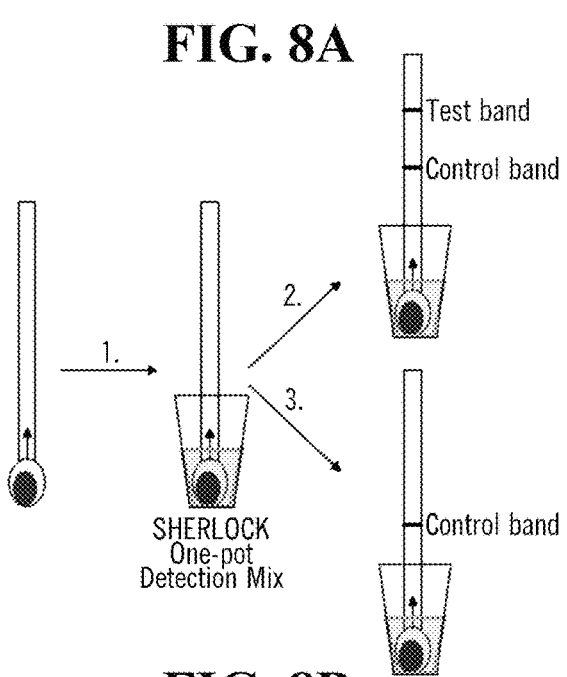
FIG. 8B Filter paper is stacked on a lateral flow detection strip (TwistDX) to create an all-on-paper detection strategy. Clinical specimen is spotted onto the filter paper and the combined specimen-detection strip is then (1) inserted into the SHERLOCK single-pot reaction mix. Visual band read out determines the sample to be either (2) positive or (3) negative.
Figure 9:
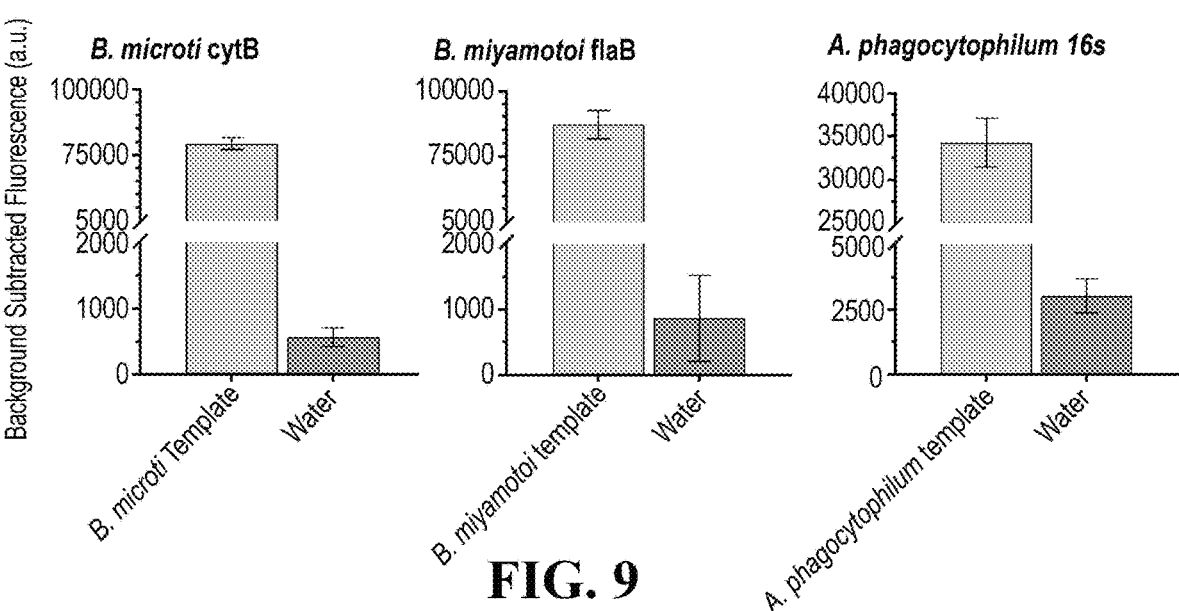
FIG. 9—SHERLOCK Detection of B. *Microti* cytB (left) *B. miyamotoi* flaB (middle) and *A. phagocytophilum* 16s (right) with background subtracted fluorescence measured.
Figure 10:
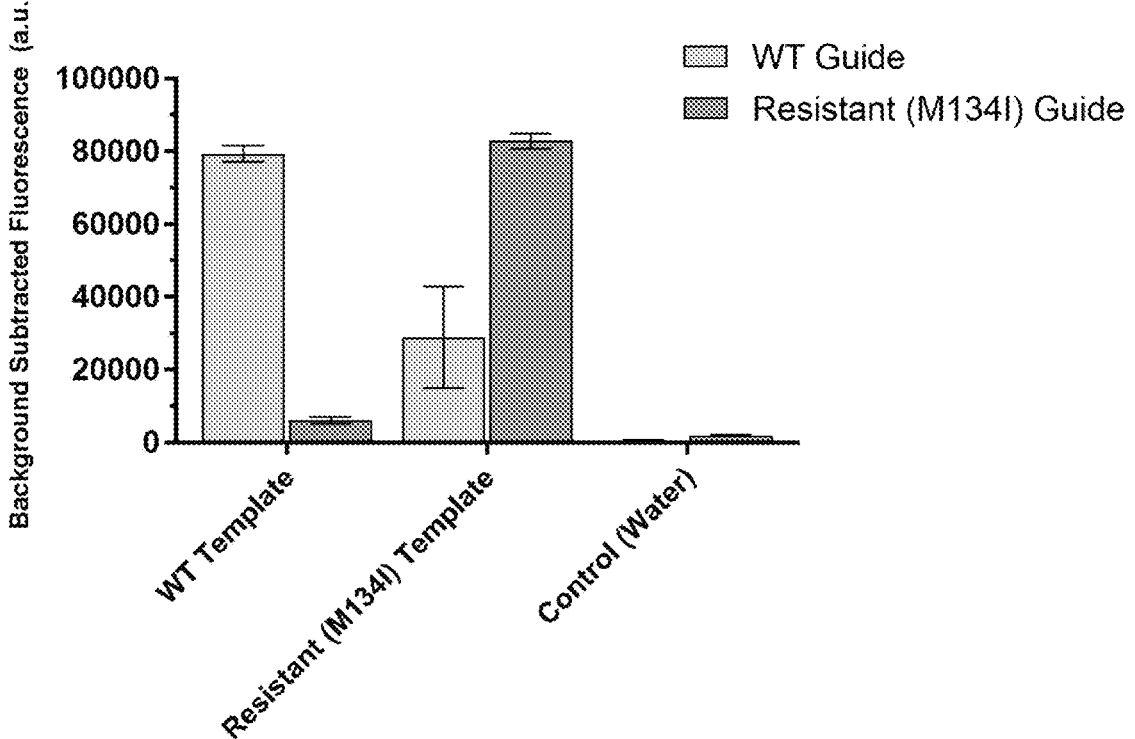
FIG. 10 *B. microti*: cytB M134I SNP Detection of synthetic template using SHERLOCK methods disclosed herein.
Figure 12:
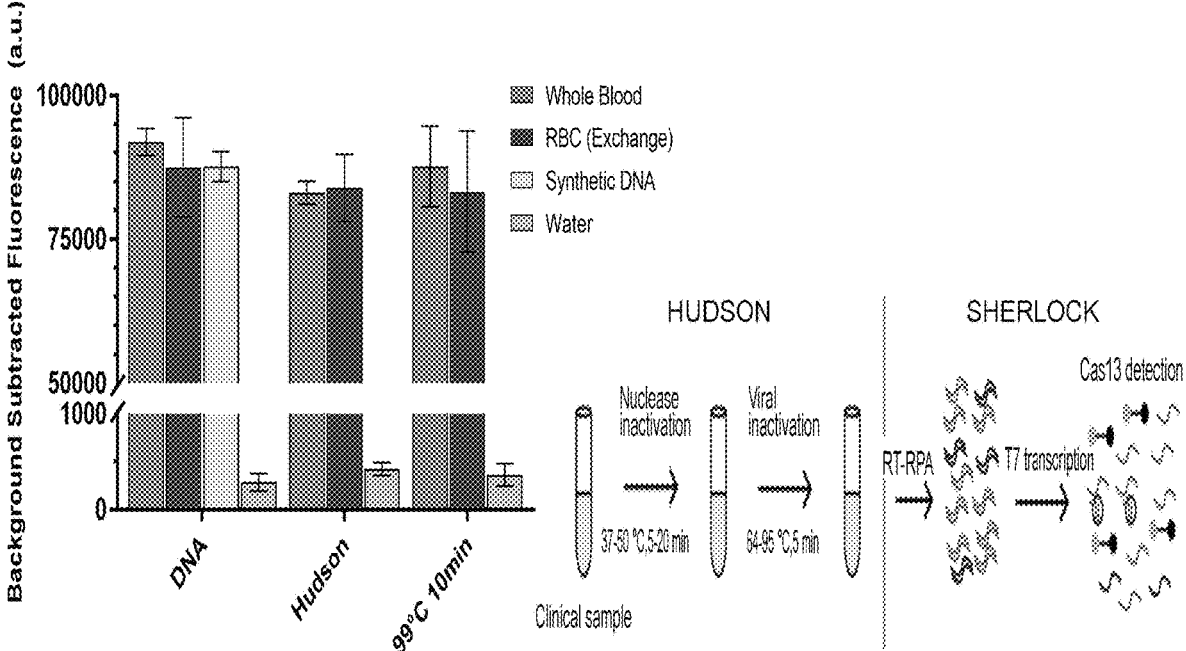
FIG. 12—Includes results and schematic of *B. microti* HUDSON and Heat Treatment. HUDSON Methods: Myhrvold, et al., (2018). Field-deployable viral diagnostics using CRISPR-Cas13. Science, 360 (6387), 444-448. doi: 10.1126/science.aas8836. Blood from bab patient was explored to determine whether detection from blood without obliterating nucleases would be sufficient for bab infections based on previous publication using raw heat treatment for malaria samples input into LAMP detection.
Figure 15:
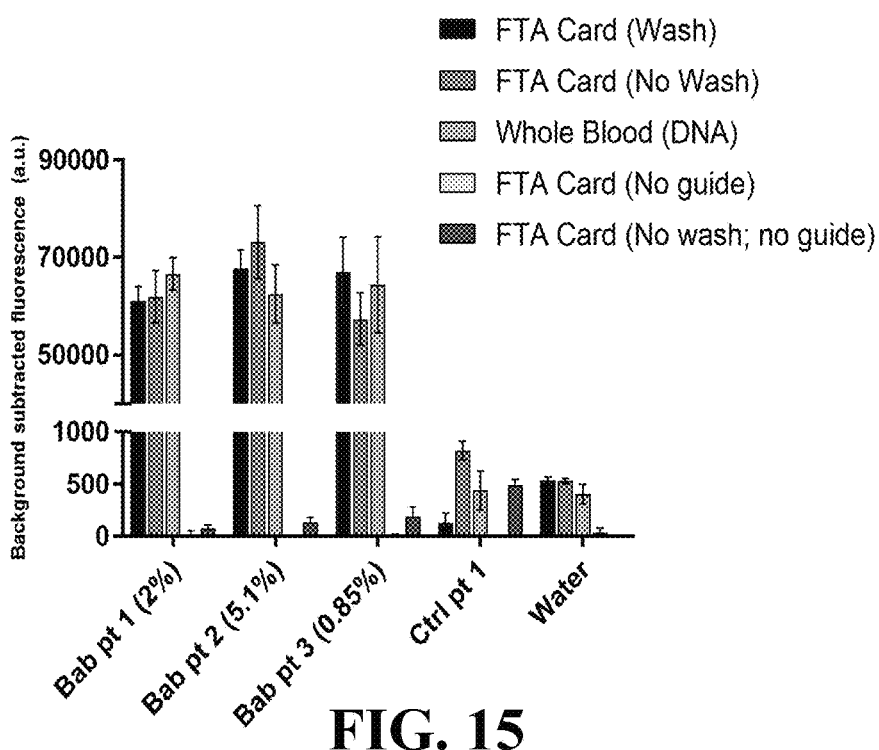
FIG. 15—Determination of whether a wash step is required for sample collected on FTA card. Wash step is somewhat time consuming, requires specific reagents, but removes cellular debris and PCR inhibitors—thus may not be necessary for RPA.
Figure 16:
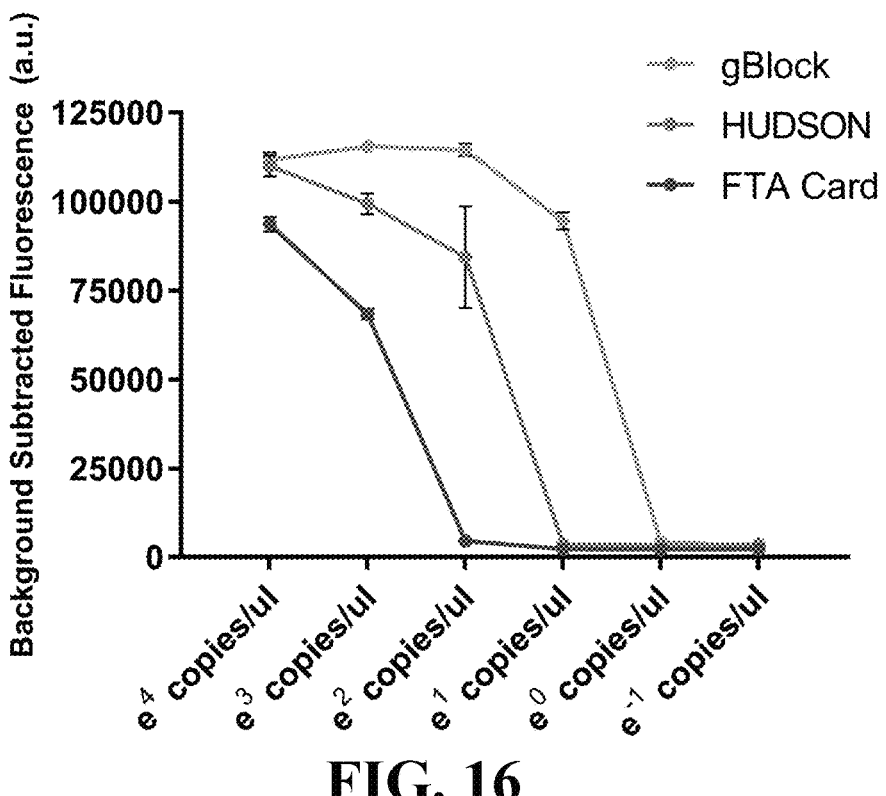
FIG. 16—Limit of Detection for *B. microti* SHERLOCK Methods, Simplifying isn't without cost: lose 10 fold sensitivity Spike in gblock into blood. For HUDSON, slightly more dilute (coagulating), increased PBS: Blood, now ~1:7.5 dilution. 3-14 parasites/uL.

SHERLOCK, which can combine isothermal nucleic acid amplification through RPA and sequence-specific template detection through Cas13a, relies on input material that has been purified or suitably altered in some manner. Pure nucleic acid extracted from clinical specimens is the predominant input sample type, but generally requires significant time, advanced materials and equipment, and specific expertise. Applicants improve upon the pre-SHERLOCK sample processing step by demonstrating the feasibility of an all-paper test. Applicants use treated filter paper as a simplified sample collection and isothermal nucleic acid isolation technique (FIG. 8A, B). Clinical specimens are spotted on paper (Whatman FTA Cards, GE Healthcare) and allowed to dry, then a 1.2 mm punch from the spotted area is used as direct input into SHERLOCK. The paper punch may be cleaned of cellular debris or introduced directly into the RPA reaction for template amplification. This then paves the way for 1) single-pot SHERLOCK that include DNA extraction and 2) complete paper-based, isothermal extraction and detection in a point-of-care test. Testing of HUDSCON and Heat treatment along with SHERLOCK has been completed (FIG. 12), as well as validating assays on clinical samples (FIG. 11). Further, use of nucleic acid extracted on filter paper has been developed (FIG. 14A, 14B), as well as surprising ability to test in plasma samples (FIG. 13).

Example 7—Powassan Virus

Powassan virus (POWV) is a tick-borne flavivirus that causes severe encephalitis. Transmitted by *Ixodes scapularis* ticks primarily in the Northeast U.S., there is a 15% mortality, and 50% with residual neurological deficits. Detection of human cases has been increasing. While there were 44 cases from 1958-2007, 125 cases were detected from 2008-2017. POWV is emerging as an underappreciated human pathogen, with evidence suggesting many POWV cases are unreported. Krow-Lucal, et al., Vector Borne Zoonotic Diseases 2018. Viral transmission can occur within 15 minutes of tick attachment and serological surveys of humans in endemic areas show the 1-8% of people have been infected with POWV.

Little is known about tick-borne strains that cause human infection and neuro-invasion. To begin to understand viral determinants of human infection and neurotropism, Applicants screened multiple samples from two subjects with POWV infection. As provided herein, Applicants assembled the first complete POWV genomes directly from clinical samples and are comparing POWV consensus genomes and quasispecies between brain and peripheral tissue.

The first subject with POWV infection, subject A, was a 79 year old male physician and gardener from Massachusetts who presented with dizziness and slurred speech, then developed altered mental status and fever. Subject A had an inflammatory cerebrospinal fluid (CSF) profile (with 284 white blood cells (WBC)/mm$^3$) and abnormal enhancement on brain MRI. Routine clinical tests for causes of infectious encephalitis were unrevealing including multiplex PCR from CSF. Applicants screened CSF, blood and urine using both rapid POWV-directed assays as well as unbiased metagenomic sequencing.

Subject B was a 60 year old man from Massachusetts with follicular lymphoma treated with rituximab who presented at Day 7 with testicular pain and fever, then developed meningismus and altered mental status. In particular, at Day 10, his speech became slurred and gate unstable. Subject B had an inflammatory CSF profile (with 10 WBC/mm$^3$ while immunosuppressed) and an abnormal MRI compatible with encephalitis. Subject B passed away 19 days after his initial presentation. Posthumously, POWV RNA was detected in serum and CSF by RT-PCR, and in CSF by metagenomic sequencing. Antigen staining of left testicular tissue was positive for POWV. No viable POWV was able to be isolated from a sample of frozen brain tissue by inoculation in cell culture or suckling mouse. A full autopsy was performed, and 13 tissues were screened for POWV.

Applicants developed a SHERLOCK assay targeting the POWV NS5 gene, yielding an assay with limit of detection as 100 copies/μL of RNA. (FIG. 18) Primary RNA samples from Subject A and B were screened by POWV SHERLOCK. (FIG. 19) Positive samples in Subject B included cerebellum at both autopsy and biopsy, left testicle, frontal cortex, and midbrain. Subject A samples with standard deviation crossing the threshold or positivity included cerebrospinal fluid, whole blood and urine.

Comparison of POWV screening by SHERLOCK to qRT-PCR and metagenomic sequencing is provided in Table 1. qRT-PCR was performed using an assay targeting the same region of NS5 as the SHERLOCK assay, with a LOD of 10 copies/μL. Metagenomic sequencing was performed using random hexamer cDNA synthesis and Nextera XT library preparation. Samples were pooled and sequenced on an Illumina MiSeq with ~5 million reads per samples.

For SHERLOCK and qRT-PCR, positive samples are shown in regular font; equivocal samples are italicized (defined as standard deviation crossed the threshold for positivity for SHERLOCK and defined as positive but <10 copies/μL for qRT-PCR). Metagenomic sequencing reads per million are shaded by order of magnitude. NDY=Not done yet.

TABLE 10

| Sample | qRT-PCT copies/uL | SHERLOCK fluorescence | Metagenomic sequencing reads per million |
|---|---|---|---|
| Subject A | | | |
| Cerebellum (autopsy) | 12,148 | 33,465 | 1,520 |
| Cerebleeum (biopsy) | 4,736 | 11,667 | 331 |
| Left testicle | 99 | 194 | *74* |
| Frontal cortex | 15 | 96 | 4 |
| Midbrain | 14 | 89 | 2 |
| Right testicle | *1* | — | 2 |
| Heart | — | *83* | — |
| Bone marrow | — | — | — |
| Liver | — | — | — |
| Basal ganglia | — | — | — |
| Prostate | — | — | — |
| Lung | — | — | — |
| Kidney | — | — | — |
| Spleen | — | — | — |
| Subject B | | | |
| CSF | *2* | *98* | *53* |
| Urine | — | *84* | NDY |
| Whole blood | — | *88* | NDY |
| Serum | — | — | NDY |

Each positive sample underwent deeper sequencing with two independent libraries starting from RNA. Hybrid capture to enrich viral RNA was performed as described in Metsky et al. Nature Biotechnology 2019. Up to ~50 million reads per sample were performed. POWV sequences were assembled using viral-ngs (viralngs.read-the-docs.io). Complete genomes were assembled with coverage between 15× (Subject A CSF, Subject B left testicle) and 250× (Subject B cerebellum).

Figures 20, 21:
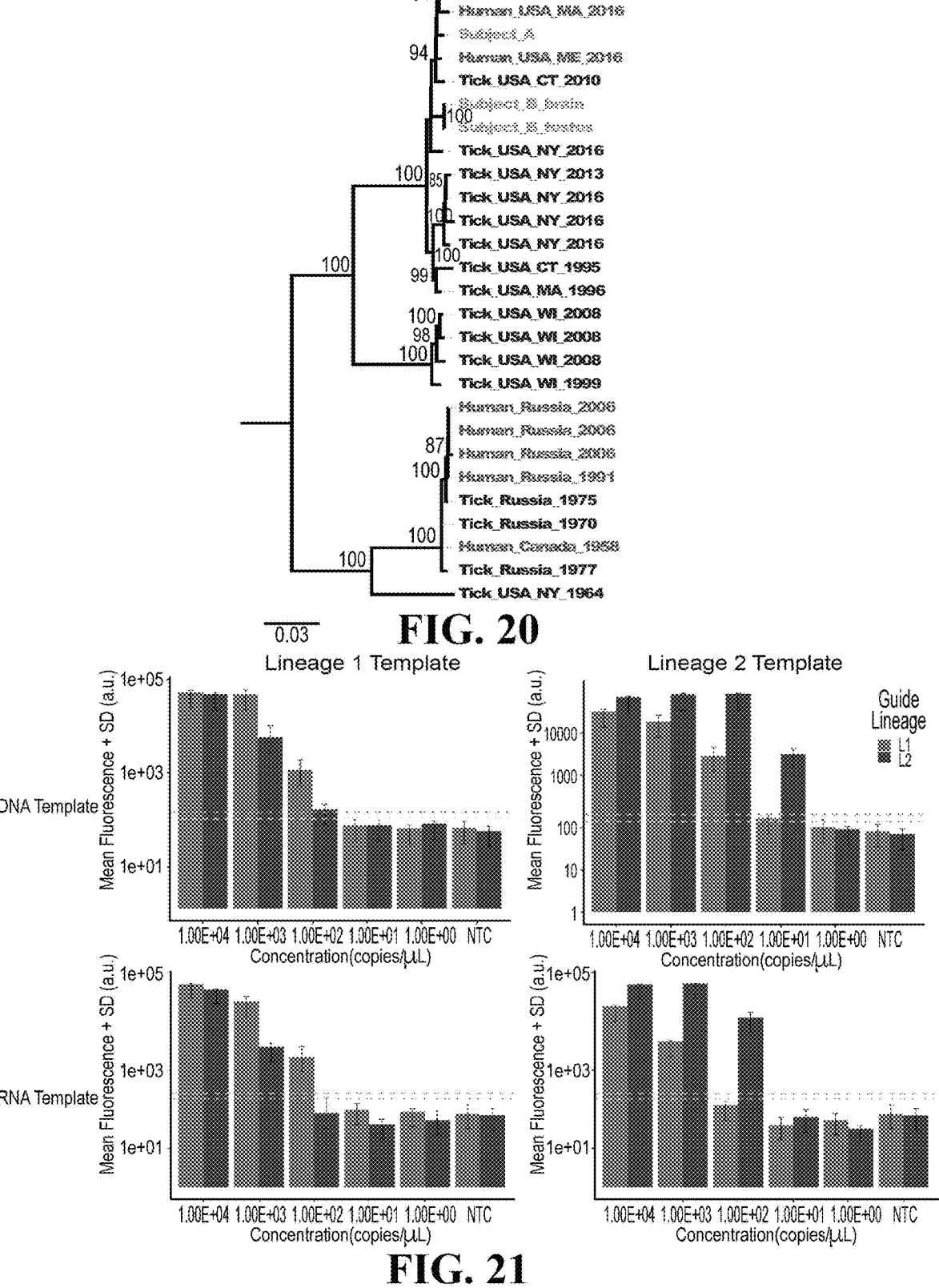
FIG. 20—Maximum-likelihood tree of available full-length POWV genomes. Subjects A and B are highlighted in red, other human cases in blue, and ticks in black.
FIG. 21—Lineage 1 and Lineage 2 POWV SHERLOCK detection of DNA template (upper panels) and RNA Template (lower panels).
Figure 22A:
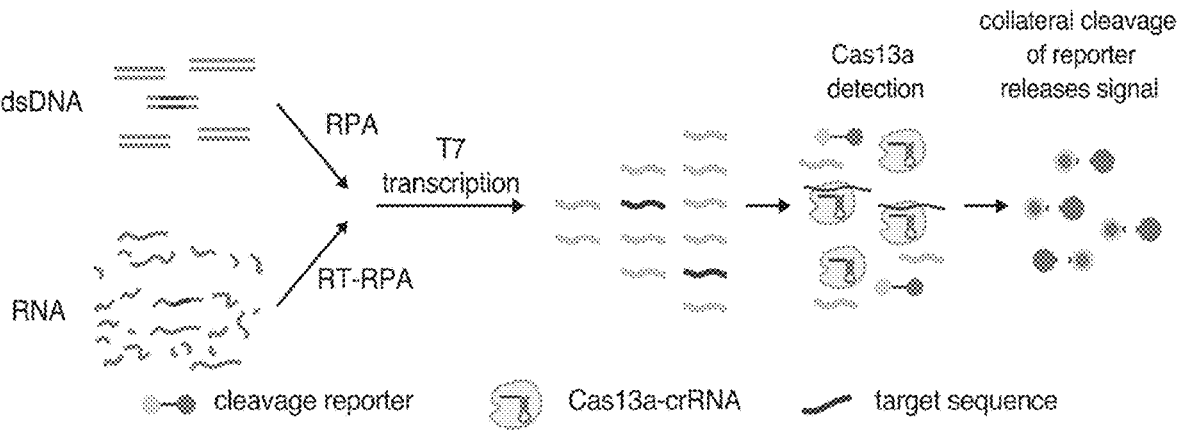
Figure 22B:
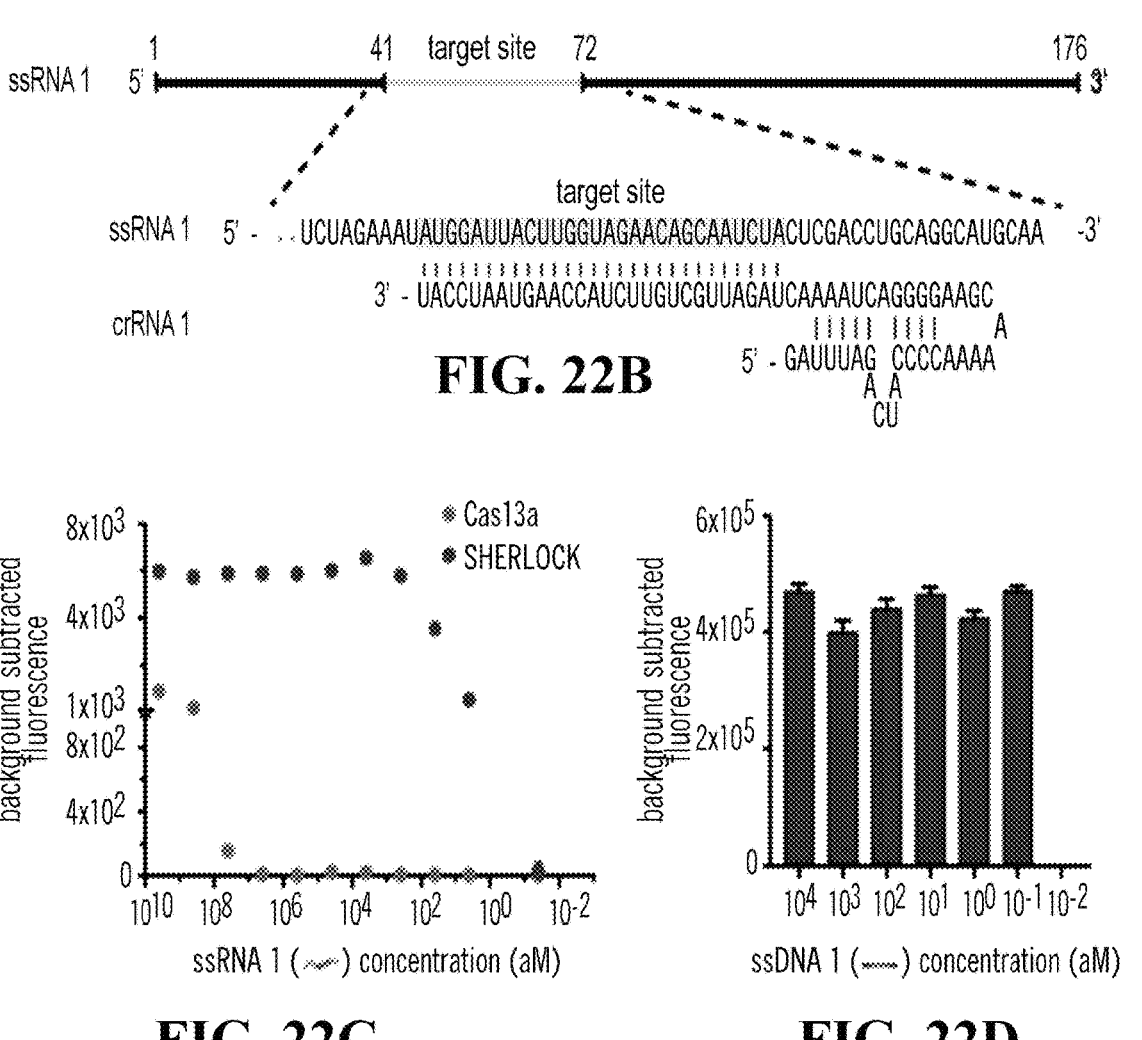

A maximum likelihood tree of available full-length POWV genomes was constructed (FIG. 20). Sequences were aligned using MAFFT as implemented in Geneious and the phylogeny was constructed using PhyML. Bootstrap values >80 are shown. The tree recapitulates the known separation between the canonical POWV lineage I (found in Canada and Russia) and lineage II (also known as Deer Tick Virus (DTV), found in the U.S.), as well as the known sub-clustering of lineage II by geography (Midwest vs. Northeast U.S.). Human cases from the Northeast U.S fall within a further sub-cluster with a subset of Northeast U.S. tick sequences.

Within-patient variation in Subject B was further explored. No differences were observed between the consensus PWV genomes of the cerebellum at biopsy and the cerebellum at autopsy (11 days later). 5 nucleotide differences were observed between cerebellum and left testicle, with one nonsynonymous change: A (ref, testicle)→V (brain) in NS4b gene. A viral quasispecies of one within-sample variant in cerebellum: synonymous, 6% frequency.

Very little is known about the viral determinants of human infection for Powassan virus (POWV), an emerging tick-borne flavivirus.

The current example described two patients with fatal POWV encephalitis, from whom complete POWV genome sequences were assembled directly from clinical samples including CSF, brain, and testicular tissue. These sequences cluster with sequences from two other human cases and a subset of ticks from the Northeast U.S. From Subject B, multiple tissue samples were obtained from autopsy, and POWV was detected in only brain and testicle, consistent with the patient's symptoms; with very few differences observed in the POWV sequences between these samples.

Future direction will include multiplexing assay with other tick-borne diseases, including those described herein, as well as lateral flow for field-deployable detection. Limit of detection will be minimized, with application for screening both tick and human clinical samples for POWV.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A nucleic acid detection system comprising:
   a. a CRISPR system comprising an effector protein and one or more guide RNAs comprising sequences selected from SEQ ID NOs: 6-13 and 15-19; and
   b. an RNA-based masking construct,
   wherein the one or more guide RNAs bind to one or more target nucleotide sequences,
   wherein the one or more guide RNAs detect a tick-borne disease state,
   wherein the tick-borne disease state is babesiosis.

2. A nucleic acid detection system, comprising:
   i) two or more CRISPR systems, each CRISPR system comprising a CRISPR effector protein and a guide RNA comprising sequences selected from SEQ ID NOs: 6-13 and 15-19; and
   ii) a set of detection constructs, each detection construct comprising a cutting motif sequence that is cut by one of the CRISPR effector proteins
   wherein the guide RNA binds to a target nucleotide sequence,
   wherein the guide RNA detects a tick-borne disease state,
   wherein the tick-borne disease state is babesiosis.

3. The detection system of claim 1, wherein the one or more target nucleotide sequences are derived from *Babesia microti*.

4. The detection system of claim 1, wherein the one or more guide RNAs bind to the cytB region of *Babesia microti*.

5. The detection system of claim 1, wherein the one or more guide RNAs bind to variants of *Babesia microti*.

6. The detection system of claim 1, wherein the one or more guide RNAs comprise 95% sequence identity to nucleotides of SEQ ID NOs: 6-13 and 15-19.

7. The nucleic acid detection system of claim 1, further comprising one or more nucleic acid amplification reagents.

8. The nucleic acid detection system of claim 1, wherein the one or more target nucleotide sequences are a target DNA sequence.

9. The nucleic acid detection system of claim 1, wherein the one or more target nucleotide sequences comprises an SNP.

10. The nucleic acid detection system of claim 9, wherein the one or more guide RNAs bind to the one or more target nucleotide sequences associated with the tick-borne disease state at a SNP cytB M134I of *B. microti*.

11. A lateral flow device comprising the nucleic acid detection system of claim 1.

12. The lateral flow device of claim 11, wherein the CRISPR system is freeze-dried on a lateral flow strip.

13. The lateral flow device of claim 11, wherein the lateral flow device comprises a substrate comprising a first end, wherein the first end comprises a sample loading portion and a first region loaded with a detectable ligand, the nucleic acid detection system, a first capture region comprising a first binding agent, and a second capture region comprising a second binding agent, optionally wherein the sample loading portion comprises a receiving input for a blood stick.

14. The lateral flow device of claim 13, wherein the sample loading portion further comprises one or more amplification reagents to amplify the one or more target nucleotide sequences, wherein the reagents optionally comprise reagents for nucleic acid sequence-based amplification (NASBA), recombinase polymerase amplification (RPA), loop-mediated isothermal amplification (LAMP), strand displacement amplification (SDA), helicase-dependent amplification (HDA), nicking enzyme amplification reaction (NEAR), PCR, multiple displacement amplification (MDA), rolling circle amplification (RCA), ligase chain reaction (LCR), or ramification amplification method (RAM).

15. The lateral flow device of claim 11, wherein the RNA construct comprises a first molecule on a first end and a second molecule on a second end, optionally wherein a first capture region comprises a first binding agent that specifically binds the first molecule of a reporter construct.

16. The lateral flow device of claim 15, wherein the first molecule is FITC and the second molecule is biotin, or vice versa.

17. The lateral flow device of claim 13, wherein the first binding agent is an antibody that is fixed or otherwise immobilized to the first capture region, or wherein the second capture region comprises a second binding agent that specifically binds a second molecule of a reporter construct, or the detectable ligand.

18. The lateral flow device of claim 17, wherein the second binding agent is an antibody or an antibody-binding protein that is fixed or otherwise immobilized to the second capture region.

19. A method for detecting target nucleic acids in a sample, comprising:
   distributing a sample or set of samples into one or more individual discrete volumes, the individual discrete volumes comprising the nucleic acid detection system of claim 1.

20. The method of claim 19, wherein the sample is blood, a red blood cell supernatant, plasma, or cerebrospinal fluid.

21. The method of claim 19, wherein the target nucleic acid is from a sample of cell free DNA.

22. The method of claim 19, wherein the target nucleic acid is DNA and wherein the method further comprises extracting DNA from cells in the sample.

23. The method of claim 19, wherein the sample is collected on a nucleic acid collection card, optionally further comprising eluting the sample from the nucleic acid collection card.

24. The nucleic acid detection system of claim 2, wherein each CRISPR system further comprises an activation sequence, wherein the CRISPR effector protein is activated upon cleavage of the activation sequence.

*     *     *     *     *